US008268361B2

(12) United States Patent
Ahlfors

(10) Patent No.: US 8,268,361 B2
(45) Date of Patent: Sep. 18, 2012

(54) ACELLULAR BIOABSORBABLE TISSUE REGENERATION MATRICES

(76) Inventor: Jan-Eric W. Ahlfors, St. John's (AG)

( * ) Notice: Subject to any disclaimer, the term of this patent is extended or adjusted under 35 U.S.C. 154(b) by 488 days.

(21) Appl. No.: 11/588,840

(22) Filed: Oct. 26, 2006

(65) Prior Publication Data

US 2007/0202189 A1 Aug. 30, 2007

Related U.S. Application Data

(60) Provisional application No. 60/730,614, filed on Oct. 26, 2005.

(51) Int. Cl.
 *A61K 35/14* (2006.01)
(52) U.S. Cl. ........................................ 424/529; 424/93.7
(58) Field of Classification Search .................. None
 See application file for complete search history.

(56) References Cited

U.S. PATENT DOCUMENTS

| | | | |
|---|---|---|---|
| 5,041,138 A | 8/1991 | Vacanti et al. | |
| 5,102,407 A * | 4/1992 | Carmen et al. ................ | 604/410 |
| 5,135,851 A | 8/1992 | Kajander et al. | |
| 5,399,665 A | 3/1995 | Barrera et al. | |
| 5,514,378 A | 5/1996 | Mikos et al. | |
| 5,567,612 A | 10/1996 | Vacanti et al. | |
| 5,632,778 A | 5/1997 | Goldstein | |
| 5,709,854 A | 1/1998 | Griffith-Cima et al. | |
| 5,716,404 A | 2/1998 | Vacanti et al. | |
| 5,736,372 A | 4/1998 | Vacanti et al. | |
| 5,741,685 A | 4/1998 | Vacanti | |
| 5,759,830 A | 6/1998 | Vacanti et al. | |
| 5,770,193 A | 6/1998 | Vacanti et al. | |
| 5,770,417 A | 6/1998 | Vacanti et al. | |
| 5,804,178 A | 9/1998 | Vacanti et al. | |
| 5,855,610 A | 1/1999 | Vacanti et al. | |
| 5,944,754 A | 8/1999 | Vacanti | |
| 6,027,744 A | 2/2000 | Vacanti et al. | |
| 6,051,750 A | 4/2000 | Bell | |
| 6,095,148 A | 8/2000 | Shastri et al. | |
| 6,123,727 A | 9/2000 | Vacanti et al. | |
| 6,139,574 A | 10/2000 | Vacanti et al. | |
| 6,171,610 B1 | 1/2001 | Vacanti et al. | |
| 6,176,874 B1 | 1/2001 | Vacanti et al. | |
| 6,281,015 B1 | 8/2001 | Mooney et al. | |
| 6,309,635 B1 | 10/2001 | Ingber et al. | |
| 6,348,069 B1 | 2/2002 | Vacanti et al. | |
| 6,387,367 B1 | 5/2002 | Davis-Sproul et al. | |
| 6,455,311 B1 | 9/2002 | Vacanti | |
| 6,576,265 B1 | 6/2003 | Spievack | |
| 6,689,608 B1 | 2/2004 | Mikos et al. | |
| 6,692,738 B2 | 2/2004 | MacLaughlin et al. | |
| 6,730,298 B2 | 5/2004 | Griffith-Cima et al. | |
| 6,840,962 B1 | 1/2005 | Vacanti et al. | |
| 6,899,915 B2 | 5/2005 | Yelick et al. | |
| 6,987,987 B1 | 1/2006 | Vacanti et al. | |
| 7,060,492 B2 | 6/2006 | Vacanti et al. | |
| 7,078,032 B2 | 7/2006 | MacLaughlin et al. | |
| 7,310,516 B1 | 12/2007 | Vacanti et al. | |
| 7,319,035 B2 | 1/2008 | Vacanti et al. | |
| 8,043,614 B2 | 10/2011 | Ahlfors | |
| 2001/0053353 A1 | 12/2001 | Griffith et al. | |
| 2001/0055588 A1 | 12/2001 | Griffith-Cima et al. | |
| 2002/0022592 A1 | 2/2002 | Detmar et al. | |
| 2002/0031500 A1 | 3/2002 | MacLaughlin et al. | |
| 2002/0115165 A1 | 8/2002 | Stein et al. | |
| 2002/0119180 A1 | 8/2002 | Yelick et al. | |
| 2002/0151050 A1 | 10/2002 | Vacanti et al. | |
| 2002/0172705 A1 | 11/2002 | Murphy et al. | |
| 2002/0182241 A1 | 12/2002 | Borenstein et al. | |
| 2003/0003575 A1 | 1/2003 | Vacanti et al. | |
| 2003/0054022 A1 | 3/2003 | Spievack | |
| 2003/0129751 A1 | 7/2003 | Grikscheit et al. | |
| 2003/0143207 A1 | 7/2003 | Livesey et al. | |
| 2003/0187515 A1 | 10/2003 | Hariri et al. | |
| 2004/0005297 A1 | 1/2004 | Connelly et al. | |
| 2004/0033598 A1 | 2/2004 | Vacanti et al. | |
| 2004/0057942 A1 | 3/2004 | Vacanti et al. | |
| 2004/0086497 A1 | 5/2004 | MacLaughlin et al. | |
| 2004/0101518 A1 | 5/2004 | Vacanti et al. | |
| 2004/0137613 A1 | 7/2004 | Vacanti et al. | |
| 2004/0170612 A1 | 9/2004 | Griffith et al. | |
| 2004/0175823 A1 | 9/2004 | Vacanti et al. | |
| 2004/0219489 A1 | 11/2004 | Yelick et al. | |

(Continued)

FOREIGN PATENT DOCUMENTS

CA  2395117  7/2001

(Continued)

OTHER PUBLICATIONS

Arevalo-Silva, C. A. et al., Internal support of tissue-engineered cartilage, Arch. Otolaryngol. Head Neck Surg. 126, 1448-1452, 2000.
Basso, et al., Graded Histological Locomotor Outcomes after Spinal Cord Contusion Using the NYU Weight-Drop Device Versus Transection, Exper. Neuro. 130, 244-56, 1996.
Becker, R. O. et al., Regeneration of the ventricular myocardium in *amphibians*, Nature 248, 145-147, 1974.
Cascone, M. G.et al., Bioartificial polymeric materials based on polysaccharides, J Biomater. Sci. Polym. Ed. 12, 267-281, 2001.
Desgrandchamps, F., Biomaterials in functional reconstruction, Curr. Opin. Urol. 10, 201-206, 2000.
Dobkin, B. H., and Havton, L.A., Basic Advances and New Avenues in Therapy of Spinal Cord Injury, Ann Rev. Med. 55, 255-82, 2004.
International Preliminary Report on Patentability for PCT/US2006/040216 (Apr. 2008).

(Continued)

*Primary Examiner* — Allison Ford
(74) *Attorney, Agent, or Firm* — Nevrivy Patent Law Group P.L.L.C.

(57) ABSTRACT

The present invention provides methods and compositions useful in the regeneration of damaged, lost and/or degenerated tissue in humans and animals. In certain embodiments, the present invention provides an acellular bioabsorbable tissue regeneration matrix, methods of making such a matrix, and methods of using such a matrix for the regeneration of damaged, lost and/or degenerated tissue. In certain embodiments, methods and compositions of the present invention are useful in the treatment of damaged, lost and/or degenerated nerve tissue.

73 Claims, 40 Drawing Sheets

U.S. PATENT DOCUMENTS

| | | | |
|---|---|---|---|
| 2005/0002982 A1 | 1/2005 | Mooney et al. |
| 2005/0043819 A1 | 2/2005 | Schmidt et al. |
| 2005/0060033 A1 | 3/2005 | Vacanti et al. |
| 2005/0112760 A1 | 5/2005 | Kamil et al. |
| 2005/0123520 A1 | 6/2005 | Eavey et al. |
| 2005/0202557 A1 | 9/2005 | Borenstein et al. |
| 2006/0019326 A1 | 1/2006 | Vacanti et al. |
| 2006/0024249 A1 | 2/2006 | Yelick et al. |
| 2006/0099191 A1 | 5/2006 | Hoh et al. |
| 2006/0136182 A1 | 6/2006 | Vacanti et al. |
| 2006/0141000 A1 | 6/2006 | Mikos et al. |
| 2007/0005139 A1 | 1/2007 | Vacanti et al. |
| 2007/0148139 A1 | 6/2007 | Vacanti et al. |
| 2007/0281353 A1 | 12/2007 | Vacanti et al. |
| 2008/0026464 A1 | 1/2008 | Borenstein et al. |

FOREIGN PATENT DOCUMENTS

| | | |
|---|---|---|
| EP | 299010 | 1/1989 |
| EP | 422209 | 4/1991 |
| EP | 469070 | 2/1992 |
| EP | 610423 | 8/1994 |
| EP | 619732 | 10/1994 |
| EP | 794790 | 9/1997 |
| EP | 797460 | 10/1997 |
| EP | 836453 | 4/1998 |
| EP | 906069 | 4/1999 |
| EP | 1076533 | 2/2001 |
| EP | 1187909 | 3/2002 |
| EP | 1535633 A1 | 6/2005 |
| WO | WO-8803785 | 6/1988 |
| WO | WO-9012603 | 11/1990 |
| WO | WO-9012604 | 11/1990 |
| WO | WO-9307913 | 4/1993 |
| WO | WO-9308850 | 5/1993 |
| WO | WO-9409760 | 5/1994 |
| WO | WO-9425079 | 11/1994 |
| WO | WO-9425080 | 11/1994 |
| WO | WO-9603160 | 2/1996 |
| WO | WO-9618411 | 6/1996 |
| WO | WO-9618424 | 6/1996 |
| WO | WO-9640002 | 12/1996 |
| WO | WO-9640887 | 12/1996 |
| WO | WO-9716545 | 5/1997 |
| WO | WO-9717038 | 5/1997 |
| WO | WO-9955252 | 11/1999 |
| WO | WO-0066036 | 11/2000 |
| WO | WO-0149113 | 7/2001 |
| WO | WO-0155212 | 8/2001 |
| WO | WO-02057428 | 7/2002 |
| WO | WO 02/067867 A2 | 9/2002 |
| WO | WO-03076564 | 9/2003 |
| WO | WO-03082145 | 10/2003 |
| WO | WO-2004026115 | 4/2004 |
| WO | WO-2004030626 | 4/2004 |
| WO | WO-2004034890 | 4/2004 |
| WO | WO-2004034984 | 4/2004 |
| WO | WO-2004065616 | 8/2004 |
| WO | WO-2005016114 | 2/2005 |
| WO | WO-2005034624 | 4/2005 |
| WO | WO-2005060396 | 7/2005 |
| WO | WO-2006020240 | 2/2006 |
| WO | WO-2006052551 | 5/2006 |

OTHER PUBLICATIONS

International Search Report for PCT/US2006/042016 (Mar. 2007).
Jeong, B. et al., Drug release from biodegradable injectable thermosensitive hydrogel of PEG-PLGA-PEG triblock copolymers, J Control Release 63, 155-163, 2000.
Kim, T. K. et al., Experimental model for cartilage tissue engineering to regenerate the zonal organization of articular cartilage, Osteoarthritis Cartilage 11, 653-664, 2003.
Kojima, K. et al., A composite tissue-engineered trachea using sheep nasal chondrocyte and epithelial cells, Faseb J. 17, 823-828, 2003.
Kopecek, J., Smart and genetically engineered biomaterials and drug delivery systems, Eur. J. Pharm. Sci. 20, 1-16, 2003.
Marler, J. J. et al., Soft-tissue augmentation with injectable alginate and syngeneic fibroblasts, Plast. Reconstr. Surg. 105, 2049-2058, 2000.
McDonald, J. W. et al., Spinal Cord Injury Seminar, Lancet, 359:417-25, 2002.
Peppas, N. A. et al., Hydrogels in pharmaceutical formulations, Eur. J. Pharm. Biopharm. 50, 27-46, 2000.
Saim, A. B. et al., Engineering autogenous cartilage in the shape of a helix using an injectable hydrogel scaffold, Laryngoscope 110, 1694-1697, 2000.
Thompson, C. A. et al., Percutaneous transvenous cellular cardiomyoplasty: A novel nonsurgical approach for myocardial cell transplantation, J. Am. Coll. Cardiol. 41, 1964-1971, 2003.
Tsai, E. C. et a., Synthetic hydrogel guidance channels facilitate regeneration of adult rat brainstem motor axons after complete spinal cord transection, J. Neurotrauma. 21, 789-804, 2004.
Tsuji, M., Induction of Neurite Outgrowth in PC12 Cells alpha-phenyl-N-terbutylnitron thorugh Activation of protein Kinase C and the Ras-Extracellular Singa-Regulated Kinase pathway, J. BioChem, 276: 32779-85, 2001.
Vacanti, M. et al., Identification and initial characterization of spore-like cells in adult mammamls, J Cell. Biochem. 80, No. 3, 455-460, 2001.
Wake, M. C. et al., Dynamics of fibrovascular tissue ingrowth in hydrogel foams, Cell Transplant. 4, 275-279, 1995.
Weng, Y. et al., Tissue-engineered composites of bone and cartilage for mandible condylar reconstruction, J. Oral Maxillofac. Surg. 59, 185-190, 2001.
Written Opinion for PCT/US2006/042016 (Apr. 2008).
Wu, Y.Y., Synergistic Induction of Neurite Outgrowth by Nerve Growth Factor or Epidermal Growth Factors and Interleukin-6 PC12Cells, J Bio Chem, vol. 271, 13033-13039, 1996.
Zhang, Y., and Chu, C. C., In vitro release behavior of insulin from biodegradable hybrid hydrogel networks of polysaccharide and synthetic biodegradable polyester, J. Biomater. Appl. 16, 305-325, 2002.
Zimmermann, U. et al., Hydrogel-based non-autologous cell and tissue therapy, Biotechniques 29, 564-572, 574, 576 passim, 2000.

* cited by examiner

Figure 1. Transdifferention of Macrophages into Von Willebrand Factor-positive Endothelial-like Cells.
A. 200x
B. 400x
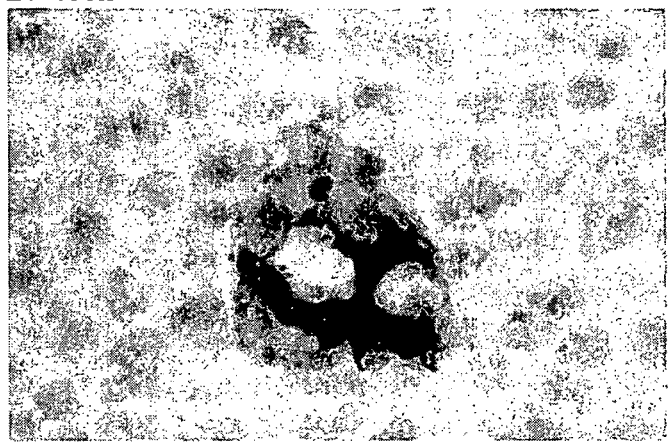
C. 400x

Figure 2. Regeneration Matrix Supports Angiogenesis in Damaged Spinal Cord Tissue in Rats.
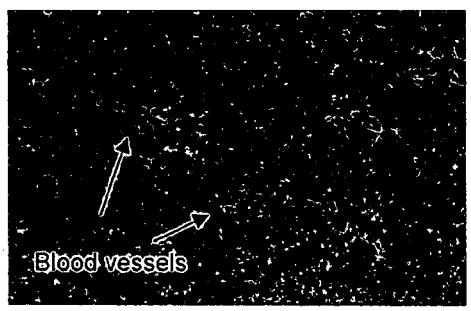
A. Healthy Rat Spinal Cord
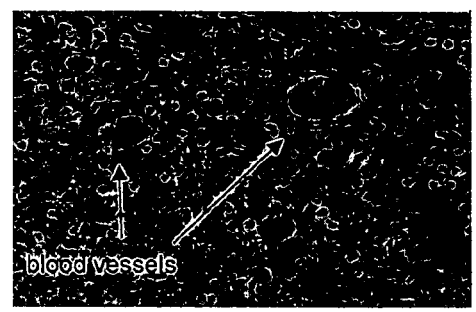
C. Injury Site with $RM_x$ Implant
B. Injury Site without $RM_x$ Implant
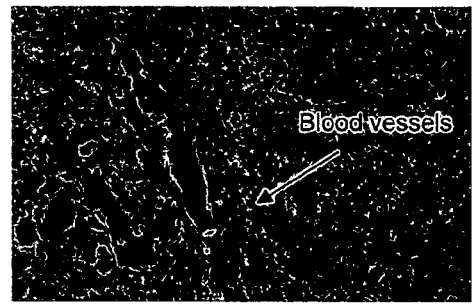
D. Injury Site with $RM_x$ Implant Figure 3. Photograph of Regeneration Matrix Produced Using Non-clotted Blood and 1.2 μm Final Filtration Contained with the Opticell® Production Cassette.
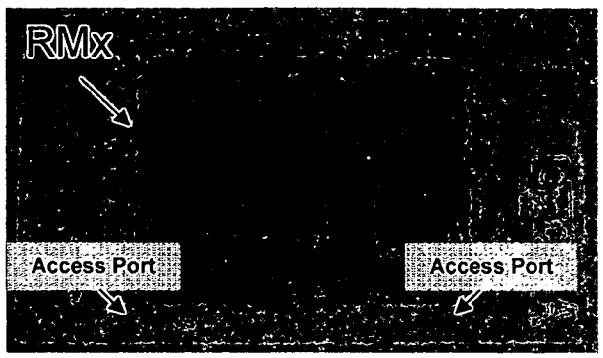

Figure 4. Regeneration Matrix Produced From Whole Blood Lacks Any Indication of Intact Cells or Nuclei.
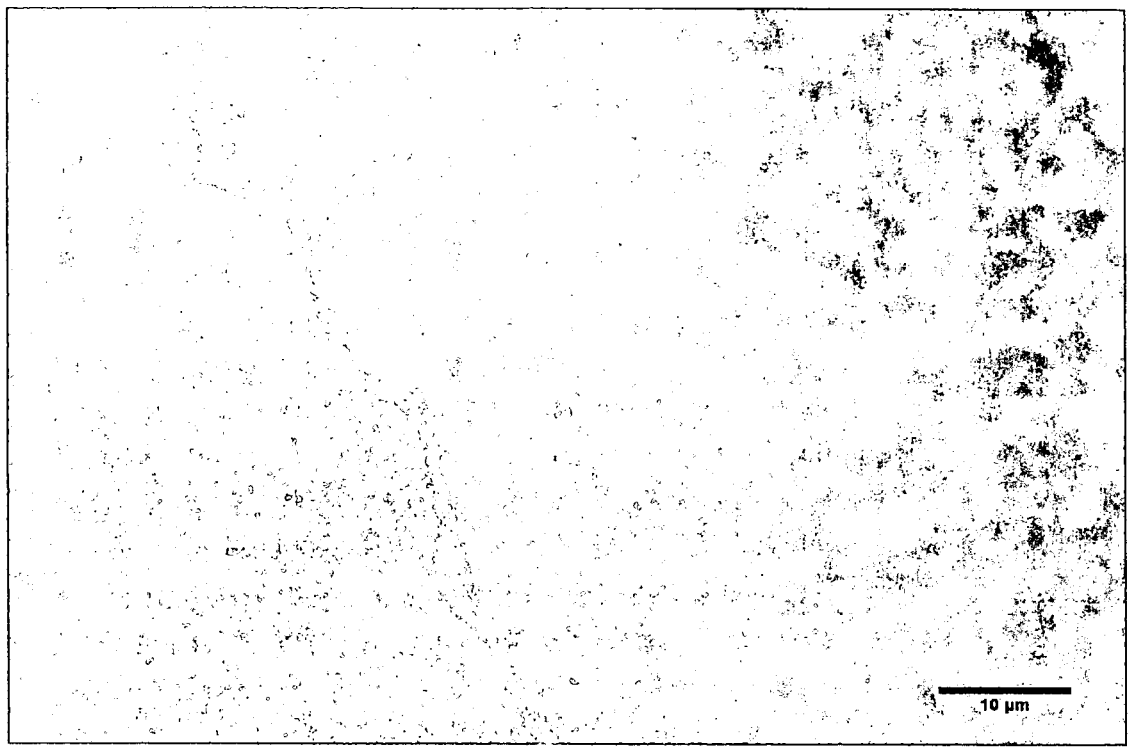

Figure 5. Electron Micrographs of Regeneration Matrix Produced Using Clotted Blood and 5 μm Final Filtration. A - 200x, B - 1000x, C – 7500x, D – 7500x.
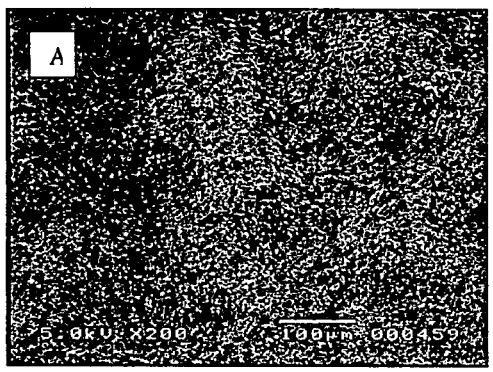
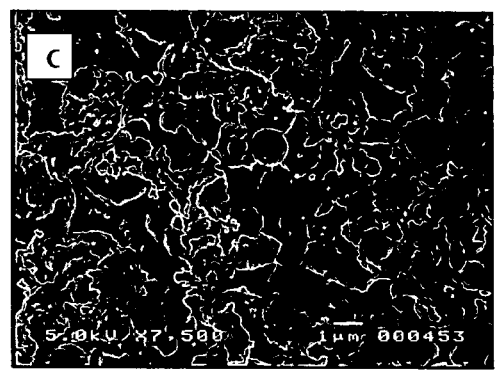
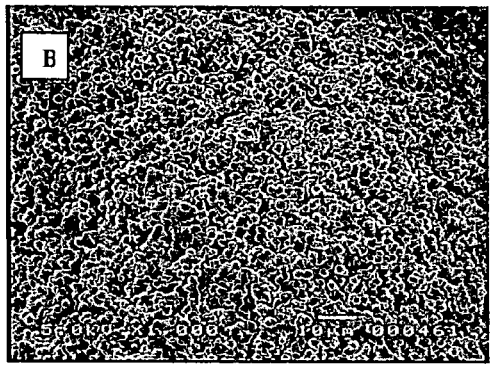
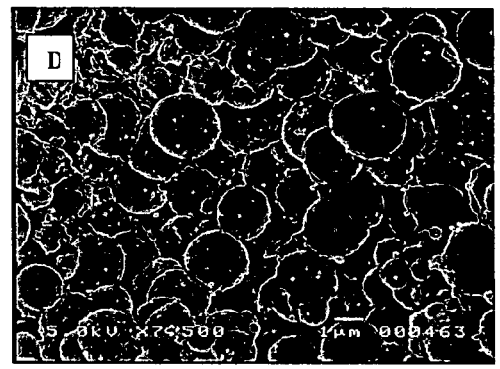

Figure 6. Scanning Electron Micrographs of Regeneration Matrix Produced Using Clotted Blood and 1.2 μm Final Filtration (21 days). A - 200x, B - 1000x, C – 7500x, D – 7500x.
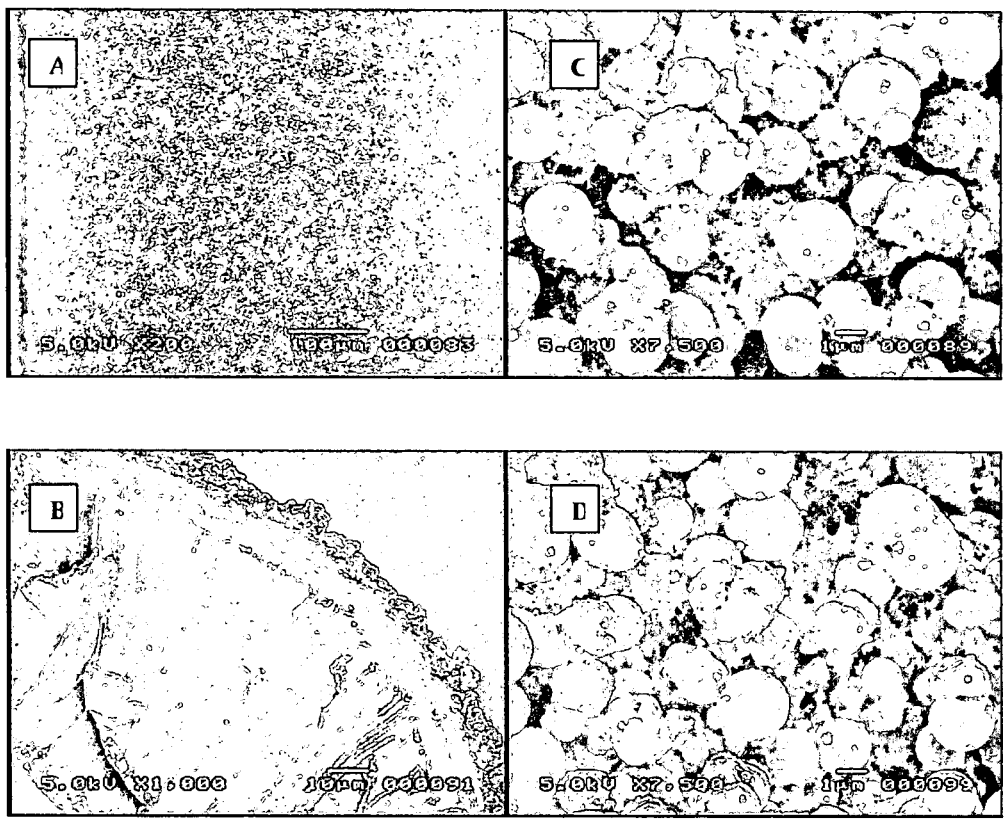

Figure 7. Electron Micrographs of Regeneration Matrix Produced Using Non-clotted (Using EDTA) Blood and 1.2 μm Final Filtration (21 days). A - 200x, B - 1500x, C – 5000x, D – 10000x.
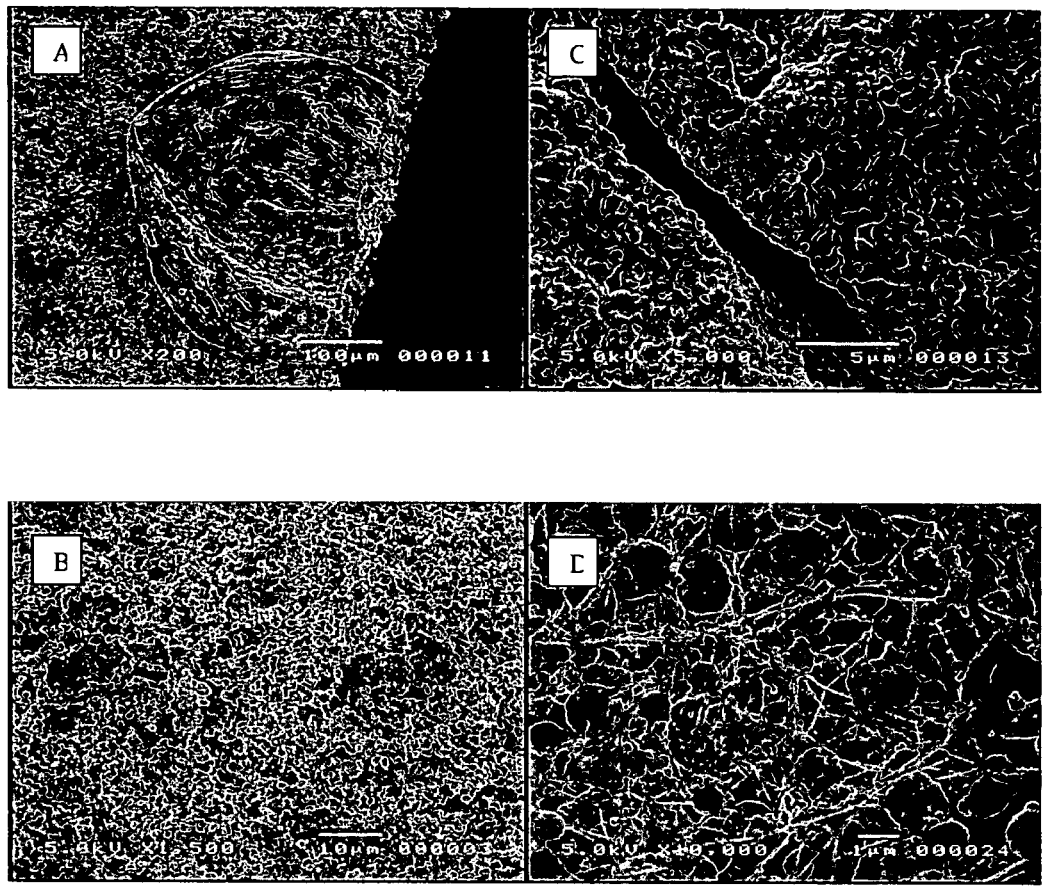

Figure 8. Light Micrograph of Regeneration Matrix Produced Using Non-clotted Blood and 1.2 μm Final Filtration (100x Magnification).
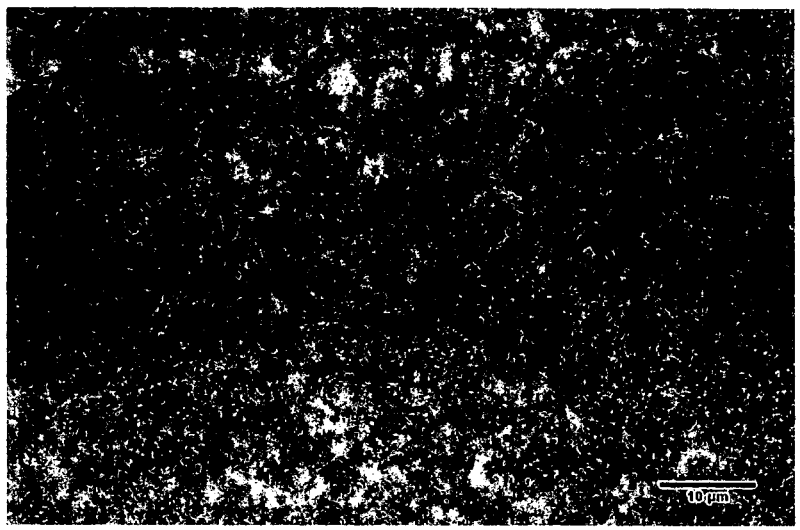

Figure 9. Transmission Electron Microsopy of Regeneration Matrix.
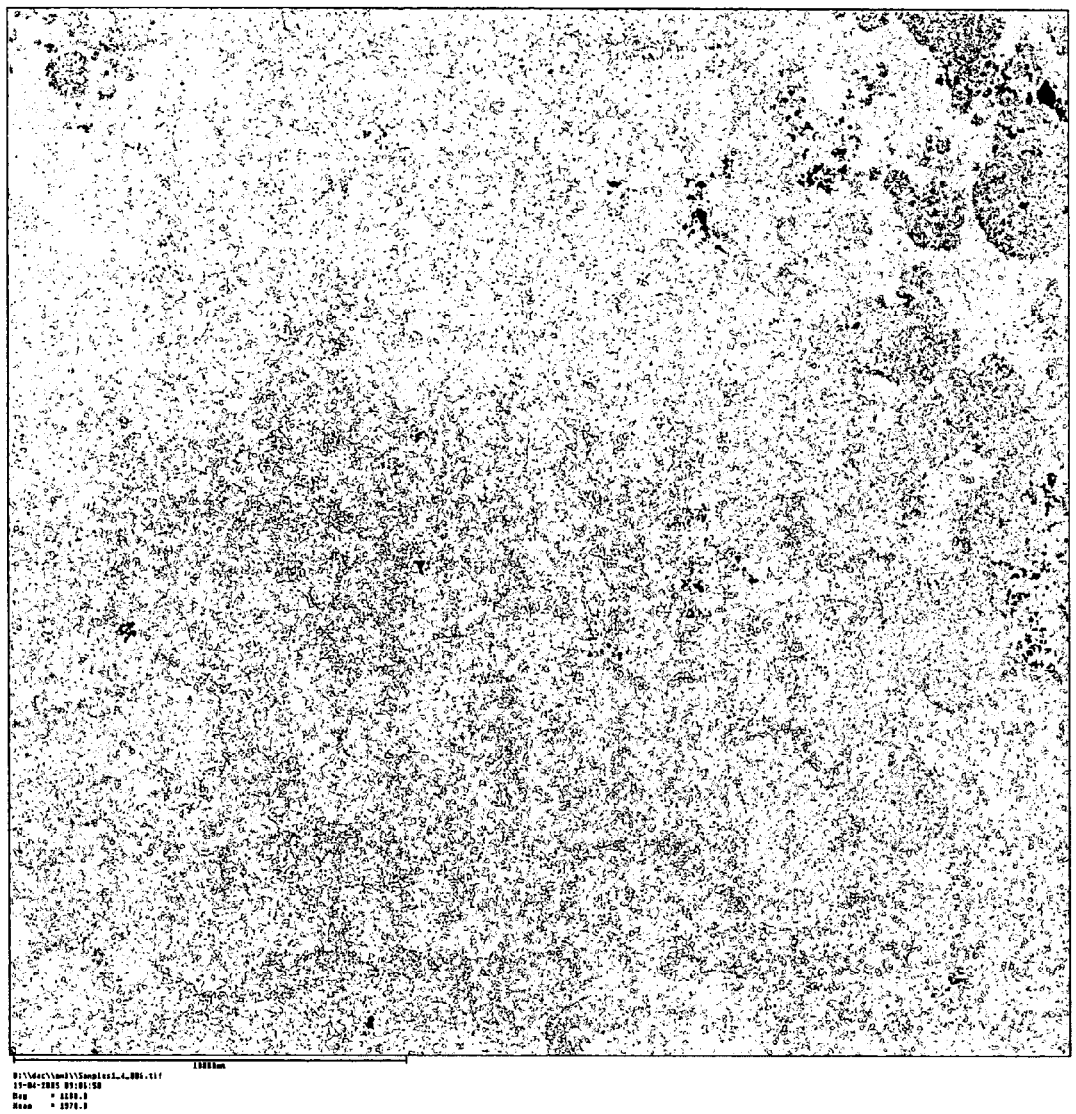

Figure 10. Transmission Electron Microsopy of Regeneration Matrix.
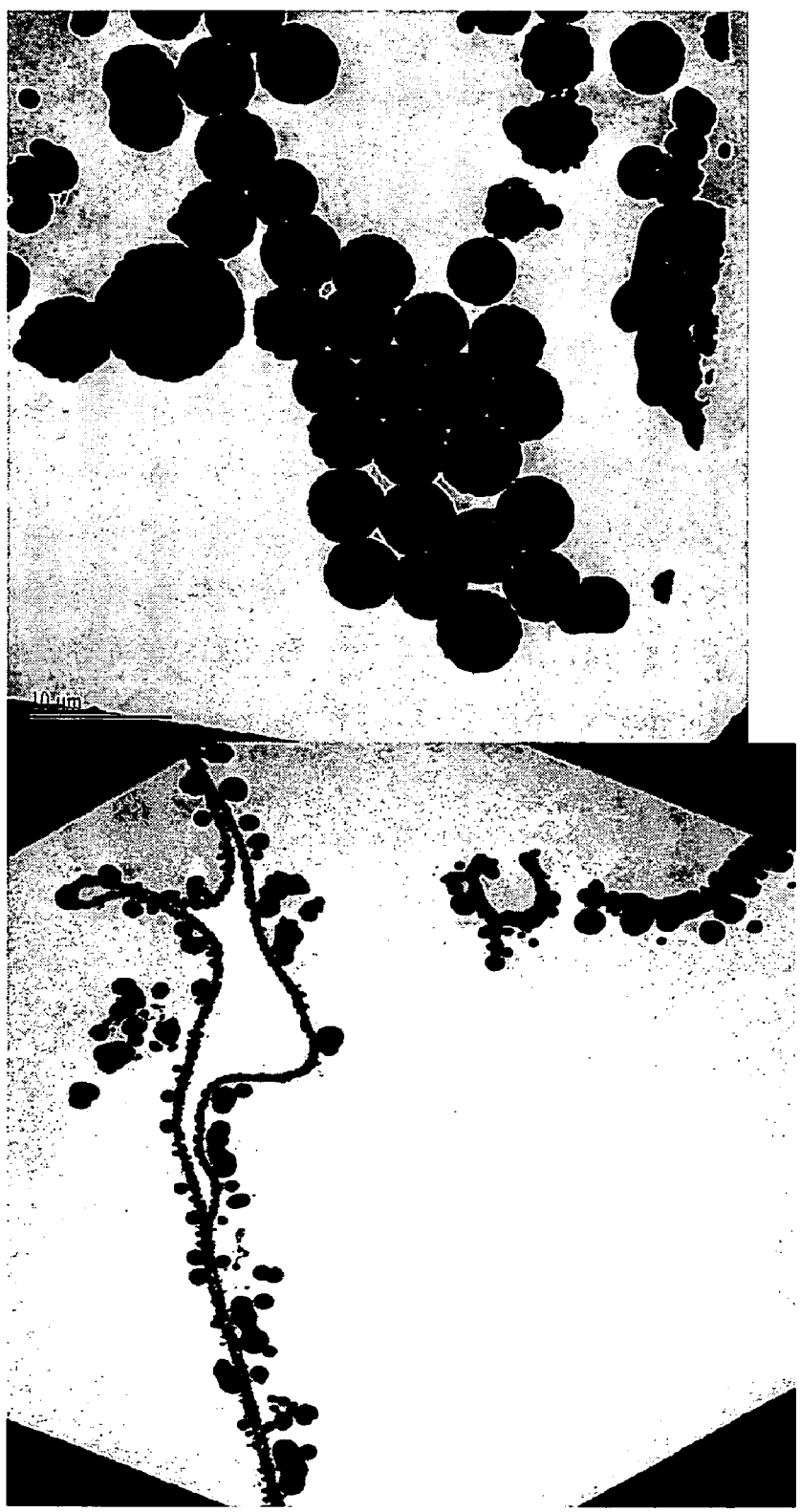

Figure 11. Transmission Electron Microsopy of Regeneration Matrix.
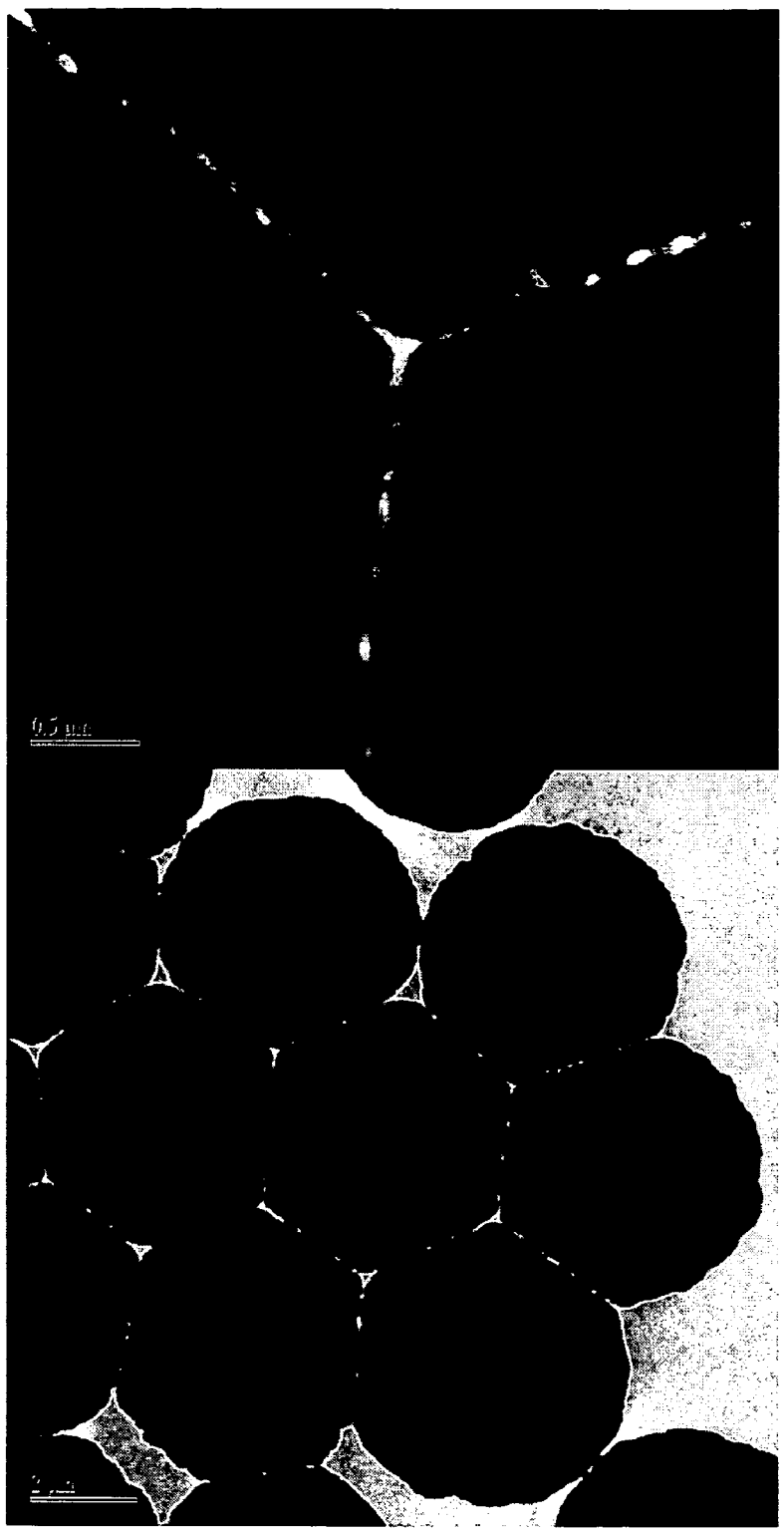

Figure 12. SDS-PAGE Analysis of Regeneration Matrix.
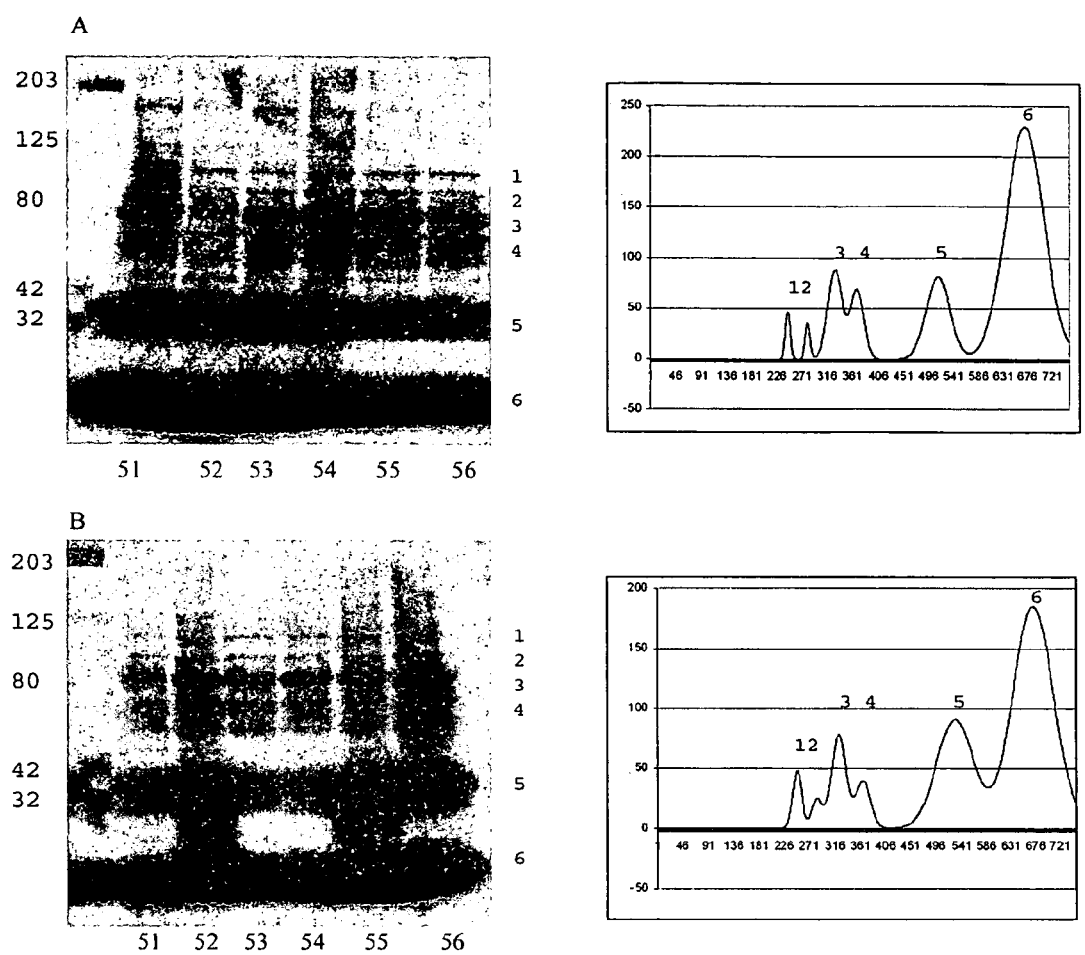

Figure 13. Total RNA Content (µg) in Regeneration Matrix, Supernatant, and Whole Opticell® Culture (1 µm Filtered).
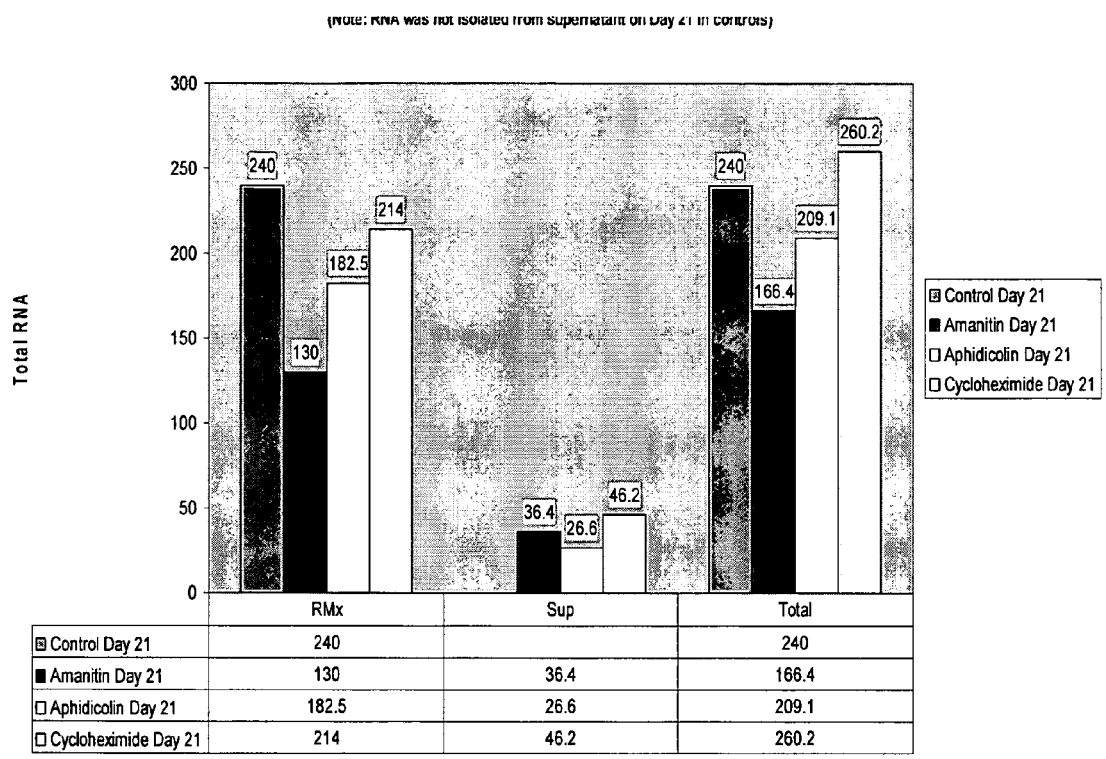

Figure 14. Total Protein Content in Regeneration Matrix, Supernatant, and Whole Opticell® Culture (5 µm Filtered).
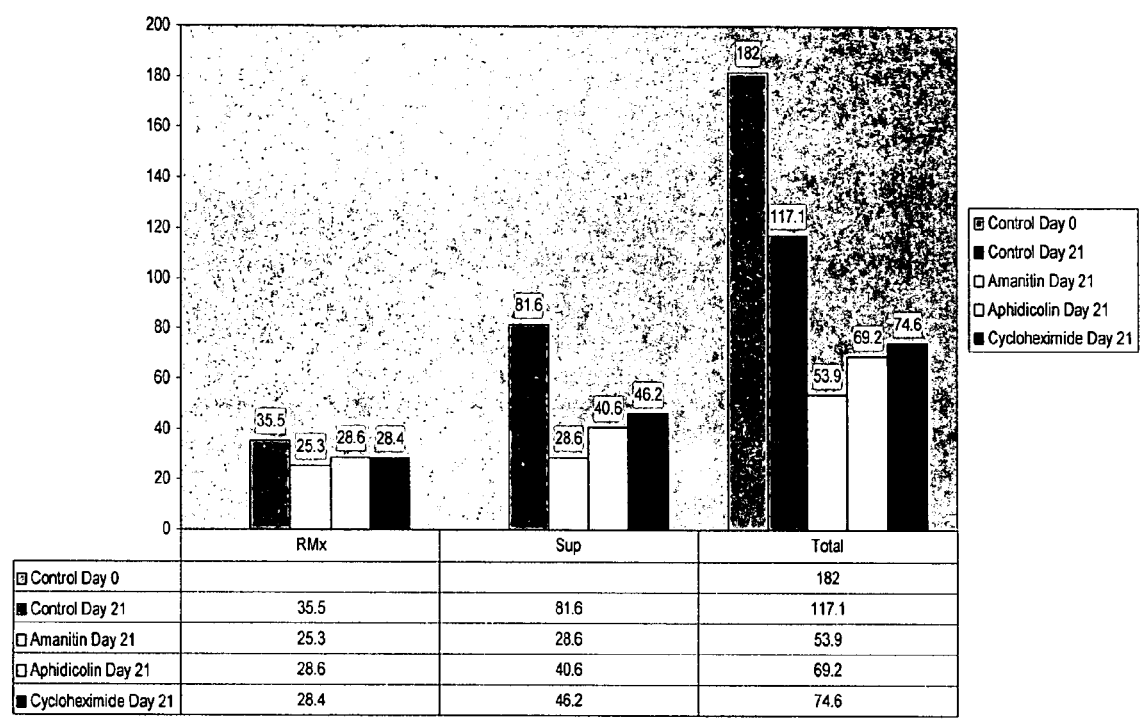
|  | RMx | Sup | Total |
|---|---|---|---|
| Control Day 0 |  |  | 182 |
| Control Day 21 | 35.5 | 81.6 | 117.1 |
| Amanitin Day 21 | 25.3 | 28.6 | 53.9 |
| Aphidicolin Day 21 | 28.6 | 40.6 | 69.2 |
| Cycloheximide Day 21 | 28.4 | 46.2 | 74.6 |

Figure 15. Total Protein Content in Regeneration Matrix, Supernatant, and Whole Opticell® Culture (1 μm Filtered).
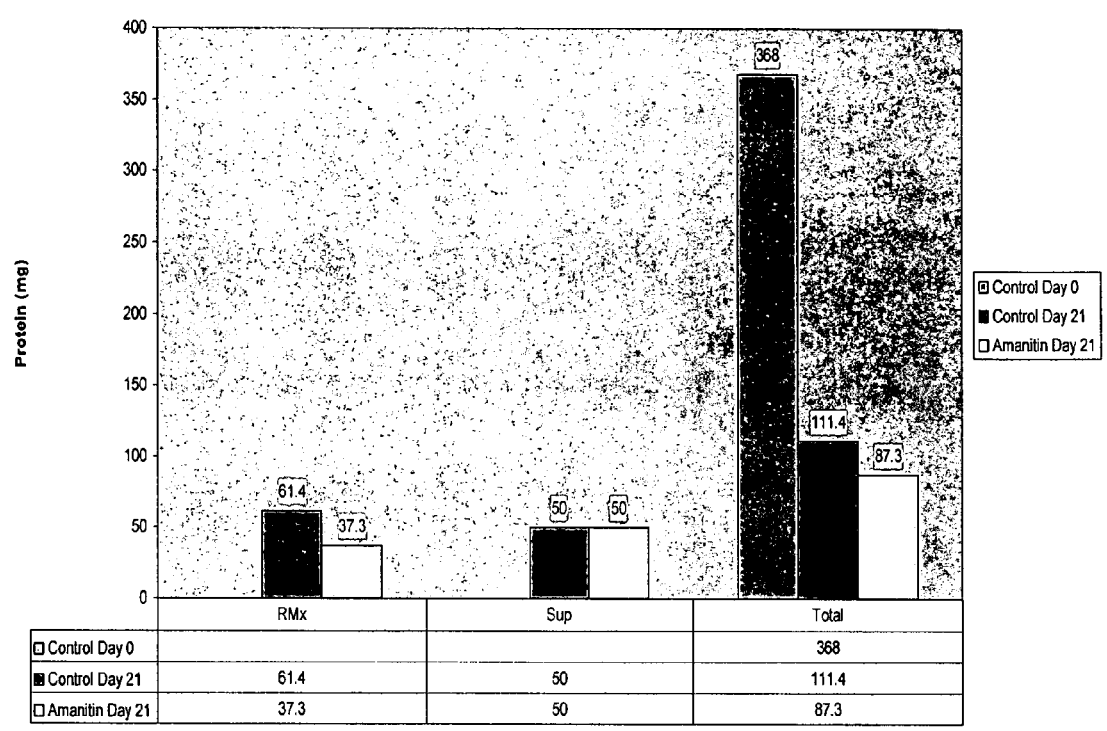

Figure 16. Total Lipid Content in Regeneration Matrix, Supernatant, and Whole Opticell® Culture (1 μm Filtered).
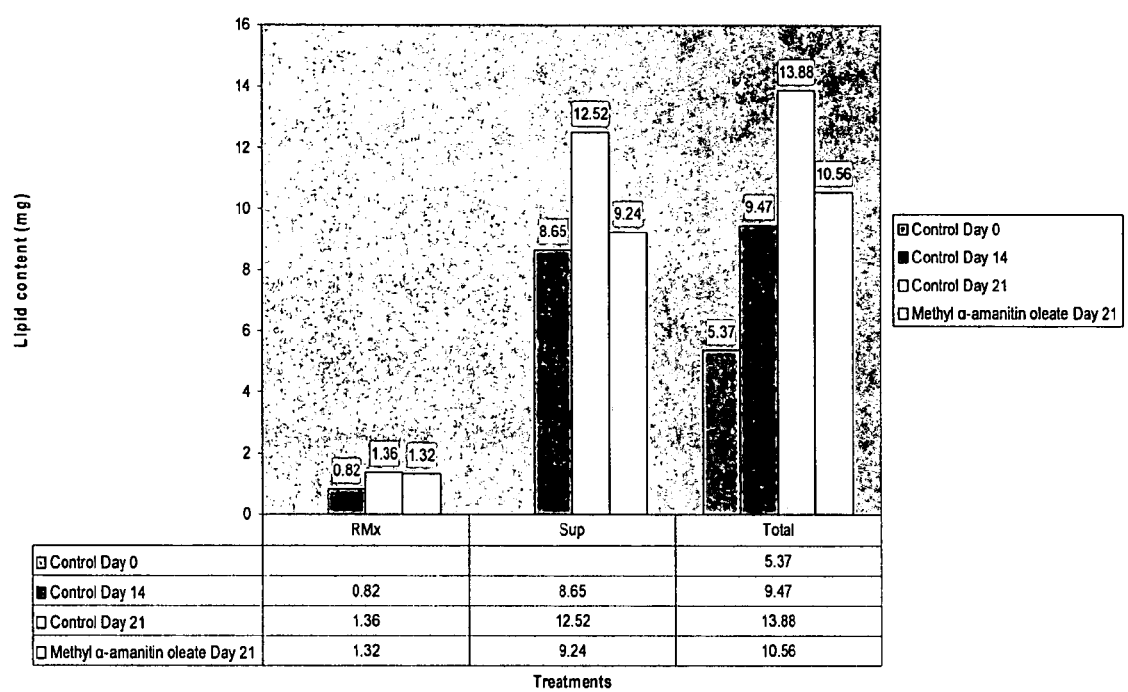

Figure 17. PAGE for Matrix and Media Comparison of Coomasie Stained Protein Bands from 1 μm Filtered to 5 μm Filtered Matrices.
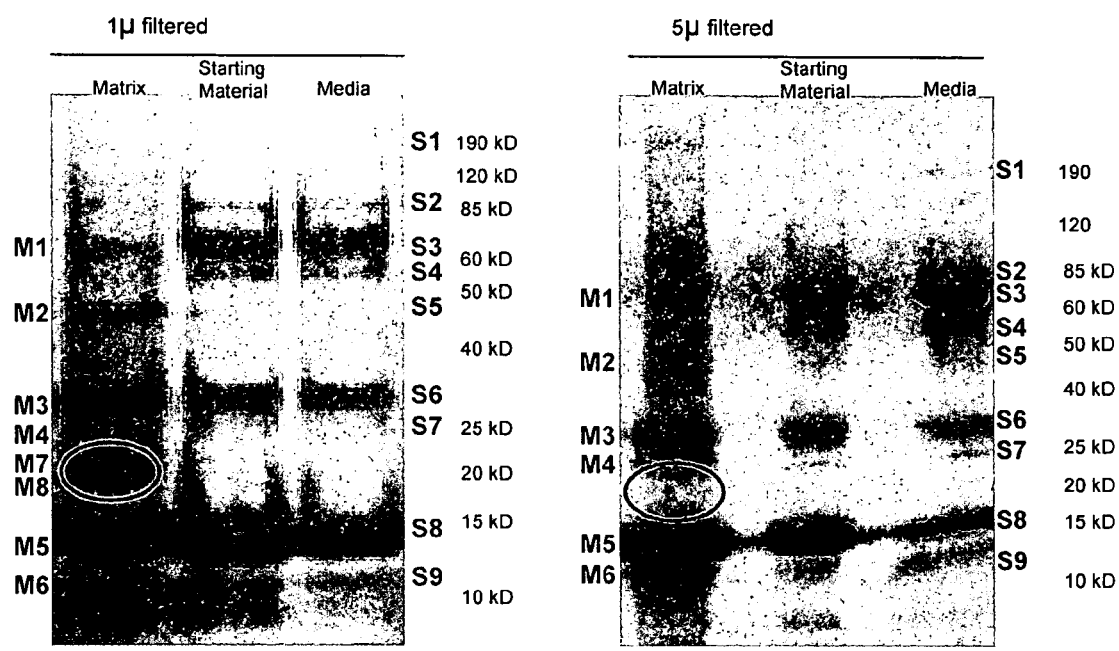

Figure 18. Regeneration Matrix Neuronal Gene Up-regulation Activity.
A. NT-3.
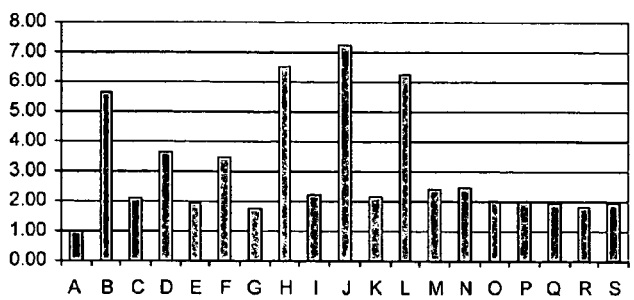
B. NCAM-1.
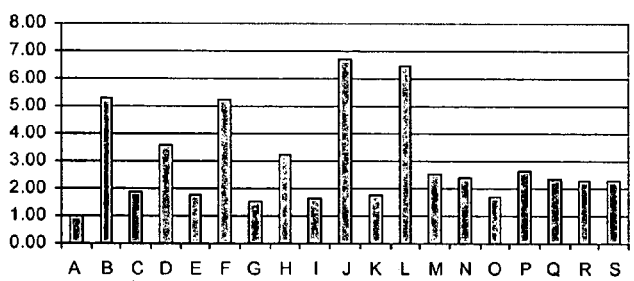
C. GAP-43.
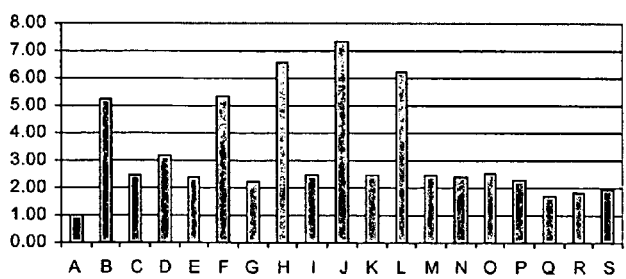

Figure 19. Fold Up-Regulation of Genes Following Incubation of Regeneration Matrix (and Heat Inactivated Regeneration Matrix) with SH-SY5Y Cells.
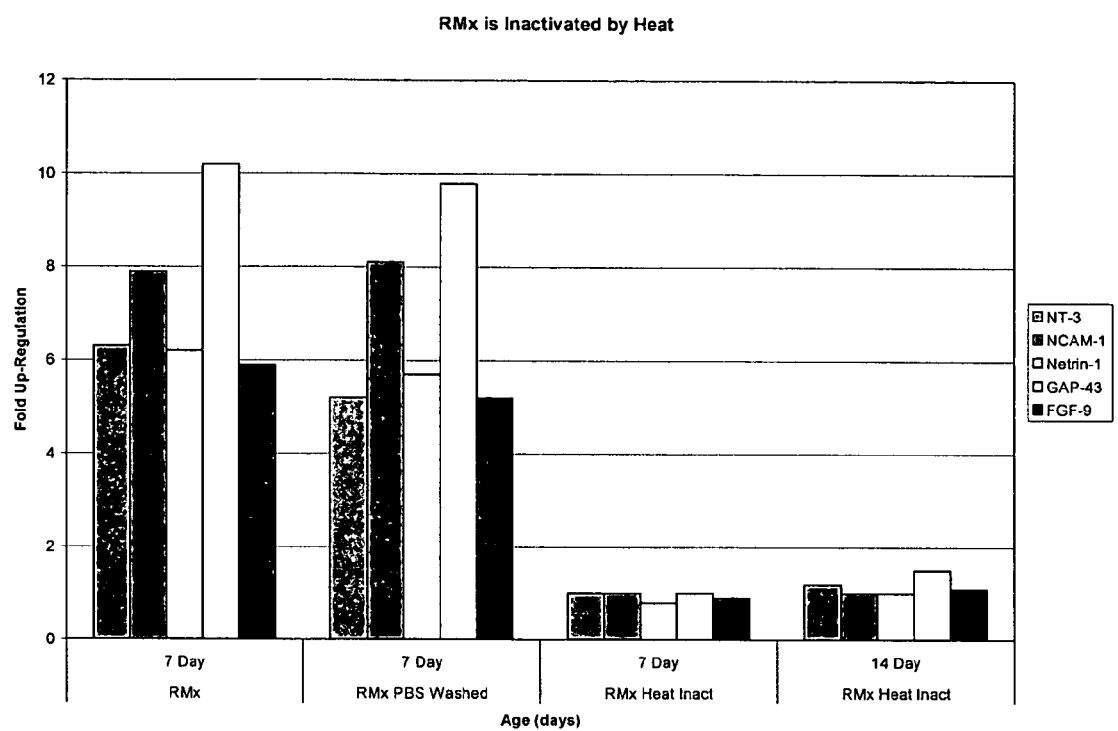

Figure 20. Neurite Extension by Neruoscreen® Cells Treated with Regeneration Matrix.
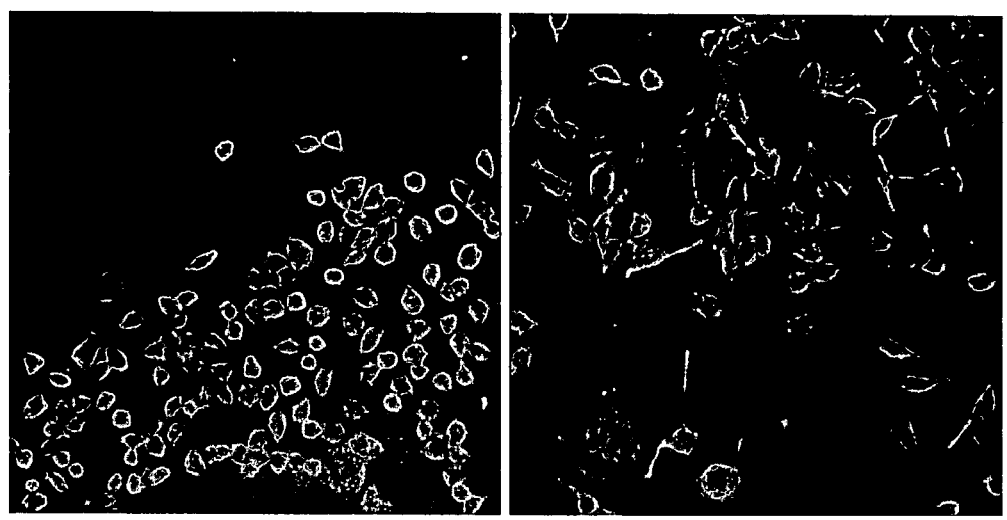

Figure 21. Comparison of Neurite Outgrowth of Neuroscreen® Cells Cultured in the Presence or Absence of Regeneration Matrix.
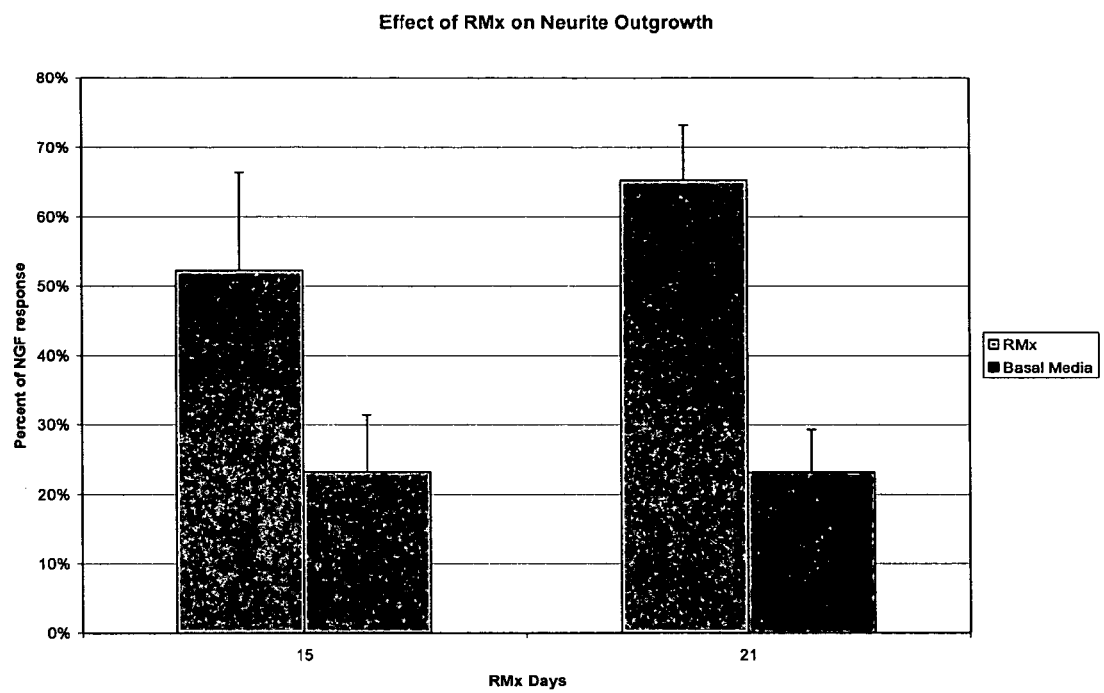

Figure 22. Comparison of Neurite Outgrowth of Neuroscreen® Cells Cultured in the Presence of Regeneration Matrix Produced without Growth Factor Supplementation.
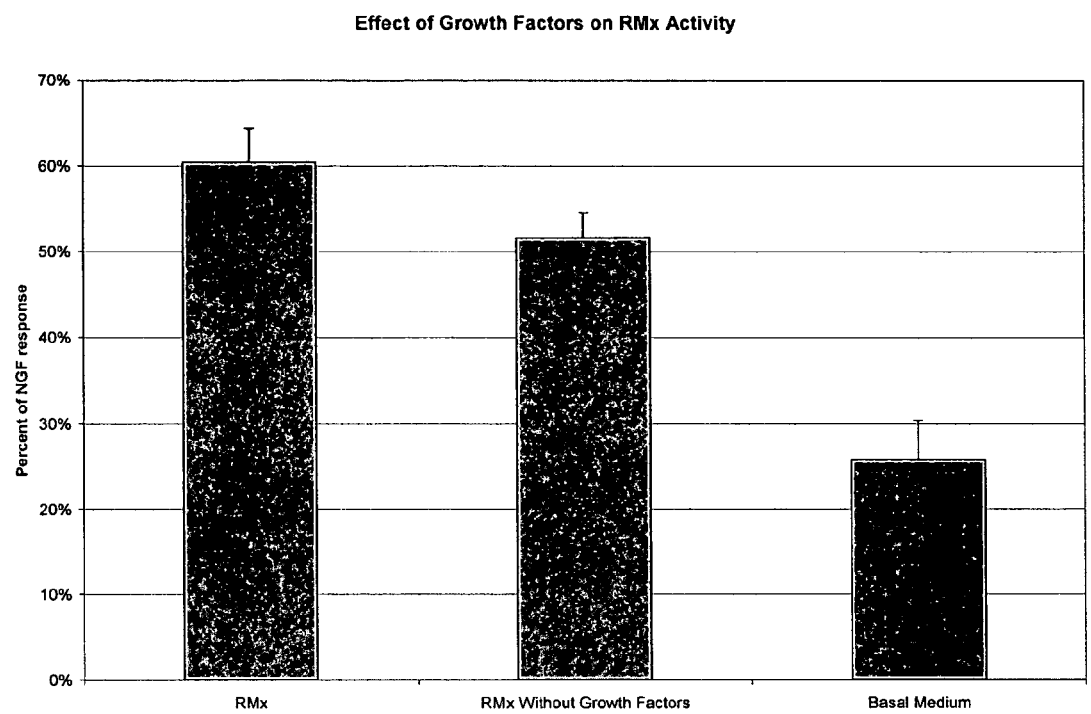

Figure 23. NGF Dose Response.
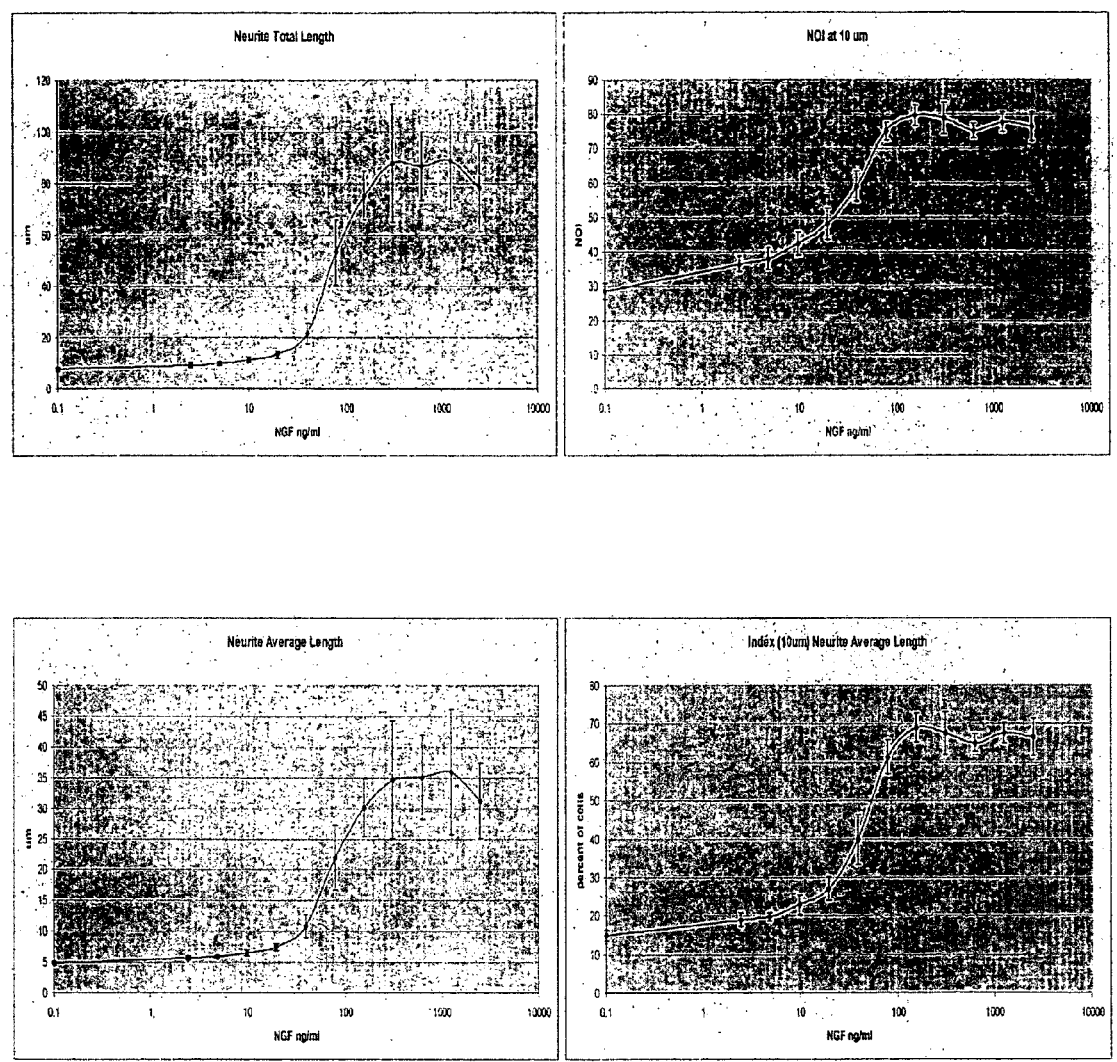

Figure 24. Neurite Total Length.
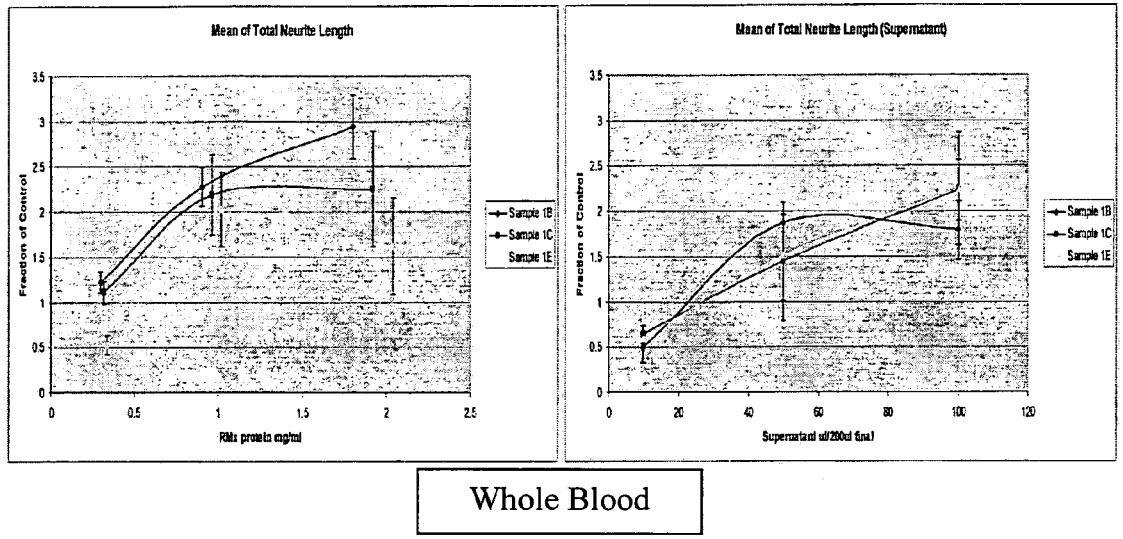
Whole Blood
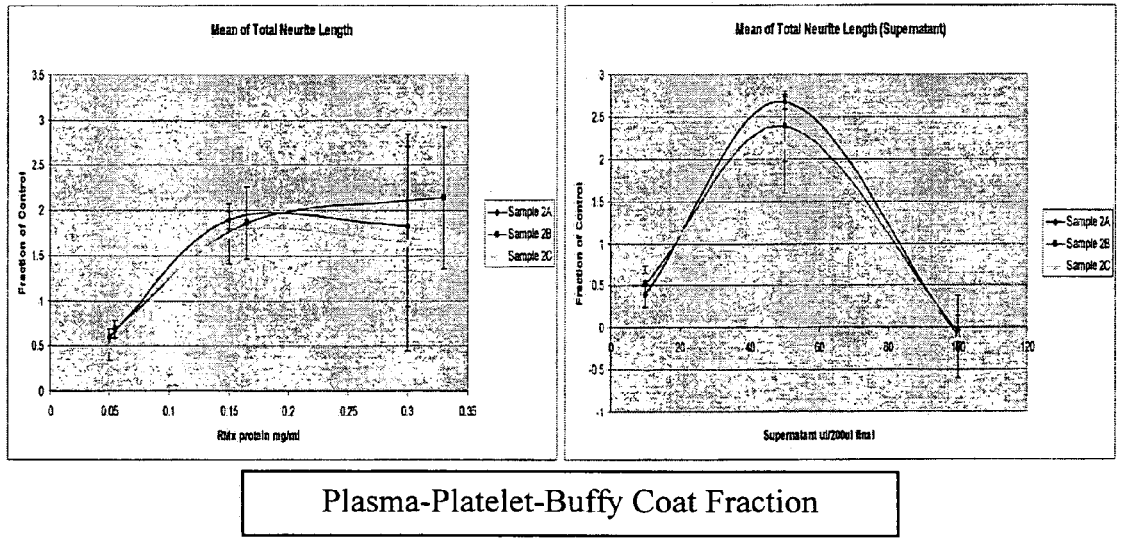
Plasma-Platelet-Buffy Coat Fraction Figure 25. Control Primary Rat Embryonic Spinal Cord Cells, Labeled for Neuronal Tubulin (Tuj1) and Glia (GFAP) Six Days After the Start of Single Cell Suspension Culture (Two Exposures to Show All Stained Components).
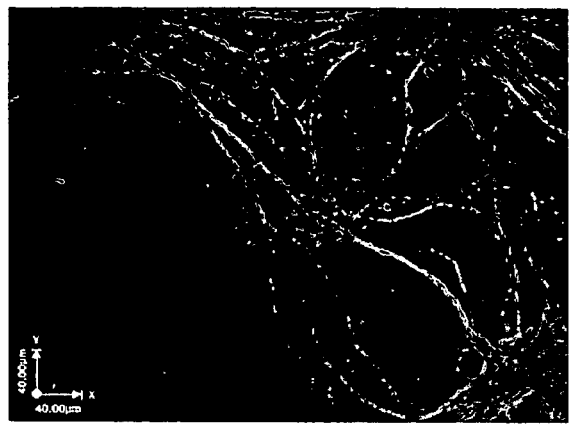
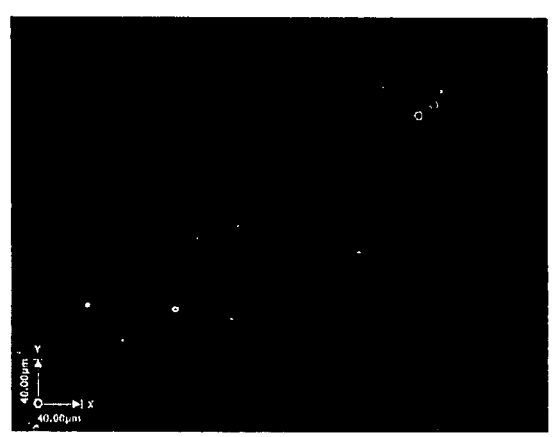
Tuj1-neurons　　　　　　　　　　　　　　GFAP-astrocytes Figure 26. Interaction of Neuronal Cells with Seven Day Regeneration Matrix.
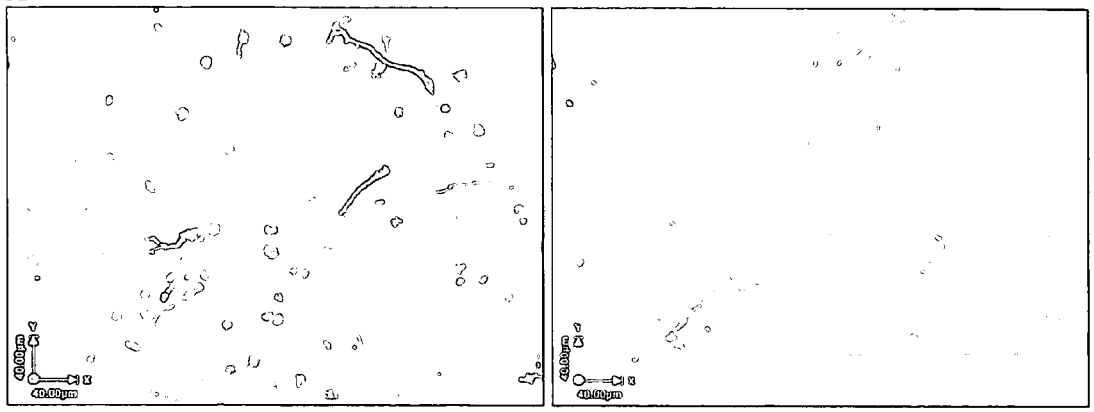
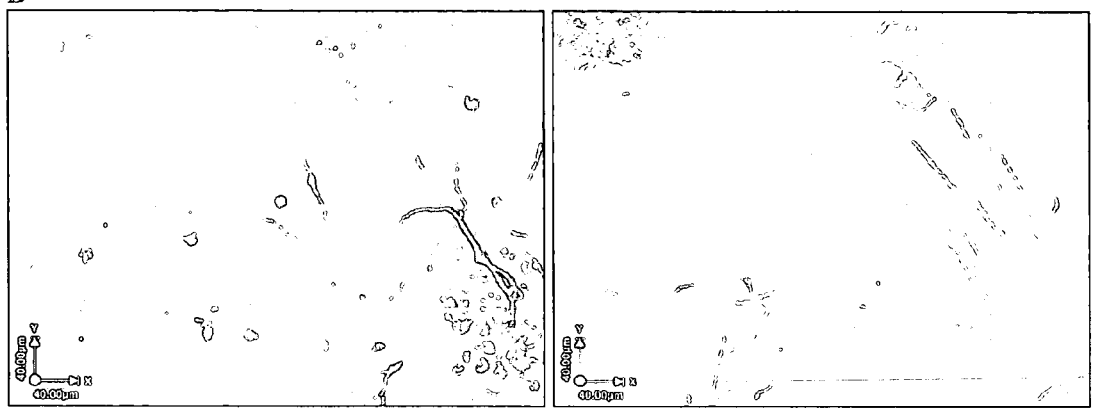
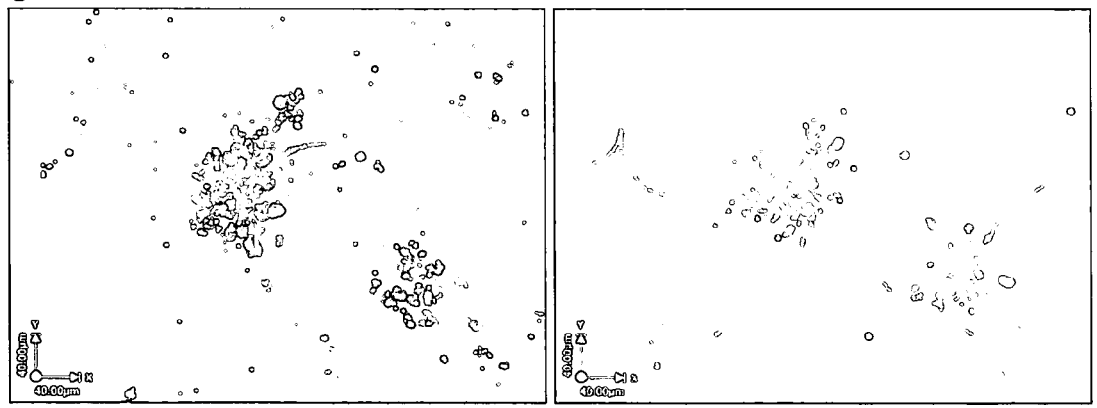
Tuj1-neurons GFAP-astrocytes Figure 27. Immunocytochemistry of Human Fibroblasts Cultured in Regeneration Matrix Production Medium and with Regeneration Matrix.
Regeneration Matrix Medium (Control)
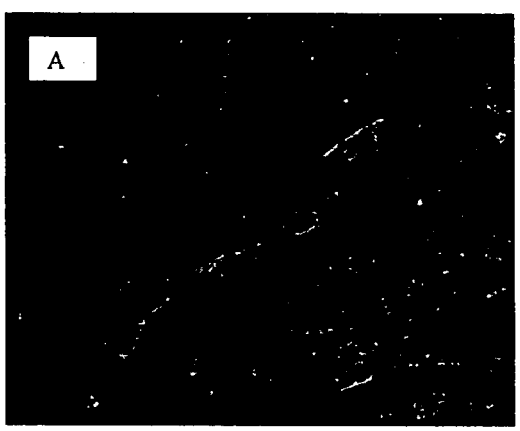 
Regeneration Matrix
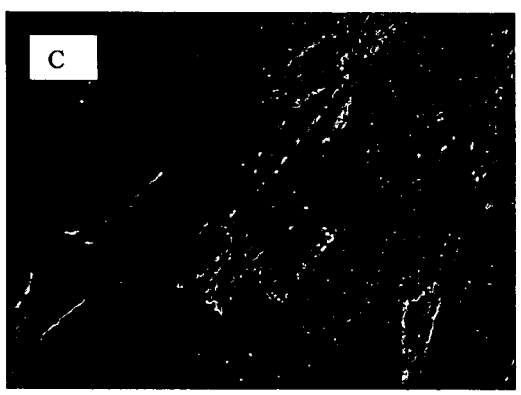 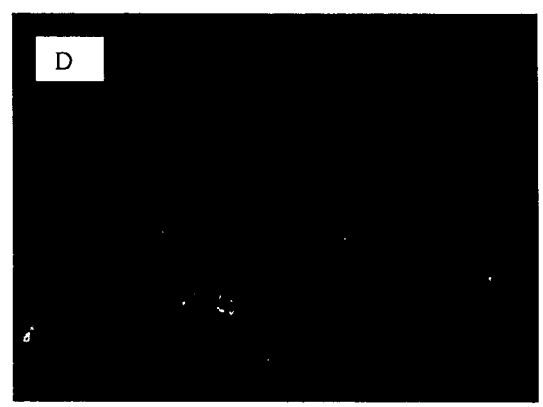
β-Tubulin	F-Actin Figure 28. Effect of Regeneration Matrix on Fibroblast Attachment, Fibroblast Nuclear Area, and % BrdU-positive Fibroblasts.
A.
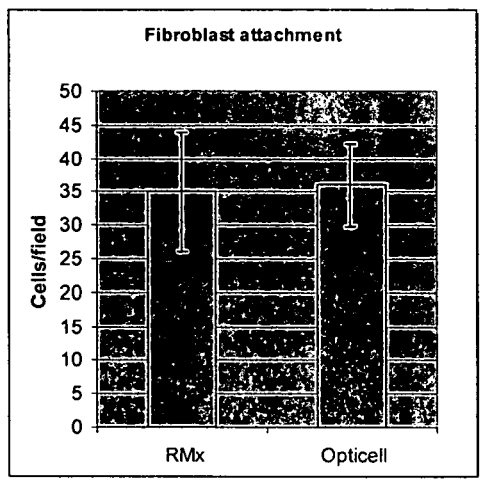
B.
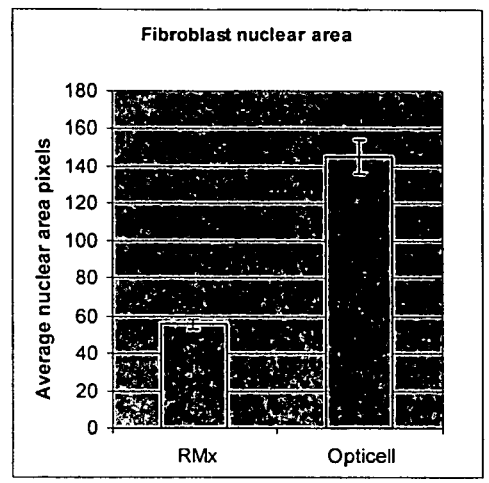
C.
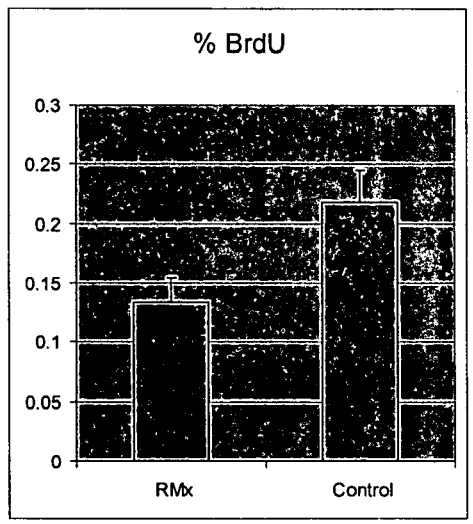

Figure 29. Regeneration Matrix Implantation into Rat Full Transection Model (5 mm) of SCI Induces Motor Function Recovery.
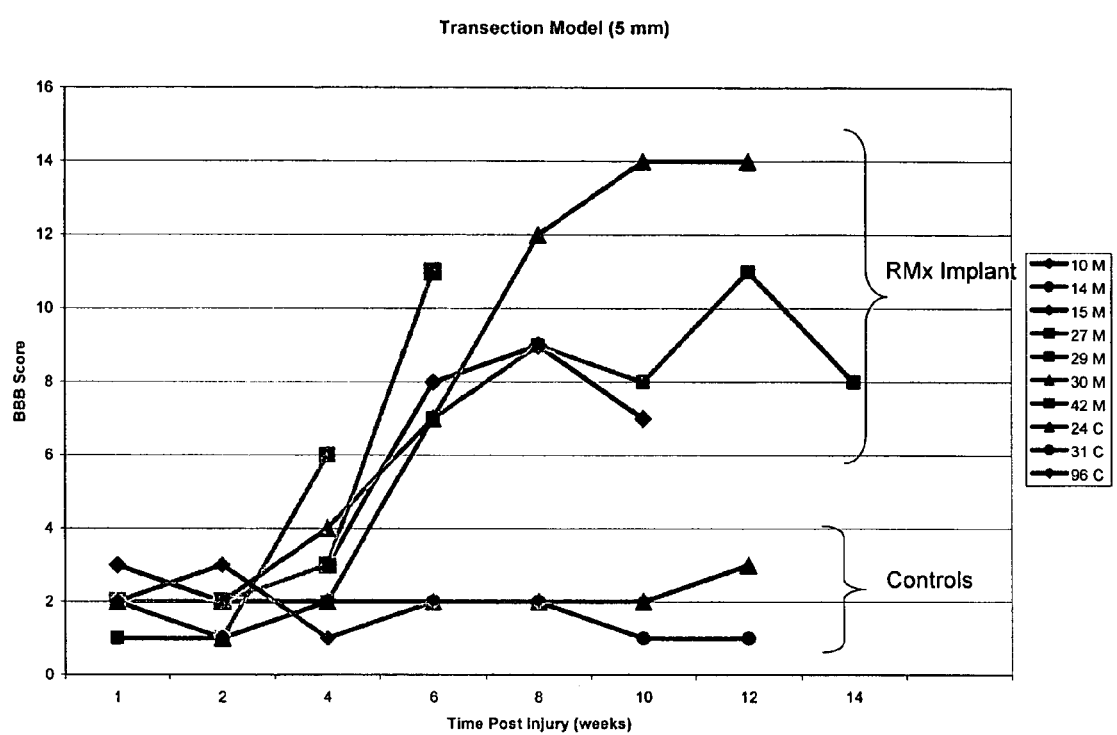

Figure 30. Decreased Incidence of Cyst Formation in Rat Transection Model of Spinal Cord Injury For Rats Receiving a Regeneration Matrix Implant.
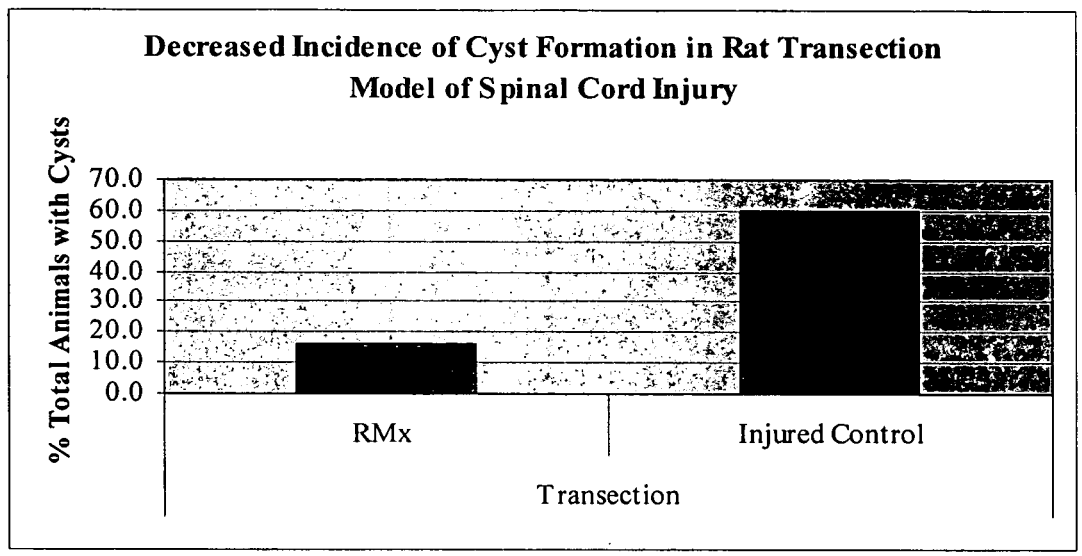

Figure 31. Regeneration Matrix Implantation into Rat Hemisection Model (5 mm) of SCI Induces Motor Function Recovery.
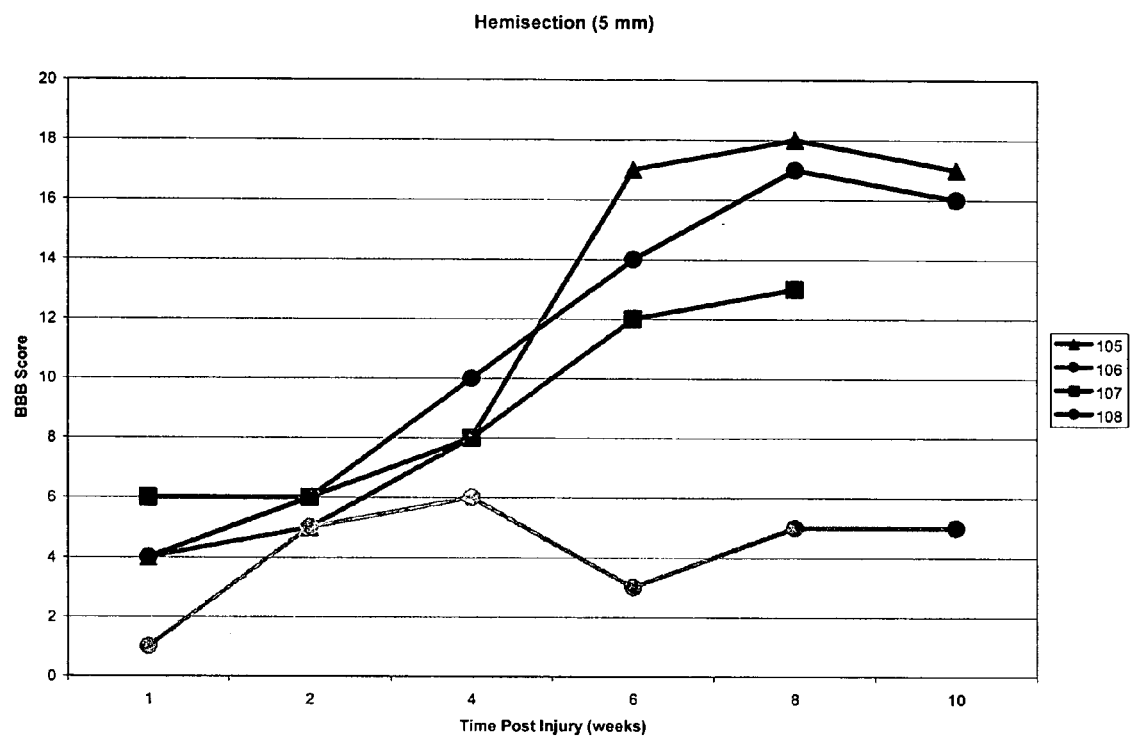

Figure 32A. Functional recovery following RMx implantation into spinal cord of rats that had a 5mm full transection.
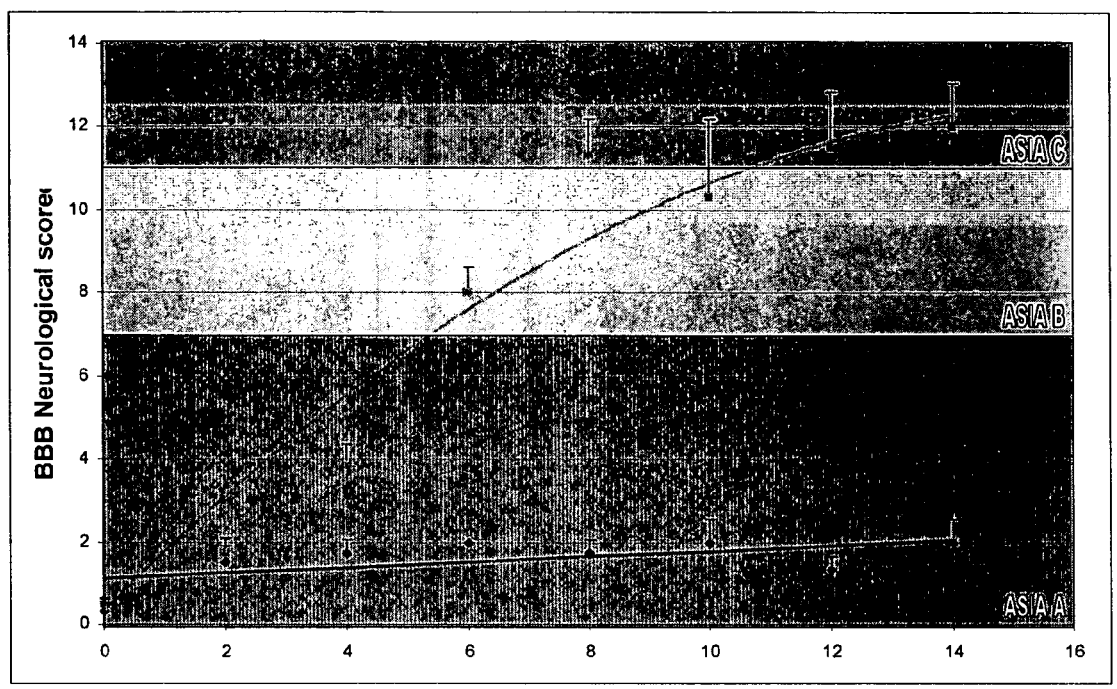

Figure 32B. Functional Recovery Following Regeneration Matrix Implantation into Spinal Cord of Rats 2 Weeks Post Contusion (50mm) Injury.
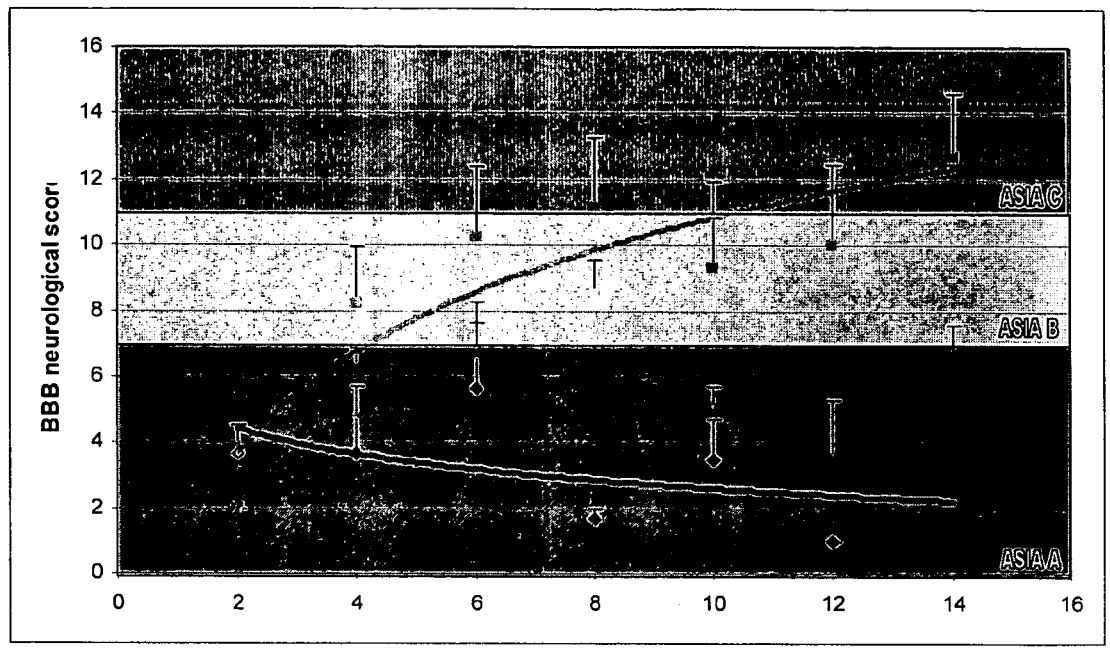

Figure 32C. Combination (Full Transection and Contusion) Model Indicating
Efficacy of a Regeneration Matrix in Treating Spinal Cord Injury.
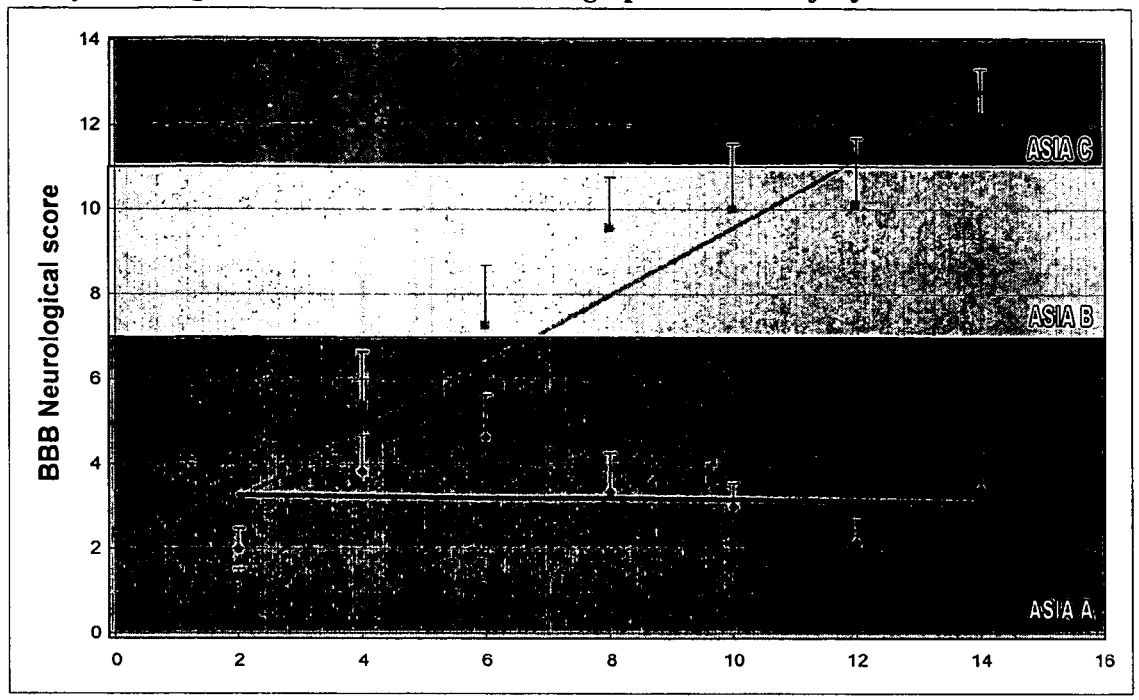

Figure 33. Regeneration Matrix Implantation Induces Motor Function Recovery in Pig Spinal Cord Injuries Caused by Impact and/or Surgical Hemisection (Including Removal of 5 mm of Spinal Cord).
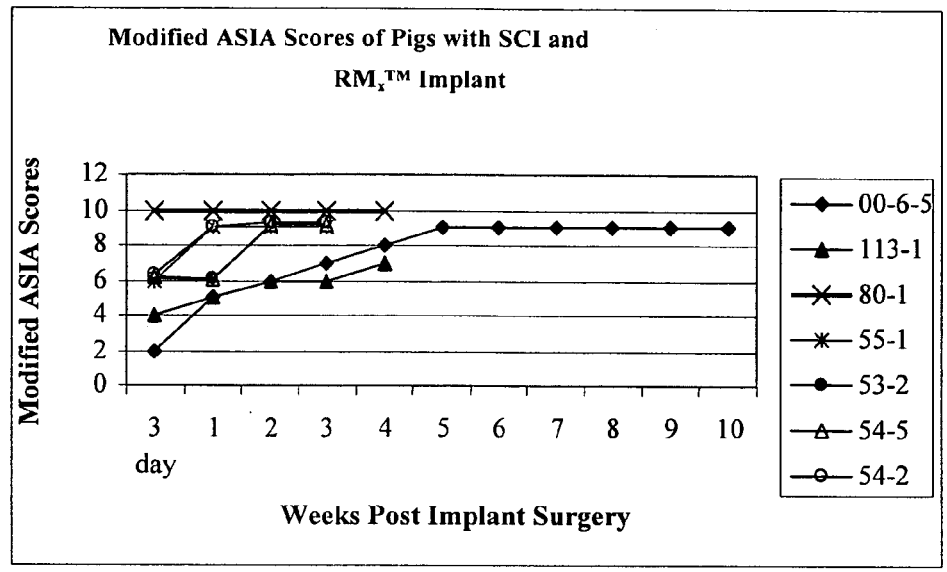
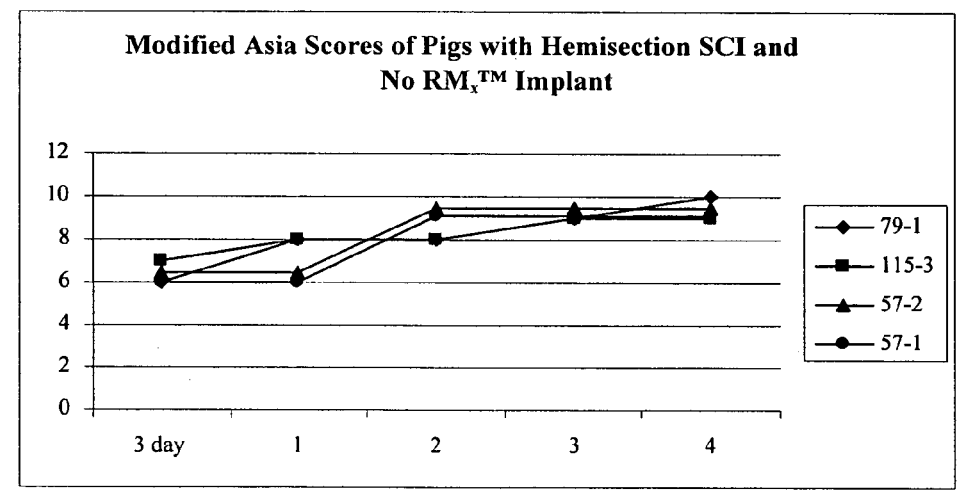

Figure 36. Comparison of Locomotor Recovery in Pigs Treated with Human Regeneration Matrix or Blood Clot at 7 Weeks Post-SCI.
p values calculated using Mann-Whitney U test Figure 37. Newly Forming Neurons (Brown) at Site of Spinal Cord Injury in a Pig at 1 Month Post Regeneration Matrix Implantation, shown at 200x magnification.
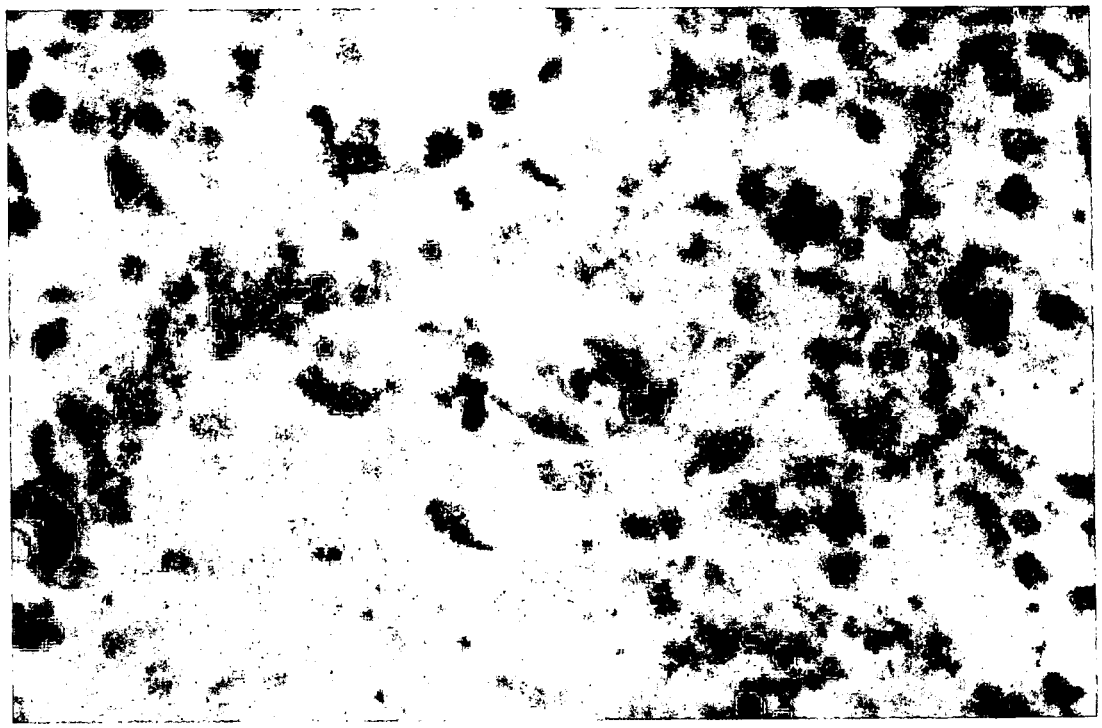

Figure 38. Microscopic Evaluation of a Longitudinal Section from a Rat Spinal Cord Regeneration Study.
A.
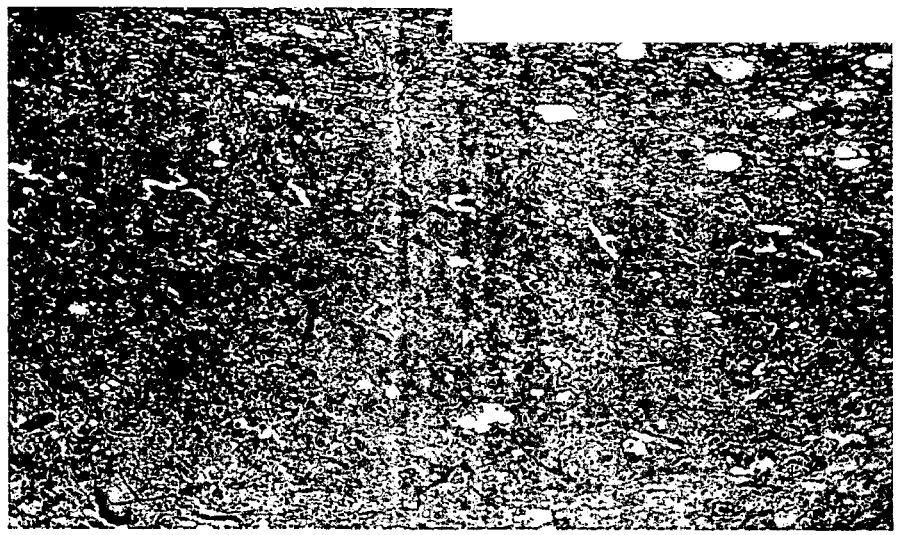
B.

SEQUENCE LISTING

```
<160> NUMBER OF SEQ ID NOS: 16

<210> SEQ ID NO 1
<211> LENGTH: 21
<212> TYPE: DNA
<213> ORGANISM: Artificial
<220> FEATURE:
<223> OTHER INFORMATION: sense primer

<400> SEQUENCE: 1
cctgcaccac caactgctta g                                              21

<210> SEQ ID NO 2
<211> LENGTH: 21
<212> TYPE: DNA
<213> ORGANISM: Artificial
<220> FEATURE:
<223> OTHER INFORMATION: sense primer

<400> SEQUENCE: 2
agaccacctg gtgctcagtg t                                              21

<210> SEQ ID NO 3
<211> LENGTH: 28
<212> TYPE: DNA
<213> ORGANISM: Artificial
<220> FEATURE:
<223> OTHER INFORMATION: sense primer

<400> SEQUENCE: 3
aaagtgcccg gcaggacgag ggtaaaga                                       28

<210> SEQ ID NO 4
<211> LENGTH: 26
<212> TYPE: DNA
<213> ORGANISM: Artificial
<220> FEATURE:
<223> OTHER INFORMATION: sense primer

<400> SEQUENCE: 4
gaaagtggac tccacagggc cacacg                                         26
```

```
<210> SEQ ID NO 5
<211> LENGTH: 31
<212> TYPE: DNA
<213> ORGANISM: Artificial
<220> FEATURE:
<223> OTHER INFORMATION: sense primer

<400> SEQUENCE: 5
aaggagtttg ccagaagact cgctcaattc c                              31

<210> SEQ ID NO 6
<211> LENGTH: 30
<212> TYPE: DNA
<213> ORGANISM: Artificial
<220> FEATURE:
<223> OTHER INFORMATION: sense primer

<400> SEQUENCE: 6
cacgtaatcc tccatgagat acaagggcgg                                30

<210> SEQ ID NO 7
<211> LENGTH: 24
<212> TYPE: DNA
<213> ORGANISM: Artificial
<220> FEATURE:
<223> OTHER INFORMATION: sense primer

<400> SEQUENCE: 7
cccggaccgc tgtggacttg gttg                                      24

<210> SEQ ID NO 8
<211> LENGTH: 25
<212> TYPE: DNA
<213> ORGANISM: Artificial
<220> FEATURE:
<223> OTHER INFORMATION: sense primer

<400> SEQUENCE: 8
gtataagtct caggcccggc cagtc                                     25

<210> SEQ ID NO 9
<211> LENGTH: 21
<212> TYPE: DNA
<213> ORGANISM: Artificial
<220> FEATURE:
<223> OTHER INFORMATION: sense primer

<400> SEQUENCE: 9
gcagtctgcc acttggaagg a                                         21

<210> SEQ ID NO 10
<211> LENGTH: 21
<212> TYPE: DNA
<213> ORGANISM: Artificial
<220> FEATURE:
<223> OTHER INFORMATION: sense primer

<400> SEQUENCE: 10
gccatattgc gtaggcgagg t                                         21

<210> SEQ ID NO 11
<211> LENGTH: 24
<212> TYPE: DNA
<213> ORGANISM: Artificial
<220> FEATURE:
<223> OTHER INFORMATION: sense primer

<400> SEQUENCE: 11
```

```
cacagccatc ccagcaacct tggg                                          24

<210> SEQ ID NO 12
<211> LENGTH: 28
<212> TYPE: DNA
<213> ORGANISM: Artificial
<220> FEATURE:
<223> OTHER INFORMATION: sense primer

<400> SEQUENCE: 12
gggcaaactc cttatgaagt ggcacaaa                                      28

<210> SEQ ID NO 13
<211> LENGTH: 24
<212> TYPE: DNA
<213> ORGANISM: Artificial
<220> FEATURE:
<223> OTHER INFORMATION: sense primer

<400> SEQUENCE: 13
aaatgtcact gacttgggtc tggg                                          24

<210> SEQ ID NO 14
<211> LENGTH: 26
<212> TYPE: DNA
<213> ORGANISM: Artificial
<220> FEATURE:
<223> OTHER INFORMATION: sense primer

<400> SEQUENCE: 14
gacaggtcat catcaaaggc gatggg                                        26

<210> SEQ ID NO 15
<211> LENGTH: 26
<212> TYPE: DNA
<213> ORGANISM: Artificial
<220> FEATURE:
<223> OTHER INFORMATION: sense primer

<400> SEQUENCE: 15
cgcctaatat ctcctgggtt gacacc                                        26

<210> SEQ ID NO 16
<211> LENGTH: 26
<212> TYPE: DNA
<213> ORGANISM: Artificial
<220> FEATURE:
<223> OTHER INFORMATION: sense primer

<400> SEQUENCE: 16
aatgccaaat cggctgtggt ctttcc                                        26
```

ACELLULAR BIOABSORBABLE TISSUE REGENERATION MATRICES

CROSS-REFERENCE TO RELATED APPLICATIONS

This application is co-pending with, shares and least one common inventor with and claims priority to U.S. Provisional Patent Application Ser. No. 60/730,614, filed Oct. 26, 2005, the contents of which are incorporated herein by reference in their entirety.

BACKGROUND

The present invention relates to formulation of a bio-absorbable proteinaceous matrix derived from animal tissue. The invention also relates to the use of this matrix in vivo which functions to induce and facilitate the growth and generation/regeneration of tissue.

With the exception of blood, all other tissues in the body are composed of cells arranged in an integrated structure which requires an extracellular support scaffold or matrix in order to maintain proper growth differentiation and function. The field of tissue engineering aims to provide methods of achieving the complex structure using either artificial or natural polymers with properties that allow cell attachment, growth and pattern formation in order to provide replacement tissues for those lost during injury or disease. The ideal scaffolding material would be non-immunogenic and mimic the natural scaffold support structure found in the body as closely as possible. One of these attributes is that the scaffold be biodegradable to allow for regenerated or restored tissue to reach its ultimate level of homeostasis and function. It is known in the prior art to construct bioabsorbable scaffolds capable of providing support structure for cellular attachments and growth as well as delivery of biologically active chemicals, proteins, and peptides. The most widely used are hydrogels composed of various polymers including polysaccharides. Biodegradable hydrogels produced from biodegradable polysaccharides either alone or in combination with naturally occurring extracellular matrix proteins such as collagen have been employed as vehicles for drug delivery (Cascone, M. G. et al., *Bioartificial polymeric materials based on polysaccharides*, J Biomater. Sci. Polym. Ed. 12, 267-281, 2001; Jeong, B. et al., *Drug release from biodegradable injectable thermosensitive hydrogel of PEG-PLGA-PEG triblock copolymers*, J Control Release 63, 155-163, 2000; Kopecek, J., *Smart and genetically engineered biomaterials and drug delivery systems*, Eur. J. Pharm. Sci. 20, 1-16, 2003; Peppas, N. A. et al., *Hydrogels in pharmaceutical formulations*, Eur. J. Pharm. Biopharm. 50, 27-46, 2000; Zhang, Y., and Chu, C. C., *In vitro release behavior of insulin from biodegradable hybrid hydrogel networks of polysaccharide and synthetic biodegradable polyester*, J. Biomater. Appl. 16, 305-325, 2002) and providing structural support for engineered tissues (Arevalo-Silva, C. A. et al., *Internal support of tissue-engineered cartilage*, Arch. Otolaryngol. Head Neck Surg. 126, 1448-1452, 2000; Desgrandchamps, F., *Biomaterials in functional reconstruction*, Curr. Opin. Urol. 10, 201-206, 2000; Kim, T. K. et al., *Experimental model for cartilage tissue engineering to regenerate the zonal organization of articular cartilage*, Osteoarthritis Cartilage 11, 653-664, 2003; Kojima, K. et al., *A composite tissue-engineered trachea using sheep nasal chondrocyte and epithelial cells*, Faseb J. 17, 823-828, 2003; Marler, J. J. et al., *Soft-tissue augmentation with injectable alginate and syngeneic fibroblasts*, Plast. Reconstr. Surg. 105, 2049-2058, 2000; Saim, A. B. et al., *Engineering autogenous cartilage in the shape of a helix using an injectable hydrogel scaffold*, Laryngoscope 110, 1694-1697, 2000; Thompson, C. A. et al., *Percutaneous transvenous cellular cardiomyoplasty: A novel nonsurgical approach for myocardial cell transplantation*, J. Am. Coll. Cardiol. 41, 1964-1971, 2003; Wake, M. C. et al., *Dynamics of fibrovascular tissue ingrowth in hydrogel foams*, Cell Transplant. 4, 275-279, 1995; Weng, Y. et al., *Tissue-engineered composites of bone and cartilage for mandible condylar reconstruction*, J. Oral Maxillofac. Surg. 59, 185-190, 2001; Zimmermann, U. et al., *Hydrogel-based non-autologous cell and tissue therapy*, Biotechniques 29, 564-572, 574, 576 passim, 2000). Recently, the use of hydrogel scaffold as a bridging structure capable of providing guidance channels for regenerating neural tissue for treatment of spinal cord injury ("SCI") has been reported (Tsai, E. C. et al., *Synthetic hydrogel guidance channels facilitate regeneration of adult rat brainstem motor axons after complete spinal cord transection*, J. Neurotrauma. 21, 789-804, 2004;). The production of an extracellular matrix or scaffolding material from blood or other tissue has been described by Vacanti and Vacanti (Biological Scaffolding Material, U.S. Patent Publication Number 20040137613, filed Oct. 17, 2003). This material is described as being composed substantially of cells, cellular debris and cells remnants. However, this material is not reported to possess a biological functionality that facilitates wound repair or regeneration and furthermore requires viable cells or other structures with cell-like properties (Vacanti, M. P. et al., *Identification and initial characterization of spore-like cells in adult mammals*, J. Cell Biochem. 80, 455-460, 2001). Notwithstanding these achievements, there remains a need for a non-immunogenic (or reduced-immunogenic) scaffolding material that further possesses cellular attachment, growth promoting properties, and supports or stimulates regenerative/restorative properties of uninjured tissues surrounding would sites.

SUMMARY OF THE INVENTION

In certain embodiments, the present invention provides methods for producing a bioabsorbable structure that has biological regenerative properties (referred to hereafter as a "regeneration matrix"). Such a regeneration matrix may be produced from any animal tissue including, but not limited to, blood, liver, kidney, muscle, heart, pancreas, olfactory mucosa, bone marrow, cerebrospinal fluid, lymph, and combinations thereof. In certain embodiments, a regeneration matrix is produced by processing either clotted blood or blood collected with anticoagulant. In certain embodiments, a regeneration matrix is produced from a tissue sample from which cells have first been removed. A regeneration matrix may be derived from a subject's own tissue, thus enabling an autologous application, or may be tissue type matched to enable allogenic applications. In certain embodiments, a regeneration matrix is derived from a xenogenic tissue. Xenogenic applications have utility in research settings, but typically do not represent a therapeutic modality for human beings or veterinary applications. In certain embodiments, a regeneration matrix is produced from blood, for example, from a subject's own blood.

A regeneration matrix produced according to certain methods of the present invention has therapeutic properties in that it is able to initiate, increase, support, and/or direct tissue regeneration at a site of tissue damage, loss, and/or degeneration such that surrounding tissue regenerates normal functional tissue. In certain embodiments, the present invention provides methods of administering a regeneration matrix to a subject, wherein the regeneration matrix initiates and/or increases tissue regeneration. In certain embodiments, damaged tissue to be regenerated according to methods of the present invention includes, but is not limited to, nerve tissue, muscle tissue, liver tissue, heart tissue, lung tissue, and/or skin tissue. For example, in certain embodiments, the invention provides methods for harnessing the natural regenerative components of blood and/or blood clots and engineering them into a regeneration matrix that can be delivered to a wound site at an appropriate time to maximize the regeneration response while minimizing production of non-functional scar formation.

In certain embodiments, a regeneration matrix has neuro-regeneration properties that are useful to treat conditions that result in the damage, loss and/or degeneration of nerve tissue. In certain embodiments, nerve tissue to be regenerated comprises nerve tissue from the central nervous system ("CNS"). In certain embodiments, CNS tissue is lost as a result of a disease and/or or injury, such as, for example, spinal cord injury, spinal cord cancer, amyotrophic lateral sclerosis, Parkinson's disease, Alzheimer's disease, stroke, and/or multiple sclerosis. The regeneration activity of a regeneration matrix may be enhanced or supplemented by the addition of one or more therapeutic agents including, but not limited to, proteins, peptides, drugs, cytokines, extracellular matrix molecules, and/or growth factors. In certain embodiments, one or more therapeutic effects of a therapeutic agent are increased when administered in a regeneration matrix.

In certain embodiments, the present invention provides a regeneration matrix comprising a bioabsorbable structure that has tissue regenerative properties. In certain embodiments, such a regeneration matrix includes one or more proteins. For example, such a regeneration matrix may contain one or more of: transferrin, serum albumin, serum albumin precursor, complement component 3, chains A-D hemoglobin, IgM, IgG1, medullasin inhibitor 2, carbonic anhydrase, and/or CA 1 protein. In certain embodiments, a regeneration matrix lacks substantial metabolic activity.

In certain embodiments a regeneration matrix of the present invention is supplemented with one or more therapeutic agents including, but not limited to, proteins, peptides, drugs, cytokines, extracellular matrix molecules, and growth factors. In certain embodiments, one or more therapeutic effects of a therapeutic agent are increased when administered in a regeneration matrix. In certain embodiments, a regeneration matrix may be seeded or mixed with cells including, but not limited to, stem cells, progenitor cells, nerve cells and/or glial cells.

In certain embodiments, the present invention provides a bioabsorbable tissue regeneration matrix for inducing regeneration of functional tissue at a site of application in a subject. In certain embodiments, a regeneration matrix promotes autoregeneration of tissue at the site of application. In certain embodiments, a regeneration matrix increases biological activity of surrounding tissue. In certain embodiments, a regeneration matrix is in solid or semi-solid form. For example, a regeneration matrix can be in the form of a three-dimensional matrix. In certain embodiments, a regeneration matrix is in the form of a suspension.

BRIEF DESCRIPTION OF THE DRAWINGS

The foregoing features of the invention will be more readily understood by reference to the following detailed description, taken with reference to the accompanying drawings. In the drawings, "RMx" refers to a regeneration matrix.

FIGS. 1A, 1B and 1C show transdifferention of macrophages into Von Willebrand factor-positive endothelial-like cells. 2A: Macrophages (light staining) and Von Willebrand factor(+) (dark staining) cells at site of spinal cord injury and regeneration matrix implantation at 2 weeks post-implantation in a pig. Double staining shows up as black color. Shown at 200× magnification. 2B: Black staining=macrophages (light staining) expressing Von Willebrand factor, shown at 400× magnification. 2C: Macrophages expressing Von Willebrand factor are forming a blood vessel, shown at 400× magnification.

FIGS. 2A, 2B, 2C and 2D show the effect of regeneration matrix treatment on rat spinal cord tissue. A shows healthy rat spinal cord in the absence of a regeneration matrix with healthy blood vessels indicated. B shows damaged rat spinal cord where little CNS tissue is evident and no healthy blood vessels are present. C shows view of damaged rat spinal cord treated with a regeneration matrix, where regenerated healthy CNS tissue and cross-sections of blood vessels are evident. D is another view of the damaged spinal cord tissue of C, showing regenerated CNS tissue and a longitudinal section of healthy blood vessels.

FIG. 3 is a photograph of a regeneration matrix produced using non-clotted blood and 1.2 μm final filtration contained with the Opticell® production cassette.

FIG. 4 shows a paraffin section of 3-week old regeneration matrix made from whole human blood. The regeneration matrix does not show any indication of intact cells or nuclei. Hematoxylin staining was completely negative in all section analyzed but the material stains strongly with eosin. A beaded structure can be clearly resolved when using high numerical aperture lenses (high resolution). Besides the beaded structure which comprises most of the RMx, it is possible to observe small regions of flat sheets that seem to be composed by a more compact structure.

FIGS. 5A, 5B, 5C, and 5D show scanning electron micrographs of a regeneration matrix produced using clotted blood and 5 μm final filtration. A—200×, B—1000×, C—7500×, D—7500×.

FIGS. 6A, 6B, 6C and 6D show scanning electron micrographs of a regeneration matrix produced using clotted blood and 1.2 μm final filtration (21 days). A—200×, B—1000×, C—7500×, D—7500×.

FIGS. 7A, 7B, 7C, and 7D show scanning electron micrographs of a regeneration matrix produced using non-clotted (using EDTA) blood and 1.2 μm final filtration (21 days). A—200×, B—1500×, C—5000×, D—10000×.

FIG. 8 shows a Light Micrograph of a regeneration matrix produced using non-clotted blood and 1.2 μm final filtration (100× magnification).

FIG. 9 shows transmission electron microsopy (TEM) of a 21 day old regeneration matrix prepared from a tissue sample passed through a 5 μm filter. It is evident in this TEM that the rounded spheres seen in the scanning electron micrographs (FIGS. 5-7) are part of a much bigger and relatively homogensous structure or aggregate of these spheres. There is not evidence of nuclei.

FIG. 10 shows transmission electron microsopy of an 8-week old regeneration matrix made from whole human blood. The regeneration matrix stained homogeneously and the outside surface of each aggregate had less small protruding spheres than a 3-week old regeneration matrix (see FIG. 9) and was somewhat honeycomb-shaped (the most effective arrangement method for particles). Many new aggregates of regeneration matrix formed along long strings of regeneration matrix material.

FIG. 11 shows transmission electron microsopy of an 8-week old regeneration matrix made from whole human blood. The regeneration matrix stained homogeneously and the outside surface of each aggregate had less small protruding spheres than a 3-week old regeneration matrix (see FIG. 9) and was somewhat honeycomb-shaped (the most effective arrangement method for particles).

FIGS. 12A and 12B show SDS-PAGE analysis of a regeneration matrix from 5 different batches. Total protein in the regeneration matrix on days 15 (A) and 21 (B) was stained with Coomassie blue. Major protein species are numbered 1-6 and presented in respective densitometry graphs. Molecular weight standards (KDa) are indicated on the left side of the gels.

FIG. 13 shows total RNA content (μg) in regeneration matrix and supernatant of 21-day cultures (5 μm filtered) that formed in the presence of α-amanitin (RNA II polymerase inhibitor), aphidicolin (DNA polymerase inhibitor), or cyclohexamide (protein synthesis inhibitor) versus controls.

FIG. 14 shows total protein content in regeneration matrix and supernatant of 21-day cultures (5 μm filtered) that formed in the presence of α-amanitin (RNA II polymerase inhibitor), aphidicolin (DNA polymerase inhibitor), or cyclohexamide (protein synthesis inhibitor) versus control.

FIG. 15 shows total protein content in regeneration matrix and supernatant of 21-day cultures (1 μm filtered) that formed in the presence of α-amanitin (RNA II polymerase inhibitor) versus control.

FIG. 16 shows total lipid content in regeneration matrix and supernatant of 21-day cultures (1 μm filtered) that formed in the presence of α-amanitin (RNA II polymerase inhibitor) versus control.

FIG. 17 shows PAGE for matrix and media comparison of coomasie stained protein bands from 1 μm filtered to 5 μm filtered matrices.

FIG. 18 shows the effect of regeneration matrices (and their associated supernatant, separately) produced in process media with different supplements on the up-regulation of neuronal genes. A: NT-3, B: NCAM-1, C: GAP-43.

FIG. 19 shows the fold up-regulation of genes caused by regeneration matrix and heat-inactivated regeneration matrix on SH-SY5Y cells. SH-SY5Y cells were incubated with regeneration matrix for 3 hrs and then analyzed for GAPDH, NT-3, NT-6, NCAM-1, FGF-9, GDNF, Netrin-1, and GAP-43, gene expression using RT-PCR. A regeneration matrix washed in PBS 3 times had activity similar to unwashed regeneration matrix. A regeneration matrix that had been incubated at 60° C. for 30 min had no gene up-regulation activity.

FIG. 20 shows neurite extension by Neruoscreen® Cells Treated with a regeneration matrix. Left panel shows a representative field of Neuroscreen® cells growing in basal medium. Right panel shows a representative field of cells treated with a regeneration matrix. Cell nuclei are stained blue and tubulin is stained green.

FIG. 21 shows a comparison of neurite outgrowth of Neuroscreen® cells cultured in the presence or absence of a regeneration matrix. Results are expressed as the percentage of the neurite outgrowth index of NGF treated cells. The results are the mean of 4 independent experiments done in quadruplicate. Error bars show the standard deviation of the mean. Values of regeneration matrices treated and not treated cells are different with P values for the difference below 0.01 (t test).

FIG. 22 shows a comparison of neurite outgrowth of Neuroscreen® cells cultured in the presence of a regeneration matrix produced with and without EGF and bFGF growth factor supplementation. Results are expressed as the percentage of the neurite outgrowth index of NGF treated cells. The results are the mean of at least six replicate samples. The error bars indicate the standard deviation of the mean. All values are different from each other with a P value below 0.01 (t-test).

FIG. 23 shows NGF dose response curves of different concentrations of NGF on the neurite outgrowth of Neuroscreen® cells.

FIG. 24 shows the fold increase (fraction) over the positive NGF control (FIG. 23; 100 ng/ml NGF) on the mean of total length of neurite outgrowth when regeneration matrices produced in TR-10 process media are applied. The regeneration matrices were produced from either whole blood or from the plasma-platelet-buffy coat fraction.

FIG. 25 shows control primary rat embryonic spinal cord cells, labeled for neuronal tubulin (Tuj1) and glia (GFAP) six days after the start of single cell suspension culture (two exposures to show all stained components). On average, 4.2% of cells were Tuj-1 positive and 0.4% of cells were GFAP positive. 100× magnification.

FIG. 26 shows the effect of regeneration matrix on primary rat embryonic spinal cord cells, labeled for neuronal tubulin (Tuj1) and glia (GFAP) six days after the start of single cell suspension culture (two exposures to show all stained components). On average, 55% of cells were Tuj-1 positive and 92% of cells were GFAP positive. Double positive (Tuj-1 & GFAP positive) cells are indicative of triphasic neuroprogenitor cells. 100× magnification.

FIGS. 27A, 27B, 27C and 27D show immunocytochemistry staining for α-tubulin (A) and F-actin (B) of human fibroblasts cultured for 5 days on a regeneration matrix (C & D) versus control (A & B). The medium used in the control cultures was the process medium used to produce the regeneration matrix. The human fibroblasts cultured in contact with the regeneration matrix were significantly less confluent (and appeared to be undergoing apoptosis) compared to control cultures.

FIG. 28 shows the effect of regeneration matrix on fibroblast attachment, fibroblast nuclear area, and % BrdU-positive fibroblasts in 2-day cultures versus control.

FIG. 29 shows regeneration matrix implantation into rat full transection model (5 mm) of SCI induces motor function recovery. Locomotor function recovery results as measured by BBB score were recorded every 2 weeks post injury and regeneration matrix implant. BBB score for individual animals (regeneration matrix—M and controls—C).

FIG. 30 shows decreased incidence of cyst formation in rat transection model of spinal cord injury for rats receiving a regeneration matrix implant. Regeneration matrix implanted animals (n=19) had a 15.8% incidence rate of cyst formation at and around the site of SCI, while the control animals (n=5) had a 60% incidence rate of cyst formation around the site of SCI.

FIG. 31 shows regeneration matrix implantation into rat hemisection model (5 mm) of SCI induces motor function recovery. Locomotor function recovery results as measured by BBB scores were recorded every 2 weeks post injury and regeneration matrix implant. BBB score for individual animals receiving a regeneration matrix implant. Non-implanted controls did not survive to the first evaluation time point.

FIG. 32A: Functional recovery following regeneration matrix implantation into spinal cord of rats that had a 5 mm full transection. FIG. 32B: Functional recovery following a regeneration matrix implantation into spinal cord of rats 2 weeks post contusion (50 mm) injury. Empty control rats did not have second surgery at 2-weeks post contusion. FIG. 32C:

Combination (full transection and contusion) model indicating efficacy of a regeneration matrix in treating spinal cord injury. Control animals include empty controls and biologically inactivated regeneration matrix controls from both injury models. For each of FIGS. 32A, 32B, and 32C, the top line represents data from regeneration matrix implanted animals, while the bottom line represents data from control animals.

FIG. 33 shows that regeneration matrix implantation induces motor function recovery in pig spinal cord injuries caused by impact and/or surgical hemisection (including removal of 5 mm of spinal cord). Pigs 00-6-5 and 113-1 received severe impact injuries resulting in tearing and tissue loss of spinal cord. Pig 80-1 received penetration injury by 14 gauge needle. Pigs 55-1, 53-2, 54-5 and 54-2, as well as all control pigs, received surgical right-side hemisection (5 mm length of right-side of spinal cord removed). Locomotor function recovery results as measured by modified numerical ASIA scores were recorded every week post injury and regeneration matrix implant.

Figure 34:
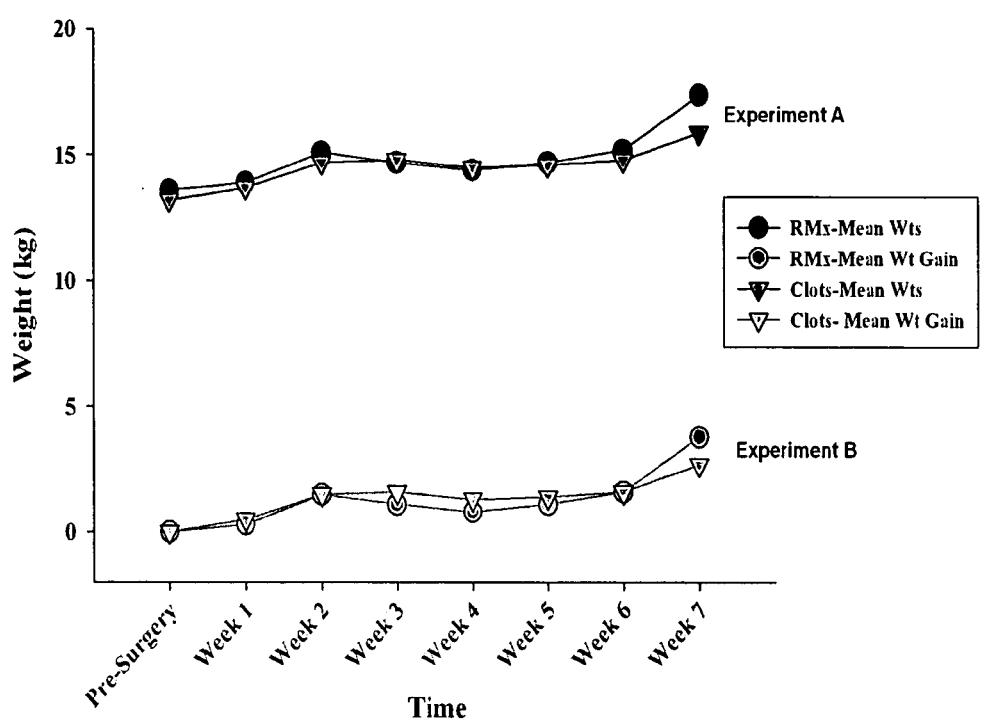

FIG. 34 shows a comparison of mean weights and mean weight gains over 7 weeks in pigs implanted with regeneration matrix or with homogenized blood clots.

Figure 35:
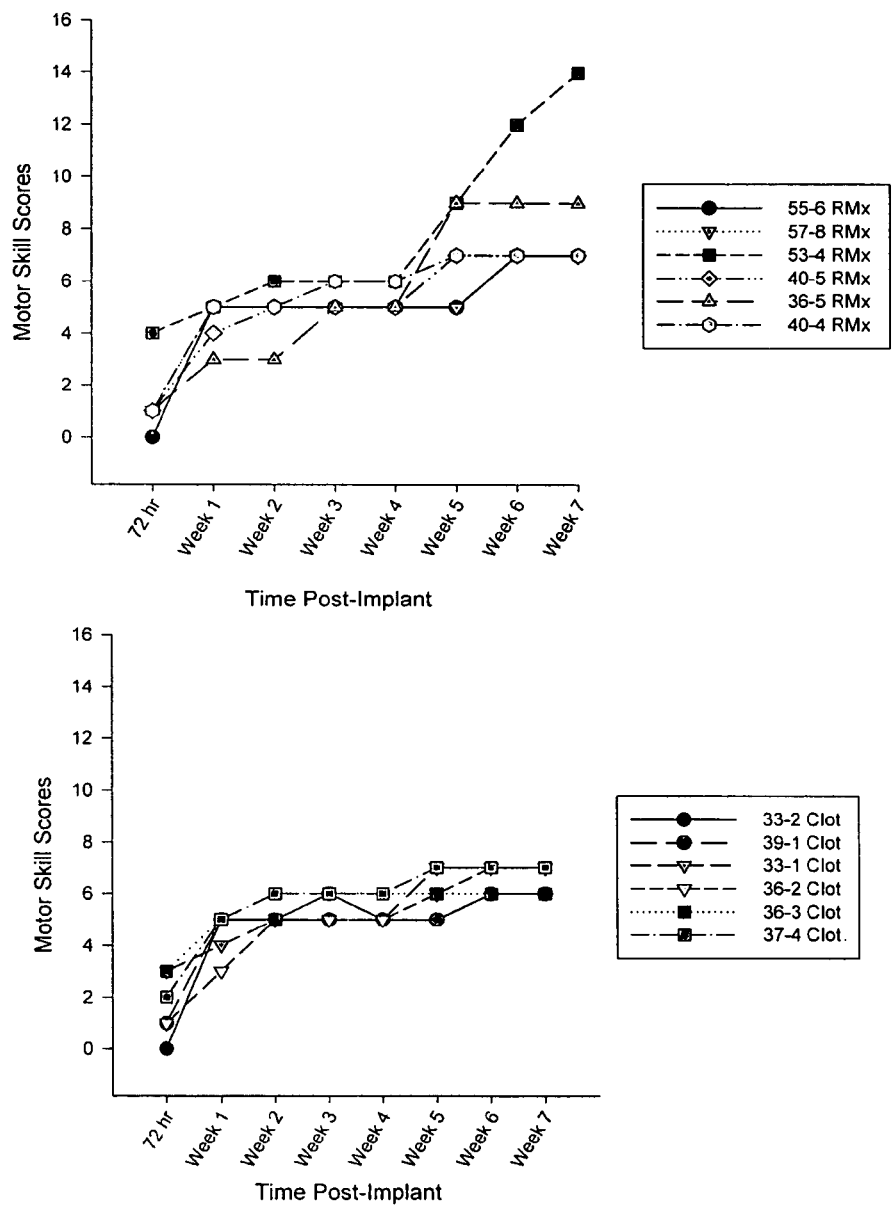

FIG. 35 shows a comparison of right side motor skill recoveries over 7 weeks in pigs implanted with regeneration matrix or human blood clot after right-side hemisection (5 mm length of right-side of spinal cord removed) spinal cord injuries.

FIG. 36 shows a comparison of locomotor recovery in pigs treated with human regeneration matrix or blood clot at 7 weeks post-SCI. The uninjured left side (served as an internal control) was the same in both groups, while the injured right side recovered significantly more (p=0.03) with the regeneration matrix than with the blood clot.

FIG. 37 shows newly forming neurons (brown) at site of spinal cord injury (and spinal cord removal) in a pig at 1 month post regeneration matrix implantation. Light color=nuclei of cells. Dark color=Tuj-1 positive cells. Black color=double staining. Magnification is 200×.

FIG. 38 shows microscopic evaluation of a longitudinal section from a rat spinal cord regeneration study. 38A: Primitive cells associated with the regeneration matrix are filling in the spinal cord defect. Taken at 10× magnification. 38B: Primitive cells at the site of new neural tissue formation 10 days after the regeneration matrix was implanted into a 10 mm spinal cord defect. Taken at 40× magnification.

DETAILED DESCRIPTION OF CERTAIN EMBODIMENTS

Definitions

"Acellular sample": The term "acellular sample" as used herein refers to a biological sample generated by removing cells from an isolated tissue sample. In certain embodiments, an acellular sample is used to generate an acellular bioabsorbable tissue regeneration matrix. An acellular sample can be generated from any of a variety of tissue sample types. For example, an acellular sample may be generated from any of the four basic animal tissue types (muscle tissue, connective tissue, epithelial tissue, and nerve tissue), any of the three basic plant tissue types (ground tissue, dermal tissue, and vascular tissue), any of a variety of other specific tissue types (e.g., blood or liver tissue), and/or from any combination of these or other tissue types. In certain embodiments, an acellular sample is generated from placental tissue, from tissue of the umbilical cord, and/or from tissue of one or more of the following organ systems: cardiovascular, digestive, endocrine, excretory, immune, integumentary, lymphatic, muscular, nervous, reproductive, respiratory, and/or skeletal. One of ordinary skill in the art will be aware of other tissue types from which an acellular sample may be generated. In certain embodiments, an acellular sample is generated from a tissue sample comprising two or more distinct tissue types. In certain embodiments, an acellular sample is generated by passing a tissue sample through a filter with a filtration diameter small enough to exclude cells from passing through such a filter. In certain embodiments, an acellular sample is generated by subjecting a tissue sample to centrifugation and using the supernatant. One of ordinary skill in the art will be aware of other methods useful for removing cells from a tissue sample. It is understood that in generating an acellular sample from a tissue sample, some or all of the cells may lyse. In certain embodiments, an acellular sample comprises one or more components from such lysed cells. In certain embodiments, an acellular sample exhibits no substantial metabolic activity (see definition of "substantial metabolic activity", infra).

"Bioabsorbable", "Bio-absorbable": The terms "bioabsorbable" and "bio-absorbable" as used herein refer to the characteristic of existing for a limited time in the context of a biological environment. In certain embodiments, a regeneration matrix of the present invention, and/or produced according to one or more methods of the present invention, is bioabsorbable. "Bioabsorbable" in the context of a bioabsorbable regeneration matrix means that the regeneration matrix would no longer be recognizable as existing in its initial form if observed at a time after it was placed in the context of a biological environment. In certain embodiments, a bioabsorbable regeneration matrix may exist for days, weeks or months when placed in the context of a biological environment. For example, a bioabsorbable regeneration matrix may exist for 1, 2, 3, 4, 5, 6, 7, 8, 9 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 110, 120, 130, 140, 150, 160, 170, 180 days or more when placed in the context of biological environment. A bioabsorbable regeneration matrix may be bioabsorbed by any of a variety of mechanisms. In certain embodiments, a bioabsorbable regeneration matrix may be bioabsorbed through the action of cellular activity. For example, a bioabsorbable regeneration matrix is bioabsorbed through the action of macrophages that break down the bioabsorbable regeneration matrix. In certain embodiments, a bioabsorbable regeneration matrix is bioabsorbed after being broken down via mechanical, chemical, metabolic and/or enzymatic degradation. It will be understood by those of ordinary skill in the art that the precise mechanism of bioabsorbability is not critical, so long as the break down products of the regeneration matrix can be absorbed by and/or excreted from the body.

"Incubating": The term "incubating" as used herein, in the context of producing a regeneration matrix, refers to the process of permitting the regeneration matrix to form over a period of time. In certain embodiments, a regeneration matrix is produced by incubating an acellular sample in an incubation chamber (see definition of "incubation chamber", infra). In certain embodiments, an acellular sample is suspended and/or solubilized in a process medium during incubation. In certain embodiments, a regeneration matrix is produced by incubating an acellular sample at any of a variety of temperatures, so long as the acellular sample remains in a liquid state. For example, such incubation may be performed at a temperature of −2, −1, 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42 degrees Celsius, or higher, as long as the acellular sample remains in a liquid state at these temperatures. In certain embodiments, the temperature may be increased and/or decreased during the incubation period, such that incubation occurs over a range of temperatures. In certain embodiments, a regeneration matrix is produced by incubating an acellular sample at any of a variety of atmospheric pressures. For example, an acellular sample may be incubated at Standard Atmosphere ("ATM"), or any pressure above or below ATM. In certain embodiments, the atmospheric pressure is changed during incubation of an acellular sample. For example, the atmospheric pressure may be raised and/or lowered during incubation. In certain embodiments, a regeneration matrix is produced by incubating an acellular sample at any of a variety of ambient oxygen concentrations. In certain embodiments, the ambient oxygen concentration is lower than standard atmospheric oxygen concentration. For example, the ambient oxygen concentration during incubation may be approximately 21, 20, 19, 18, 17, 16, 15, 14, 13, 12, 11, 10, 9, 8, 7, 6, 5, 4, 3, 2, 1% or less. In certain embodiments, the ambient oxygen concentration during incubation is nearly or exactly 0%. In certain embodiments, a regeneration matrix is produced by incubating an acellular sample at any of a variety of ambient humidities. In certain embodiments, ambient humidity is kept low during incubation such that evaporation of liquid in the acellular sample is increased. In certain embodiments, new solute-containing liquid (including, but not limited to, e.g., a "process medium" or "physiological solution", see definitions infra) is continuously or periodically added to an acellular sample that has undergone evaporation. In such embodiments, it will be understood that the osmolarity of the acellular sample increases over time as a result of evaporation and addition of new solute-containing liquid. In certain embodiments, a regeneration matrix is produced by incubating an acellular sample in any of a variety of effective gravitational field strengths. In certain embodiments, a regeneration matrix is produced by incubating an acellular sample at an effective gravitational field strength approximately equal to that of earth's gravity (e.g., at sea level and/or at one or more discrete elevations above sea level). In certain embodiments, a regeneration matrix is produced by incubating an acellular sample at an effective gravitational field strength greater than that of earth's gravity at sea level. For example, an effective gravitational field strength greater than that of earth's gravity may be generated by incubation below sea level or in a centrifuge, as long as such a method does not produce any shaking. In certain embodiments, a regeneration matrix is produced by incubating an acellular sample at an effective gravitational field strength lower than that of earth's gravity at sea level. For example, an effective gravitational field strength lower than that of earth's gravity may be generated by incubation at high altitudes or in space.

"Incubation chamber": The term "incubation chamber" as used herein refers to any of a variety of containers that may be used to incubate (see definition of "incubate", supra) an acellular sample during formation of a regeneration matrix. In certain embodiments, an incubation chamber comprises a standard laboratory container, such as a flask, culture dish, beaker, etc. One of ordinary skill in the art will be aware of other suitable and useful standard laboratory containers. In certain embodiments, an incubation chamber comprises a sealed or semi-sealed container. In certain embodiments, an incubation chamber is a sealed or semi-sealed container that is permeable or semi-permeable to one or more substances. For example, in certain embodiments, an incubation chamber comprises a container that is permeable to air and/or gaseous molecules. In certain embodiments, an incubation chamber comprises an Opticell® cassette (BioCrystal Ltd., Westerville, Ohio). In certain embodiments, a sealed or semi-sealed incubation chamber is designed such that material may be added and/or removed to the container after the incubation process has begun. For example, an incubation chamber that is permeable or semi-permeable to air and/or gaseous molecules may be designed such that liquid and/or solid material may be added and/or removed from the chamber at one or more times during and/or after incubation. In certain embodiments, a sealed or semi-sealed incubation chamber is designed such that material may be added and/or removed through the use of a needle or other instrument that is capable of penetrating the incubation chamber. In certain embodiments, it is desirable that a sealed or semi-sealed incubation chamber that is penetrated with a needle or other instrument does "reseals" itself (and/or is capable of being resealed) such that the incubation chamber retains its sealed or semi-sealed state.

"Matrix": The term "matrix" as used herein refers to any physical structure including but not limited to, a solid or semi-solid structure and/or a suspension. In certain embodiments, the present invention provides matrices that have regenerative characteristics (see definition of "regenerative", infra). Such a regenerative matrix is referred to herein as a "regeneration matrix".

"Process medium": The term "process medium" as used herein refers to a liquid solution that may be added to a tissue sample, an acellular sample, or both during the process of generating a regeneration matrix. In certain embodiments, a process medium comprises a physiological solution (see definition of "physiological solution), infra). In certain embodiments, a process medium comprises a minimal salt solution. For example, a process medium may be PBS. One of ordinary skill in the art will be aware of other minimal salt solutions that may be used in accordance with the present invention. Furthermore, one of ordinary skill in the art will be aware of compositions and methods useful for modifying minimal salt solutions to achieve one or more desirable solution properties including, but not limited to, pH, osmolarity, buffering capacity, concentrations of one or more particular ions, and/or any of a variety of other solution properties. In certain embodiments, a process medium includes one or more therapeutic agents (see definition of "therapeutic agent", infra). In certain embodiments, a process medium is added to a tissue sample prior to, during and/or after isolation. In certain embodiments, a process medium is added to an acellular sample prior to, during and/or after removal of cells. In certain embodiments, a process medium is added to an acellular sample during the process of incubation. In certain embodiments, a process medium is added at multiple times during the process of incubation. In certain embodiments, one or more components of a process medium added during the regeneration matrix production process becomes part of the produced regeneration matrix.

"Physiological solution": The term "physiological solution" as used herein refers to a solution that is similar or identical to one or more physiological condition or that can change the physiological state of a certain physiological environment. The term "physiological solution" as used herein also refers to a solution that is capable of supporting growth of cells (including, but not limited to, mammalian, vertebrate, and/or other cells). In certain embodiments, a physiological solution comprises a defined medium, in which the concentration of each of the medium components is known and/or controlled. Defined media typically contain all the nutrients necessary to support cell growth, including, but not limited to, salts, amino acid, vitamins, lipids, trace elements, and energy sources such a carbohydrates. Non-limiting examples of defined media include DMEM, Basal Media Eagle (BME), Medium 199; F-12 (Ham) Nutrient Mixture; F-10 (Ham) Nutrient Mixture; Minimal Essential Media (MEM), Williams' Media E, and RPMI 1640. One of ordinary skill in the art will be aware of other defined media that may be used in accordance with the present invention. In certain embodiments, a physiological solution comprises a mixture of one or more defined media. In certain embodiments, a physiological solution is a complex medium, in which at least one of the medium components is neither known nor controlled. Although physiological solutions are useful in producing a regeneration matrix according to methods of the present invention, as will be clear from the entirety of this detailed description, an acellular sample that is incubated to produce a regeneration matrix does not contain cells (see definition of "acellular sample", supra). As such, even though such a process medium may be capable of supporting cell growth, it is understood that cell growth is not a necessary component of regeneration matrix production. However, in certain embodiments, cells may be added to the incubation chamber at a specific time point or time points during the regeneration matrix forming process. In these cases it is understood that the physiological solution itself, or in combination with the regeneration matrix solution, can support the viability of the cells added to the incubation chamber.

"Regeneration", "Regenerate", "Regenerative": These terms as used herein refer to any process or quality that initiates, increases, modulates, promotes, supports, and/or directs the growth, regrowth, repair, functionality, patterning, connectivity, strengthening, vitality, and/or the natural wound healing process of weak, damaged, lost, and/or degenerating tissue. These terms can also refer to any process or quality that initiates, increases, modulates, promotes, supports, and/or directs the growth, strengthening, functionality, vitality, toughness, potency, and/or health of weak, tired, and/or normal tissue. In certain embodiments, the present invention provides compositions and methods useful in the regeneration of damaged, lost and/or degenerated tissue. For example, methods and compositions of the present invention may be employed to initiate, increase, support, promote, and/or direct the regeneration of damaged, lost, and/or degenerated tissue. In certain embodiments, the present invention provides a regeneration matrix (see definition of "matrix", supra) that exhibits one or more regenerative properties or activities. In certain embodiments, regeneration comprises initiating, increasing, modulating, promoting, supporting, and/or directing one or more of the following processes: natural wound healing, tissue growth, tissue functionality, patterning, connectivity, angiogenesis, proliferation and/or activation of progenitor cells, cell growth and/or proliferation, cell specialization and/or elongation, dedifferentiation and/or differentiation of cells, up-regulation of cellular genes related to regeneration, and/or inhibition of scar formation. However, regeneration is not limited to these processes, qualities or activities and one of ordinary skill in the art will be aware of other processes, qualities or activities that are considered "regeneration", "regenerate" or "regenerative" in the field.

"Substantial metabolic activity": The term "substantial metabolic activity" as used herein refers to metabolic activity typically exhibited by intact cells in vitro or in vivo. In certain embodiments, acellular samples and/or regeneration matrices of the present invention lack cells and therefore do not exhibit substantial metabolic activity. A variety of techniques are known to those skilled in the art by which metabolic activity may be detected and/or measured. For example, intact cells produce significant quantities of ATP by aerobic and/or anaerobic breakdown of macromolecules (e.g., sugars, amino acids, lipids, etc.) Thus, the production of significant ATP levels is typically indicative of the presence of intact cells in a sample. It will be understood by those of ordinary skill in the art that certain phenomena indicative of the presence of intact cells may be detected in an acellular sample. However, such cellular-indicative phenomena are typically observed at levels or magnitudes that are lower or reduced compared to the level or magnitude of such phenomena occurring as a result of the presence of cells. Thus, for example, an acellular sample and/or regeneration matrix may exhibit low levels of ATP production, which levels are substantially lower than the levels that would be produced were intact cells present in the acellular sample and/or regeneration matrix.

"Therapeutic agent": The term "therapeutic agent" as used herein refers to any of a variety of agents that exhibit one or more beneficial therapeutic effects when used in conjunction with methods and/or regeneration matrices of the present invention. Examples of therapeutic agents that may be used with inventive regeneration matrices and methods include, without limitation, proteins, peptides, drugs, cytokines, extracellular matrix molecules, and/or growth factors. One of ordinary skill in the art will be aware of other suitable and/or advantageous therapeutic agents that may be used in accordance with the present invention. In certain embodiments, the magnitude(s) of one or more beneficial therapeutic effects of a therapeutic agent are increased when administered in a regeneration matrix. In certain embodiments, the activity of one or more beneficial therapeutic effects of a therapeutic agent is prolonged when administered in a regeneration matrix. In certain embodiments, one or more beneficial therapeutic effects of a therapeutic agent are released over time when administered in a regeneration matrix. In certain embodiments, one or more beneficial effects of a therapeutic agent are protected from substantially decreasing over time when administered in a regeneration matrix. In certain embodiments, two or more therapeutic agents are administered in a regeneration matrix.

"Tissue sample": The term "tissue sample" as used herein refers to a biological sample that comprises cells and/or extracellular material. For example, a tissue sample may comprise any of the four basic animal tissue types (muscle tissue, connective tissue, epithelial tissue, and nerve tissue), any of the three basic plant tissue types (ground tissue, dermal tissue, and vascular tissue), any of a variety of other specific tissue types (e.g., blood or liver tissue), and/or any combination of these or other tissue types. In certain embodiments, a tissue sample comprises tissue from placental tissue, from tissue of the umbilical cord, and/or from tissue of one or more of the following organ systems: cardiovascular, digestive, endocrine, excretory, immune, integumentary, lymphatic, muscular, nervous, reproductive, respiratory, and/or skeletal. One of ordinary skill in the art will be aware of other tissue types that may be used in accordance with the present invention. In certain embodiments, a tissue sample comprises two or more distinct tissue types. A tissue sample may be isolated from any of a variety of organisms. As non-limiting examples, a tissue sample may be isolated from a human, a pig, a rat, a salamander, a cow, a dog, a cat, a mouse, and/or a rabbit. One of ordinary skill in the art will be aware of other suitable organisms from which a tissue sample can be isolated. In certain embodiments, a tissue sample is used as starting material to produce a regeneration matrix. In certain embodiments, a tissue sample used to produce a regeneration matrix is isolated from the type of organism in which the regeneration matrix is to be used. For example, a regeneration matrix to be used in humans may be produced from a starting tissue sample isolated from humans. In certain embodiments, a tissue sample used to produce a regeneration matrix is isolated from the individual organism in which the regeneration matrix is to be used. For example, a regeneration matrix to be used in an individual human may be produced from a starting tissue sample isolated from that individual human. In certain embodiments, a regeneration matrix is produced from blood of the individual human in which the regeneration matrix is to be used.

Overview

In certain embodiments, the present invention provides a regeneration matrix that is able to initiate, increase, support, and/or direct tissue regeneration at a site of tissue damage. For example, a regeneration matrix according to the present invention may be used to regenerate nerve tissue, muscle tissue, liver tissue, heart tissue, lung tissue, and/or skin tissue.

The ability of a regeneration matrix to repair injuries and/or degenerated tissue, including, but not limited to, tissue of the central nervous system (CNS), is based upon the science of wound healing and development of tissue. Although the process of wound healing has not been fully elucidated, the present invention encompasses the finding that a regeneration matrix is able to initiate, increase, support, and/or direct the regeneration of damaged and/or degenerated tissue.

One advantage of regeneration matrices of the present invention is that they are able to suppress certain wound healing processes that do not enhance tissue regeneration while enhancing other processes that allow the patient to regenerate tissue. The body is remarkable in that it is able to repair itself quickly; however, certain aspects of the wound healing process do not allow for original regenerative functionality found in lower animal species such as salamanders. By reducing the undesirable traits and enhancing or recreating the desirable traits of the wound healing and tissue development processes, a regeneration matrix is able to achieve superior results. In contrast to lower animal species such as salamanders, the natural wound healing process in humans is programmed for generating the quickest recovery from injury by isolating the injury site from the rest of the body with scar tissue which, in the case of spinal cord or other CNS injury, results in a lack of recovery of function due to the limited effect of or lack of other, parallel wound healing processes. The same is true to injuries and degeneration of other parts of the central nervous system, as well as other tissues of the body.

In certain embodiments, methods and/or regeneration matrices of the present invention are useful for the treatment of damaged, lost and/or degenerated nerve tissue, e.g., central nervous system tissue. Historically there has been a lack of significant progress and treatment available for central nervous system injuries, including those of the spinal cord. The major reason for the lack regenerative treatments for tissues, especially tissue of the central nervous system, is due to the vital and highly complex nature of these tissues.

The present invention encompasses the finding that the highly complex biological and structural nature of the spinal cord can be restored in SCI patients with products that contain the relevant biological activities that promote the restoration of this complex biological and structural nature as well as promoting the correct patterning and reconnectivity of the spinal cord. The same is true for other areas of the central nervous system. Regeneration matrices of the present invention are designed to have these and other advantageous characteristics. Furthermore, additional functionalities can be added to regeneration matrices of the present invention in a relatively simple and straight-forward manner. To date, no other formulation for treating CNS damage and SCI patients has been developed with such an all-inclusive approach to restoring the complex functionality of the central nervous system, such as the spinal cord in SCI patients.

Wound Healing

During the wound healing process, several types of cells are involved at different stages of the wound healing process, each with their unique contributions to regenerating and restoring functionality to the damaged tissue. The first line of cells generally come from the blood stream, and include macrophages whose job it is to clean up the site of damage to create room for new cell growth and to release growth factors that activate cells that are needed in the next stage of the wound healing process. Although macrophages alone have a relatively small effect on spinal cord regeneration, it is better than nothing at all. However, combined with other mechanisms of action, activated macrophages can impart a more significant effect on the regeneration process. In certain embodiments, a regeneration matrix of the present invention has been observed to increase the rate at which activated macrophages enter the site of spinal cord injury in large numbers within days after implantation, thus making it unnecessary to inject any activated macrophages into the site of tissue damage. It will be understood by those of ordinary skill in the art, however, that although inventive regeneration matrices promote macrophage invasion to a site of tissue damage, macrophages may nevertheless be administered at or near the site of injury in conjunction with, or in addition to, a regeneration matrix of the present invention.

The next step in the process of natural wound healing is the recruitment of new blood vessels and, in the case of traumatic injuries, the recruitment of fibroblasts that create a scar that encloses the site of traumatic injury so that the surrounding undamaged tissue can continue to function and compensate for the lost functionality of the damaged tissue while it is slowly repaired. The growth factors released by the activated macrophages promote the recruitment of these new blood vessels and fibroblasts. Unfortunately, the central nervous system is enclosed by a blood-brain barrier that restricts invasion by macrophages and promotion of recruitment of new blood vessels. Inhibitory factors surrounding the blood-brain barrier, especially in CNS injury or degeneration, restrict new blood vessels from entering the site of CNS damage, resulting in fibroblasts and glial cells forming scars without the simultaneous formation of new blood vessel. The resulting scars become very thick and impenetrable, and the lack of new blood vessels means that the site of injury cannot be rebuilt. The ultimate result is the formation of lesions (hollow structures enclosed by thick, impenetrable scars) and long-term (chronic) CNS damage—and in the case of spinal cord injury—chronic paralysis. In certain embodiments, regeneration matrices of the present invention contain wound healing properties that slow down and inhibit scar formation, while simultaneously promoting new blood vessel formation. Since the lack of blood vessels results in lesions (fluid filled cavities lacking in any cells), it is advantageous for new blood vessels to form in and around these lesions and/or areas where lesions are about to form. Without wishing to be bound by theory, it is hypothesized that regeneration matrices of the present invention can create new blood vessels by a unique pathway: by transdifferentiating (transforming) the activated macrophages into von Willebrand factor-positive endothelial-like cells that naturally form new blood vessels (see FIGS. 1A, 1B, and 1C). Thus, according to this hypothesis, after the activated macrophages that were attracted to the site of CNS injury by such a regeneration matrix have done their job of cleaning up the site of damage and have released growth factors, they are transformed into a new, specialized types of cells that form new blood vessels. The end result is an extensive new network of blood vessels that provide the nutrients and oxygen for new cells and for new CNS tissue. In animal models of CNS injury, an implanted regeneration matrix has been found to have already started creating a network of new blood vessels (this blood vessel network does not resemble the type of blood vessel growth seen in tumors, but instead resembles the types of large-sized blood vessel networks present in embryonic development) within a week of implantation with limited presence of any inhibitory scars (see e.g., FIGS. 2A, 2B, 2C and 2D).

After the formation of a new blood vessel network, the next step in the wound healing process typically involves the migration of surrounding cells to the site of injury. These cells migrate to the site of injury in order to feed on the fresh supply of nutrients and oxygen provided by the newly-formed blood vessels. Unfortunately, in the case of nerve tissue damage, nerve cells are the only long-term cells in the body that do not migrate and/or divide (multiply) after they have differentiated (transformed into adult cells)—if they did, we would lose the memory inherent in these cells every time they migrate or divide, in effect 'forgetting' those memories (whether somatic or autonomic) that the particular nerve cell is a part of. However, as is known to those of ordinary skill in the field, nerve cells are capable of forming new, additional memories or connections through the formation and/or extension of axons and dendrites. In certain embodiments, a regeneration matrix promotes a several-fold increase in the expression of one or more genes that are responsible for the formation and correct patterning and connectivity of such new connections in nerve cells surrounding the site of injury (see e.g., FIGS. 18-19). In certain embodiments, a regeneration matrix causes nerve cells to extend into the site of injury and make effective and intelligent new connections, such as those that are controlled by, for example, GAP-43 and the Netrin family of genes, which are upregulated by the regeneration matrix. Such new connections can be utilized to generate new CNS functionality that can be harnessed by training and/or teaching, leading to advantageous functionality of the new CNS tissue. In certain embodiments, such new functionality is achieved in a short period of time, for example, within an approximately 2-month time window. As one non-limiting example, in the case of spinal cord injury, this would entail training/teaching the nerves how to move muscles in a coordinated fashion to enable movement. As another non-limiting example, in the case of Broca's area (the speech center) in the brain, this would entail training/teaching the nerves how to create coherent speech.

In certain embodiments, regeneration matrices of the present invention further enhance the formation of new CNS tissue by recruiting and increasing the proliferation of triphasic neuroprogenitor cells. Triphasic neuroprogenitor cells are a type of unique and highly mobile young cell that neuroscientists have implicated as being responsible for the spontaneous growth of new CNS tissue, especially in the brain, observed in several human cases where the person's damaged CNS tissue at least partially repaired itself. Triphasic neuroprogenitor cells have been difficult to study in vitro (in a dish) because by their nature they differentiate (transform) into nerve cells or glial cells (neuronal supporting cells: astrocytes and oligodendrocytes) the moment they realize that their surroundings is lacking in one of these cells (they appear to turn into the type of cell that their surroundings is lacking). However, the present invention encompasses the finding that in the presence of a regeneration matrix, triphasic neuroprogenitor cells continue to proliferate until the regeneration matrix is removed or biodegraded (e.g., in the body), at which point they transform and create an extensive neural network. Without wishing to be bound by theory, one hypothesis is that as the last step of the process of generating new CNS tissue, triphasic neuroprogenitor cells partially fill in the missing portions of the new CNS tissue being created that other surrounding nerve and glial cells did not fill in during their phase of the regeneration matrix regeneration process. Regardless of the precise mechanism, the end result is that triphasic neuroprogenitor cells that are stimulated to proliferate by inventive regeneration matrices produce new nerve tissue.

In terms of the other approaches in the field of wound healing, prior products and approaches have either resulted in slight to borderline significant improvements in experimental animals over non-treated control animals. Furthermore, clinical trials to date have not demonstrated any significant improvement over placebo due to these single-approach products. Additionally, in several cases, technical problems relating to adverse immunological responses in human implants have been insurmountable. Other difficulties have included the inability to deliver a product to a human patient without it either being washed away by the cerebrospinal fluid (which typically moves at a speed of approximately 5 mm/min at a pressure of 120 mm $H_2O$ in a human) and/or causing significant additional injury during implantation. Regeneration matrices of the present invention overcome these and other difficulties. In certain embodiments, administering regeneration matrices of the present invention results in significant improvement in experimental animals over non-treated control animals with no observed toxicological effects. Furthermore, regeneration matrices of the present invention are easily obtainable in a form that can be delivered to a human patient without long-term immunological problems.

Regeneration Matrix Production

The present invention encompasses the finding that regeneration matrices may be produced by any of a variety of methods. In certain embodiments, different production methods lead to regeneration matrices that exhibit different physical characteristics, biological properties and/or therapeutic activities. Furthermore, in certain embodiments, the physical characteristics, biological properties and/or therapeutic activities of regeneration matrices produced according to methods of the present invention are altered by the providing one or more exogenous factors during the production process.

In certain embodiments, regeneration matrices of the present invention are produced by incubating an acellular sample for a period of time. In certain embodiments, an acellular sample is isolated from a tissue sample. An acellular sample may be generated from any of the four basic tissue types (muscle tissue, connective tissue, epithelial tissue, and nerve tissue), from any of a variety of other non-basic tissue types, of from any combination of these or other tissue types. In certain embodiments, an acellular sample is generated from any of the four basic animal tissue types (muscle tissue, connective tissue, epithelial tissue, and nerve tissue), any of the three basic plant tissue types (ground tissue, dermal tissue, and vascular tissue), any of a variety of other specific tissue types (e.g., blood or liver tissue), and/or from any combination of these or other tissue types. In certain embodiments, an acellular sample is generated from placental tissue, from tissue of the umbilical cord, and/or from tissue of one or more of the following organ systems: cardiovascular, digestive, endocrine, excretory, immune, integumentary, lymphatic, muscular, nervous, reproductive, respiratory, and/or skeletal.

A regeneration matrix can be formed from any animal within the animal kingdom, and/or from any plant within the plant kingdom, in practically all tissues and fluids. However, in certain embodiments, a regeneration matrix is produced from blood. Without wishing to be bound by theory, it is hypothesized that regeneration matrices are at least partially formed by components of cells that are undergoing or are in the vicinity of tissue damage, especially massive tissue damage. Such a mechanism appears to be a way for cells to induce surrounding cells to regenerate damaged tissue. A similar but distinct phenomenon was observed but not fully understood by Becker et al. in 1974 (Becker, R. O. et al., *Regeneration of the ventricular myocardium in amphibians*, Nature 248, 145-147, 1974) while studying the hearts of newts. Becker observed that when 30%-50% of the newt's heart was cut out, the surrounding red blood cells lysed and their released nuclei aggregated to form new myocardial tissue, allowing the newt heart to be regenerated in about 4 hours, and thus allowing many of the newts to survive. As will be clear from the remainder of this description, regeneration matrices of the present invention are distinct from and operate via a mechanism different from the phenomenon observed by Becker et al., since regeneration matrices of the present invention are produced from an acellular sample and do not on their own become a cell based living tissue. Nevertheless, in certain embodiments, regeneration matrices of the present invention are seeded or mixed with cells during or after their formation to confer one or more beneficial characteristics or functions on the regeneration matrix. As will be understood, however, such cells are not required for formation of regeneration matrices of the present invention.

Although a functional regeneration matrix may be produced from any of a variety of tissues, it will be understood that the exact composition of a regeneration matrix is influenced by, among other things, the tissue type from which the acellular sample is generated. As non-limiting examples, a regeneration matrix may be produced from liver tissue, whole blood and/or from one or more blood fractions. In the case where a regeneration matrix is produced from whole blood, major protein components of the regeneration matrix are typically albumin and hemoglobins. In the case where a regeneration matrix is produced from the plasma-platelet-buffy coat fraction of blood, a major protein component of the regeneration matrix is typically albumin. Nevertheless, regeneration matrices produced from both whole blood and from the plasma-platelet-buffy coat fraction each function to initiate, increase, support, and/or direct tissue regeneration at a site of tissue damage, loss and/or degeneration. In certain embodiments, a regeneration matrix is produced from an acellular sample generated from whole blood. In certain embodiments, a regeneration matrix is produced from an acellular sample generated from one or more blood fractions including, but not limited to an erythrocyte fraction, a buffy-coat fraction, a platelet fraction, and/or a plasma fraction. Such fractions can be generated, for example, by allowing whole blood to settle and separate via gravity. In certain embodiments, blood fractions are generated by centrifugation. One of ordinary skill in the art will be aware of other techniques for separating blood into fractions, which fractions may be used to produce a regeneration matrix of the present invention. In certain embodiments, a regeneration matrix is produced from blood or other tissue that has been frozen. In certain embodiments, such tissue has been frozen for a period of days, weeks, months or years. In certain embodiments, better yields and development of regeneration matrices are obtained when the blood or other tissue is subjected to multiple freeze-thaw cycles at a temperature range that is close to the freezing-melting point of the sample. In certain embodiments, a regeneration matrix is produced from blood or other tissue that is isolated from cadavers (e.g., cadavers that are several weeks old). In certain embodiments, a regeneration matrix is produced from placental or umbilical cord blood. One of ordinary skill in the art will be aware of other sources of blood, bodily fluids (e.g., cerebrospinal fluid and lymph) and tissues that can be used for producing a regeneration matrix.

Furthermore, in the case of whole blood, as shown in Examples 1 and 2, the presence of an anticoagulant in the blood sample results in regeneration matrices with different adhesive properties. Any of a variety of anticoagulants may be used including, but not limited to, heparin, EDTA, and/or citrate. One of ordinary skill in the art will be aware of other known anticoagulants, as well as coagulants, that can be used to produce regeneration matrices with different physical characteristics, biological properties and/or therapeutic activities.

In certain embodiments, an acellular sample is generated by removing cells from a tissue sample. Any of a variety of techniques may be used to remove such cells. For example, a tissue sample may be subjected to centrifugation to separate the tissue sample into cell-containing and non-cell-containing fractions, which non-cell-containing fraction is then isolated. In certain embodiments, cells are removed from a tissue sample by passing the tissue sample through a filter with a pore size small enough to exclude cells. For example, cells may be removed from a tissue sample by passing the tissue sample though a filter with a pore size of 5 µm, 1.2 µm and/or 0.8 µm. In certain embodiments, the pore size of the filter alters the physical characteristics, biological properties and/or therapeutic activities of the produced regeneration matrix. The exact pore size can be determined by the practitioner depending on experimental and/or laboratory constraints, the desired characteristics of the regeneration matrix and/or any of a variety of other factors deemed important by the practitioner. In certain embodiments, a tissue sample is suspended, solubilized and/or diluted prior to removing cells. For example, a tissue sample may be suspended, solubilized and/or diluted in a process medium and/or a physiological solution prior to removing cells from the tissue sample.

A regeneration matrix may be produced by incubating an acellular sample for any of a variety of incubation times. For example an acellular sample may be incubated for 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60 or more days. Functional regeneration matrix in in vitro assays has been detected in regeneration matrix produced after 6 days, 12 days, 15 days, 21 days and 28 days, and has remained functional with longer incubation period of 6 weeks or longer. By modifying the environmental parameters and/or a process medium used in the production process, functional regeneration matrices can be produced in a shorter period of time. For example, by decreasing the oxygen concentration to approximately 0% and/or by increasing the aggregating properties or effects of the process medium by, for example, increasing its salt concentration, functional regeneration matrices can be produced within minutes, hours, or a few days. In certain embodiments, the activity of a regeneration matrix produced by incubating an acellular sample increases as the period of incubation increases. In certain embodiments, a regeneration matrix produced by incubating an acellular sample reaches a maximal or near-maximal activity after a period of incubation. In such embodiments, a regeneration matrix increases in activity only incrementally, if at all, as a result of further incubation. In such embodiments, it is possible that the regeneration matrix may lose activity as a result of further incubation.

Applicant has discovered that shaking or otherwise disturbing the acellular sample during the initial formation of the regeneration matrix results in an incomplete and/or defective regeneration matrix and/or lack of a produced regeneration matrix altogether (as well as a corresponding decrease in the biological activity of such incomplete and/or defective regeneration matrices). In certain embodiments, an acellular sample is incubated such that the sample is not shaken or otherwise disturbed for a period of time while the regeneration matrix is forming. For example, an acellular sample may be incubated in the absence of shaking or other disturbance for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days or more. In certain embodiments, an acellular sample is incubated such that the sample is not shaken or otherwise disturbed for the entire time that the regeneration matrix forms.

Certain incubation conditions and/or addition of one or more exogenous factors during the production process may alter the incubation time necessary for the regeneration matrix to achieve a desired level of activity. As one non-limiting example, decreasing the ambient concentration of oxygen decreases the amount of time necessary to achieve a desired level of regeneration matrix activity. In certain embodiments, the ambient oxygen concentration during incubation is approximately 21, 20, 19, 18, 17, 16, 15, 14, 13, 12, 11, 10, 9, 8, 7, 6, 5, 4, 3, 2, 1% or less. In certain embodiments, the ambient oxygen concentration during incubation is nearly or exactly 0%. In certain embodiments, incubation in a low oxygen environment results in a regeneration matrix with a desired level of activity in as little as 3 days. In certain embodiments, incubation in a low oxygen environment results in a regeneration matrix with a desired level of activity in as little as 7 days. In certain embodiments, the ambient oxygen concentration during incubation is altered (e.g., raised and/or lowered) during the incubation process. One of ordinary skill in the art will be able to choose one or more appropriate ambient oxygen concentrations depending on the time constraints in forming the regeneration matrix, the type of tissue damage for which the regeneration matrix will be used, experimental and/or laboratory constraints, and/or any of a variety of other factors deemed important by the practitioner.

In certain embodiments, the ambient humidity is adjusted or controlled during incubation. For example, a regeneration matrix is produced by incubating an acellular sample at any of a variety of ambient humidities. In certain embodiments, ambient humidity is kept low during incubation such that evaporation of liquid in the acellular sample is increased. In certain embodiments, new solute-containing liquid (e.g., a "process medium" and/or "physiological solution") is continuously or periodically added to an acellular sample that has undergone evaporation. In such embodiments, it will be understood that the osmolarity of the acellular sample increases over time as a result of evaporation and addition of new solute-containing liquid. In certain embodiments, such an increase in osmolarity results in a change in the physical characteristics, biological properties and/or therapeutic activities of the produced regeneration matrix. As one non-limiting example, it has been shown that increasing the osmolarity of a solution and/or suspension containing the acellular sample during the incubation process results in a regeneration matrix with a more solid physical consistency relative to a regeneration matrix produced by a process in which the osmolarity is not increased, or is increased by a lesser amount. Such a regeneration matrix may be used as an implantable composition when it is desired that the regeneration matrix retain a certain physical shape for an extended period of time.

A regeneration matrix that has a less solid physical consistency (e.g., such as a regeneration matrix produced by a process where the osmolarity is held constant or increased by a lesser amount) are of use when it is desired to, for example, inject a regeneration matrix into a subject. In certain embodiments, the ambient humidity is altered (e.g., raised and/or lowered) during the incubation process to control the rate of change in the osmolarity. One of ordinary skill in the art will be able to choose one or more appropriate ambient humidities depending on the time constraints in forming the regeneration matrix, the type of tissue damage for which the regeneration matrix will be used, experimental and/or laboratory constraints, and/or any of a variety of other factors deemed important by the practitioner. Furthermore, the density, porosity, and/or level of hydration of the formed regeneration matrix can be changed by centrifugation or lyophilization of the formed regeneration matrix. For example, the formed regeneration matrix could be centrifuged at 5000×g to increase its density and hardness for implantation into a bone defect for supporting the regeneration of the bone.

In certain embodiments, regeneration matrices of the present invention are produced by incubating an acellular sample for a period of time in an incubation chamber. Any of a variety of incubation chambers may be used. In certain embodiments, an incubation chamber comprises a sealed or semi-sealed container that is permeable or semi-permeable to one or more substances, e.g., air and/or gaseous molecules. For example, an Opticell® cassette (BioCrystal Ltd., Westerville, Ohio) may be used as an incubation chamber to produce a regeneration matrix from an acellular sample. In certain embodiments, a sealed or semi-sealed incubation chamber is designed such that material may be added to and/or removed from the container after the incubation process has begun. For example, an incubation chamber that is permeable or semi-permeable to air and/or gaseous molecules may be designed such that liquid and/or solid material may be added to and/or removed from the chamber at one or more times during and/or after incubation. Such incubation chambers are advantageous when it is desirable to increase the osmolarity of the acellular sample during the incubation process. For example, the osmolarity of the acellular sample may be increased during the incubation process by permitting the solvent of a liquid solution or suspension containing the acellular sample (which solution or solvent may be generated, e.g., by adding a process medium or physiological solution to the acellular sample and/or to a tissue sample from which the acellular sample is generated) to evaporate over time, and continuously or periodically added new solute-containing liquid to the acellular sample. Such a solute-containing liquid may comprise a process medium and/or a physiological solution. In the case where an acellular sample has been solubilized or suspended in a process medium and/or a physiological solution, that same process medium and/or physiological solution may be added to the acellular sample during the incubation process. Additionally or alternatively, a different process medium and/or physiological solution may be added to the acellular sample during the incubation process. Additionally or alternatively, a solute-containing liquid to be added to the acellular sample is neither a process medium nor a physiological solution.

In certain embodiments, a regeneration matrix exhibits different physical characteristics, biological properties and/or therapeutic activities depending on the process medium and/or physiological solution used during the production process. For example, as shown in Example 11, a regeneration matrix produced using TR-10 media exhibits an increased biological activity as compared to a regeneration matrix produced using DMEM/F-12 media. One of ordinary skill in the art will be able to determine appropriate process media and/or physiological media to achieve a regeneration matrix that exhibits one or more desired physical characteristics, biological properties and/or therapeutic activities without undue experimentation.

A process medium and/or a physiological solution may be added to the tissue sample and/or acellular sample at any of a variety of time points during the regeneration matrix production process. In certain embodiments, a process medium is added to the tissue sample and/or acellular sample during isolation of the tissue sample, prior to removing the cells from the tissue sample, prior to incubating the acellular sample, and/or during the incubating process.

In certain embodiments, a regeneration matrix is produced by incubating an acellular sample in the presence of one or more exogenous factors. For example, an acellular sample may be incubated in the presence of one or more therapeutic agents, one or more cell types, or both. In certain embodiments, such exogenous factors alter the physical characteristics and/or augment the biological and/or therapeutic activities of a regeneration matrix. For example, as shown in Example 9, a regeneration matrix supplemented by the addition of ITS, EGF, and bFGF during production of the regeneration matrix results in an increased effect of the regeneration matrix on neurite outgrowth activity.

Any of a variety of therapeutic agents may be used to increase and/or supplement the activity of regeneration matrices of the present invention. Examples of therapeutic agents that may be used with inventive regeneration matrices and methods include, without limitation, proteins, peptides, drugs, cytokines, extracellular matrix molecules, and/or growth factors. One of ordinary skill in the art will be aware of other suitable and/or advantageous therapeutic agents that may be used in accordance with the present invention. In certain embodiments, the magnitude(s) of one or more beneficial therapeutic effects of a therapeutic agent are increased when administered in a regeneration matrix. In certain embodiments, the activity of one or more beneficial therapeutic effects of a therapeutic agent is prolonged when administered in a regeneration matrix. In certain embodiments, one or more beneficial therapeutic effects of a therapeutic agent are released over time when administered in a regeneration matrix. In certain embodiments, one or more beneficial effects of a therapeutic agent are protected from substantially decreasing over time when administered in a regeneration matrix. In certain embodiments, two or more therapeutic agents are administered in a regeneration matrix. In certain embodiments, a therapeutic agent is added during the process of producing a regeneration matrix. For example, a therapeutic agent may be added at one or more step of the production process including, but not limited to, during isolation of the tissue sample, prior to the removing the cells from the tissue sample, prior to incubating the acellular sample, and/or during the incubating process.

In certain embodiments, a therapeutic agent is distributed evenly throughout the regeneration matrix. In certain embodiments, a therapeutic agent is distributed heterogeneously throughout the regeneration matrix. For example, a therapeutic agent may be more concentrated at or near the core of a regeneration matrix. This could be achieved, for example, by introducing the therapeutic agent during the first few days or the first half of the regeneration matrix formation period, followed by removal of most or all of the solution surrounding the forming regeneration matrix in the incubation chamber, adding more of the initial acellular sample or solution to the incubation chamber until a desired level is achieved, and then further incubating the acellular sample and regeneration matrix in order to continue the process of formation of the regeneration matrix. The additional acellular sample or solution could also be added together with another therapeutic agent that would then become heterogeneously concentrated closer to the outside surface of the forming regeneration matrix, and would thus be released earlier into its surrounding environment than the first therapeutic agent when the regeneration matrix bio-degrades or is degraded; this method could be used in applications where it is desired that the therapeutic agents are delivered at different time points (e.g., one after the other) to a specific site. In certain embodiments, such a heterogeneous distribution affects the properties and/or function of the therapeutic agent in vivo. For example, such a heterogeneous distribution may result in an alteration in the magnitude(s) of one or more beneficial therapeutic effects of the therapeutic agent, prolongment of activity of one or more beneficial therapeutic effects of the therapeutic agent, an alteration in the time-release characteristics of one or more beneficial therapeutic effects of the therapeutic agent, and/or protection of one or more beneficial effects of the therapeutic agent from substantially decreasing over time.

Any of a variety of cell types may be used to increase and/or supplement the activity of regeneration matrices of the present invention. However, even though cells may be used to increase and/or supplement the activity of regeneration matrices of the present invention, it will be understood that such cells are not required to form a regeneration matrix. In certain embodiments, cells are added to an acellular sample form which cells have been removed. In certain embodiments, cells of a type different from cells present in the tissue sample from which the acellular sample is generated are used. Examples of cell types that may be used in accordance with the present invention include, without limitation, stem cells, progenitor cells, and/or somatic cells. One of ordinary skill in the art will be aware of other suitable and/or advantageous cell types that may be used in accordance with the present invention. In certain embodiments, cells are added during the process of producing a regeneration matrix. For example, cells may be added at one or more step of the production process including, but not limited to, during isolation of the tissue sample, prior to removing the cells from the tissue sample, prior to incubating the acellular sample, and/or during the incubating process. In certain embodiments, cells are distributed evenly throughout the regeneration matrix. In certain embodiments, cells are distributed heterogeneously throughout the regeneration matrix. For example, cells may be more concentrated at or near the core of a regeneration matrix. In certain embodiments, such a heterogeneous distribution affects the properties and/or function of the cells in vivo.

One of the most effective ways to produce a promising regeneration matrix for implantation into a patient without triggering a significant immune response is to derive the regeneration matrix from the patient's own blood and/or tissue. However, regeneration matrices of the present invention are not limited to such autologous regeneration matrices. In certain embodiments, ready-made regeneration matrices for immediate implantation are made using allogenic blood or other tissue. In such embodiments, it may be desirable to administer such an allogenic regeneration matrix in conjunction with one or more immunosuppressive agents. Examples of such immunosuppressive agents are known to those of ordinary skill in the art. In certain embodiments, a regeneration matrix for use in on species is derived from cells from a different species. For example, a regeneration matrix produced using tissue derived from an animal (e.g., pigs) is administered to human. In certain embodiments, regeneration matrices of the present invention are useful in veterinary applications, e.g. to repair damaged and/or degenerated tissue of livestock and/or pets.

In certain embodiments, the physical characteristics, biological properties and/or therapeutic activities of a regeneration matrix are altered after the production process is substantially of fully complete. For example, in many instances it will be desirable to store a regeneration matrix for an extended period of time after it is made. As is known in the art, hydrolysis is one cause of shortened storage lifespan for a variety of biological and non-biological substances. Thus, in certain embodiments, the storage lifespan of regeneration matrices of the present invention may be increased by removing some or all of the liquid present in such a regeneration matrix. Any of a variety of techniques may be used to remove such liquid. For example, a regeneration matrix may be centrifuged to condense the proteinaceous and/or other biological macromolecular components, after which a desired amount of liquid is removed from the centrifuged sample. Additionally or alternatively, liquid may be removed from a regeneration matrix by subjecting the regeneration matrix to a filtration step (e.g., by gravity or low-speed centrifugation) using a filter with a pore size large enough to pass liquid but small enough such that regeneration matrix material does not pass through. Additionally or alternatively, liquid may be removed from a regeneration matrix by dehydrating the regeneration matrix over a period of time, either in the presence or absence of desiccants. One of ordinary skill in the art will be aware of other appropriate and/or useful methods of removing liquid from a regeneration matrix to improve it storage lifespan. It will be understood that removal of liquid from a regeneration matrix may also alter one or more of its biological properties and/or therapeutic activities. In certain embodiments, such biological properties and/or therapeutic activities are augmented by the process of removing liquid.

Furthermore, such removal of liquid may result in an additional advantage by altering the physical characteristics of a regeneration matrix such that the regeneration matrix more closely matches the physical environment in which it is to be administered. For example, decreasing the hydration level of the regeneration matrix may result in a regeneration matrix with a greater density. Such a dense regeneration matrix may advantageously be used, for example, in the regeneration of bone and/or cartilage. One of ordinary skill in the art will be aware, based on this description, of other advantageous applications for such dense regeneration matrices and will be able to use such regeneration matrices in such applications without undue experimentation.

Regeneration Matrix Composition and Characteristics

Regeneration matrices of the present invention comprise a heterogeneous mixture of proteins, lipids, carbohydrates, salts, and nucleic acid. Furthermore, regeneration matrices have been stored at refrigerated temperatures without loss of function for up to 3 months. Presumably, a regeneration matrix could be stored indefinitely using appropriate conditions. For example, the water content of a regeneration matrix may be decreased (e.g., via centrifugation, dehydration, lyophilization, etc.) to increase the length of time it may be stored. In certain embodiments, the primary structure consists mostly of aggregates of spherical structures approximately 1 to 4 µm in diameter. In certain embodiments, the primary structure consists mostly of aggregates of spherical structures approximately 100 nm in diameter. In certain embodiments, the primary structure consists mostly of aggregates of spherical structures of at least approximately 100 nm in diameter. In certain embodiments, regeneration matrices comprise such spherical structures with fibers interspersed throughout. As described above, process conditions used to form the starting material can influence the ultimate size of the spherical structures. For example, if the starting material is filtered through a 5 µm filter, the predominant spherical structures are typically about 2 to 4 µm in diameter. If the starting material is filtered through a 1.2 µm filter, the predominant structures are typically about 1 to 2 µm in diameter.

In certain embodiments, antibodies to CD56 recognize the surface of the spheres indicating the presence of neural cell adhesion molecule (NCAM). Without wishing to be bound by theory, it is hypothesized that NCAM-mediated stimulation is one mechanism by which the regeneration matrix engages neural cells and stimulates regeneration following damage. In certain embodiments, during tissue repair, tissue regeneration, and/or tissue formation, the regeneration matrix acts as an extracellular growth matrix (ECGM). When a regeneration matrix is formed from blood, the physical and functional properties are influenced by the method of blood collection (e.g., presence or absence of anticoagulants and/or type of anticoagulant) as well as the pore size used to filter the lysate prior to the incubation period. Structures similar to those formed with blood collected without anticoagulant are formed when blood is collected with the anticoagulant heparin. The regeneration matrix formed from this whole blood generally attaches to both the bottom and top of the production device (e.g., Opticell®) with a slightly different arrangement of structures on the respective surfaces. However, when blood is collected with the anticoagulants EDTA or citrate, the regeneration matrix formed from this whole blood is loosely attached to the production device and has gel-like appearance and consistency.

In certain embodiments, regeneration matrices of the present invention comprise water as their primary ingredient. In certain embodiments, the non-water composition of a regeneration matrix comprises primarily protein. In certain embodiments, the protein content of a regeneration matrix ranges from about 5 to 15% by mass. However, this percentage can be manipulated by using different ratios of tissue sample and/or acellular sample to process media in the production process. In certain embodiments, by employing such different ratios, the protein content of produced regeneration matrix is approximately 1, 2, 3, 4, 5, 6, 7, 8, 9, 10, 11, 12, 13, 14, 15, 16, 17, 18, 19, 20, 21, 22, 23, 24, 25, 26, 27, 28, 29, 30% or more. This percentage can be further changed by altering the hydration level of the produced regeneration matrix. In certain embodiments, by employing such alterations in the hydration level of the regeneration matrix, the protein content of the regeneration matrix could be less than approximately 0.1% or more than approximately 90%. In the case where a regeneration matrix is produced from whole blood, major protein components of the regeneration matrix are typically albumin and hemoglobins. In the case where a regeneration matrix is produced from the plasma-platelet-buffy coat fraction of blood, a major protein component of the regeneration matrix is typically albumin. However, one of ordinary skill in the art will understand that other protein or peptide constituents of blood are also present in these regeneration matrices. Furthermore, one of ordinary skill in the art will understand that other protein or peptide constituents may be present when the regeneration matrix is produced from an acellular sample generated from a tissue other than blood.

A regeneration matrix has important regenerative and tissue formation properties and potential. It can serve as an aid and/or scaffold for cells involved in tissue regeneration and tissue formation. In certain embodiments, regeneration matrices of the present invention allow cells to attach, proliferate and/or differentiate on or around the regeneration matrices. In certain embodiments, regeneration matrices of the present invention stimulate neurons to extend neural processes that attach to the regeneration matrix. In vitro cell culture assays using neural cells have demonstrated that a regeneration matrix selectively stimulates genes that are associated with neural cell adhesion, neuron survival, axon growth and regeneration, patterning, and connectivity. In vitro cell culture assays using human fibroblasts, have demonstrated that a regeneration matrix produced by filtration with a 5 µm filter has an inhibitory effect on the proliferation of these cells. The magnitude of such fibroblast inhibiting activity can be influenced by the processing conditions used for formation of the regeneration matrix. A regeneration matrix produced from clotted blood inhibits fibroblast proliferation more than a regeneration matrix produced from blood collected in the presence of anticoagulants. In certain embodiments, this difference is advantageous since fibroblasts secrete collagen in wounded tissue which is necessary to some degree to provide support structure, but in most cases of severe tissue damage, the defect becomes primarily filled with a connective tissue scar. Extensive connective tissue scaring is inhibitory to the regeneration process and contributes to permanent loss of function in damages tissues and organs. Thus, in certain embodiments, the magnitude of regeneration matrix activity is modulated or controlled to provide optimal wound healing characteristics, based on the severity of the tissue damage at the wound site.

Using in vivo models of spinal cord injury, regeneration matrices of the present invention have been demonstrated to exhibit multiple beneficial effects including, but not limited to, angiogenic properties, axon growth, reduced lesion size and number, as well as an inhibitory function on formation of astrocyte glial scars. In vivo, a regeneration matrix is typically degraded over time (e.g., usually about 4-8 weeks), primarily by macrophage ingestion, although regeneration matrices of the present invention are not limited to such degradation times or mechanisms. As is clear from the present description, such degradation may occur through any of a variety of mechanisms including, but not limited to, cellular activity (e.g., through the action of macrophages), mechanical, chemical, metabolic and/or enzymatic degradation. In certain embodiments, such degradation of the regeneration matrix stimulates macrophages to display further regenerative properties themselves (e.g., through their transdifferentiation into von Willebrand factor-positive endothelial-like cells). When implanted into damaged, missing, or cut out portions of tissue or organs, regeneration matrices of the present invention support the regeneration and formation of new tissue and helps restore the functionality of the damaged or missing portion of the tissue or organ. Non-limiting examples of tissues into which the a regeneration matrix may be implanted to initiate, increase, support, and/or direct tissue regeneration and tissue formation include damaged, missing or cut out portions of the liver, kidneys, pancreas, heart, ovaries, thyroid gland, brain, spinal cord, and other neural tissue.

In the context of spinal cord regeneration, a regeneration matrix may be implanted with or without cells such as, for example, neural stem cells, neural progenitor cells, and/or differentiated neural cells, into the damaged, degenerated, missing, or cut out portion of the spinal cord. The functionality of a regeneration matrix can be further expanded or manipulated by the addition of one or more therapeutic agents including, but not limited to, growth factors, cytokines, drugs, and/or other components. In certain embodiments, when a regeneration matrix is produced without the addition of exogenous therapeutic agents, partial functionality is observed in terms of neural process extension and neural gene up-regulation. In such embodiments, the magnitude of these functions is enhanced by the incorporation of exogenous therapeutic agents during formation of a regeneration matrix. Non-limiting examples of desirable additional therapeutic agents include growth factors such as bFGF, EGF, BDNF, and/or NGF. In certain embodiments, regeneration matrix implantation into injured spinal cords leads to functional recovery of motor function loss in as little as 4 weeks after implantation.

The formation of an implantable degradable biological scaffold with inherent and multifaceted regenerative properties, which scaffolds are encompassed by certain embodiments of the present invention, is completely unprecedented. Although some cell types have produced simple extracellular matrices, such matrices appear to be of a structural nature only. No one has ever reported the production of a self-assembling matrix or scaffolding material that structurally and biologically facilitates, supports and aids in the regeneration and growth of new tissue, which matrix or scaffolding material is encompassed by certain embodiments of the present invention.

EXAMPLES

Example 1

Derivation of Regeneration Matrix from Whole Clotted Blood

Venous blood was procured from healthy donors (Research Blood Components, Brighton, Mass.) in 12 ml vaccutainers®, allowed to clot at RT for at least 30 min and frozen at −20 C until use. Processing was initiated by subjecting the blood to 5 freeze (−20 C)— thaw (RT) cycles. The contents of the vaccutainer containing 10 ml of blood were emptied into a sterile mortar. The clot was disrupted by manual grinding using a sterile pestle with the addition of process medium which consisted of a 1:1 mixture of DMEM (Mediatech, Hemdon, Va.) and Ham's F12 (Mediatech) supplemented with 2×ITS supplement (Gibco/Invitrogen, Gaithersburg, Md.), 20 ng/ml recombinant human EGF (R&D Systems, Minneapolis, Minn.), and 40 ng/ml recombinant human bFGF (R&D Systems). During the grinding procedure, liquid containing liquefied whole blood clot and process medium was aspirated from the mortar using a sterile 25 ml serological pipette and transferred to a 40 µm mesh filter where the contents were allowed to filter by gravity into a sterile 50 ml conical centrifuge tube. Fresh process medium was added to the remaining solid clot and the process repeated until the entire clot was liquefied and a final volume of 200 ml was reached. The tubes were centrifuged at 500×g for 30 min, and the supernatant filtered though a 5 µm syringe filter (Pall/Gelman) directly into Opticell® cassettes. The Opticell® cassettes were incubated at 37 C and 7.5% $CO_2$. After 6 to 8 days of incubation, 3 ml of fresh process medium was added to each Opticell® cassette. After that, 1.5 ml of fresh process medium was added every alternate day until the regeneration matrix was harvested for further analysis. The regeneration matrix formed using this method has adhesive properties in that it must be harvested by removing the top membrane of the Opticell® cassette and scraped from the bottom membrane.

Example 2

Derivation of Regeneration Matrix from Whole Blood Collected Using Anticoagulant Venous blood was procured from healthy donors (Research Blood Components, Brighton, Mass.) in 12 ml vaccutainers® containing Na$_4$-EDTA and frozen at −20° C. until use. Processing was initiated by subjecting the blood to 5 successive freeze (−20° C.)—thaw (RT) cycles. The contents of the vaccutainer containing 10 ml of blood was emptied into a sterile container and process medium (see Example 1) added to a final volume of 200 ml and the solution mixed gently. This starting material was gravity filtered through a 40 μm mesh strainer. The filtrate was collected and centrifuged at 500×g for 30 min and the supernatant passed through a 5 μm syringe filter directly into Opticell® cassettes at 10 ml each. The Opticell® cassettes were incubated at 37° C. and 7.5% CO$_2$ in air. After 6 to 8 days of incubation, 3 ml of fresh process medium was added to each Opticell® cassette. After that, 1.5 ml of fresh process medium was added every alternate day until the regeneration matrix was harvested for further analysis.

In another experiment, venous blood was procured from healthy donors (Research Blood Components, Brighton, Mass.) in 12 ml vaccutainers® containing Na$_4$-EDTA and kept on ice. The contents of the vaccutainer containing 10 ml of blood was emptied into a sterile container and process medium (see Example 1) added to a final volume of 200 ml and the solution mixed gently. This starting material was filtered through 5 μm syringe filters. The filtrate was collected and centrifuged at 500×g for 30 min and the supernatant passed through a 5 μm syringe filter directly into Opticell® cassettes at 10 ml each. The Opticell® cassettes were incubated at 37° C. and 7.5% CO$_2$. After 6 to 8 days of incubation, 3 ml of fresh process medium was added to each Opticell® cassette. After that, 1.5 ml of fresh process medium was added every alternate day until the regeneration matrix was harvested for further analysis.

The regeneration matrix formed using these methods has weak adhesive properties and can be harvested by aspiration through an 18 gauge needle using one of the access ports of the Opticell® cassette.

Example 3

Derivation of Regeneration Matrix from Whole Blood Fractions Produced Using a Serial Filtration The activity of the regeneration matrix was further refined by passing the supernatant from the centrifugation step (as listed in Examples 1 and 2) through 5 μm and 1.2 μm filter sets coupled together. This step removes larger particles from the starting material which results in altered functional properties. An example of the regeneration matrix structure within the Opticell® cassette is shown (FIG. 3). FIG. 4 shows that a regeneration matrix produced from whole blood does not show any indication of intact cells or nuclei. Hematoxylin staining was completely negative in all section analyzed but the material stains strongly with eosin. A beaded structure can be clearly resolved when using high numerical aperture lenses (high resolution). Besides the beaded structure which comprises most of the regeneration matrix, it is possible to observe small regions of flat sheets that seem to be composed of more compact structures.

Example 4.1

Scanning Electron Microscopy (SEM) of Regeneration Matrix

For electron microscopy, a regeneration matrix produced by methods described in Examples 1, 2, and 3 were fixed with 2.5% glutaraldehyde in 0.1M sodium cacodylate buffer (Electron Microscopy Sciences) at 4 C for 16 hrs. Fixations were done directly in the Opticell® by substituting the culturing medium with 10 ml of the fixative solution. The next day the fixative was removed and PBS (10 ml) was added to the Opticell®. The Opticell® was opened with a scalpel and the Opticell® membrane with the regeneration matrix attached to it was cut into small pieces 0.5×1 cm. The pieces were placed in a 1.5 ml microcentrifuge tube and post-fixed with 1% Osmium Tetroxide in water for 2 hr. The sample was then immediately placed in a 50% ethanol solution for 2 min and serially dehydrated in 70, 80, 90, 95 and 100% ethanol solutions. After the last ethanol step the samples were kept at −20° C. until shipped to the Central Microscopy Core Facility at the University of Massachusetts Amherst. The samples were critical point dried and sputter coated. Samples were imaged with a JEOL JSM-5400 Scanning electron microscope at magnifications from 100× to 7500×. Images were acquired via a digital interface to a computer and exported as TIFF format at 640×480 pixels resolution.

Each of the preparation methods yielded a regeneration matrix with different microstructure (FIGS. 5, 6, and 7). The lower porosity filtration yielded a similar overall morphology, however, the size of the spheres was lower for the 1.2 μm treatment (1-2 μm diameter, FIG. 6) that that of the 5.0 μm treatment (2-3 μm diameter, FIG. 5). A regeneration matrix produced using coagulated blood went through a maturation phase from about 2 to 3 weeks of incubation where there was an appearance of a wave-like structure on the upper surface of the matrix. A regeneration matrix produced with non-clotted blood does not develop this appearance, however, the spherical structures aggregate together to form a continuous structure that has approximately 100 nm fibers interspersed throughout (FIG. 7).

For histology, the regeneration matrix was fixed with 2.5% glutaraldehyde in 0.1M sodium cacodylate buffer (Electron Microscopy Sciences) at 4° C. for 16 hrs. Fixations were done directly in the Opticell® by substituting the culturing medium with 10 ml of the fixative solution. The next day the fixative was removed and PBS (10 ml) was added to the Opticell®. The Opticell® was opened with a scalpel and the Opticell® membrane with the regeneration matrix attached to it was cut into small pieces 2×2 cm, and mounted in between sponges in a tissue histology cassette. The samples were placed in 70% ethanol and sent for standard histological processing by Mass Histology (Worcester, Mass.). The samples were dehydrated in an ethanol series, embedded in paraffin, oriented and sectioned. Sections were stained for hematoxylin eosin using conventional fixation conditions. Images were acquired with dark field optics using a modified Leica Microscope, optimized with Richardson technologies for contrast enhancement and noise reduction. Images were collected with 20, 40 and 100× with a video camera 640×480 pixels resolution. A sample image collected at 100× magnification is shown (FIG. 8). The regeneration matrix stains with eosin and not hematoxylin.

Example 4.2

Transmission Electron Microscopy (TEM) of Regeneration Matrix

A 21 day old regeneration matrix prepared from a tissue sample that was passed through a 5 μm filter was sectioned and scanned by TEM (FIGS. 9-11). TEM analysis reveals that the sphere-like particles are part of a continuous material since under the TEM they do not show boundaries between them. The spheres are solid and not hollow and they do not have a membrane or any other type of structure surrounding them. The interior of this material is homogenous. The very dark spots in FIG. 9 are background from staining.

Example 5

Biochemical Characterization of Regeneration Matrix

Regeneration matrices made from whole blood were analyzed for protein, lipid, nucleic acid and carbohydrate content and for metabolic activities as a sensitive indicator for the presence of viable cells. Biochemical data were normalized to mass in grams of wet regeneration matrix analyzed. Standard methods for quantification of protein, DNA, RNA, and lipid were used and the composition of several different lots of regeneration matrix determined at multiple time points in the regeneration matrix manufacturing process (detailed methods are given in the individual sections).

5.1. Regeneration Matrix Total Protein Content

The most abundant biological constituent of the regeneration matrix is protein, being represented at 8.8±1.2% by mass with the remaining mass being regeneration matrix associated fluid. Normalized protein content in the regeneration matrix was determined by solubilizing a pre-weighed aliquot of a regeneration matrix in SDS lysis buffer (150 mM NaCl, 50 mM Tris-HCl (pH. 7.5), 10 mM EDTA, 1% SDS, and Completec mini protease inhibitor cocktail (Cat. # 11-836-153, Roche). The protein concentration in the lysate was determined using a Lowry based protein assay kit (Cat. # 500-0112, Bio-Rad) according to the manufacturer's instructions. A standard curve was constructed using BSA standard (Cat. # 500-0007, Bio-Rad). Optical Density (750 nm) was measured using a Spectramax Plus (Model 384, Molecular Devices) spectrophotometer and sample protein concentration was determined by interpolation of the standard curve linear range using Softmax Pro software (Molecular Devices).

The total protein content (per regeneration matrix) was determined for the regeneration matrix starting material (O) for samples harvested at days 0, 15 and 21 from the initial seeding of OptiCell® cassettes.

TABLE 1

Total protein content of regeneration matrix in the Opticell® cassette.

| Time Point (days) | Protein Content (mg) |
|---|---|
| 0 | 80 ± 25 |
| 15 | 49 ± 7 |
| 21 | 51 ± 12 |

Regeneration matrix production fluid was removed and the regeneration matrix solubilized in SDS buffer and total protein content determined. For each time point, 4 Opticell® cassettes were sampled and analyzed. Results from 4 independent batches of regeneration matrix production are reported as mean ± standard deviation.

5.2. SDS Page Analysis of Regeneration Matrix

The major species of proteins present in the regeneration matrix were determined by mass spectroscopy on all visible Coomassie bands excised from a reducing SDS-PAGE gel. For SDS-PAGE, the samples were prepared and quantified as above and loaded into pre-cast polyacrylamide gradient gels (PAGE 4-20% gradient, Cat # 345-0033, Bio-Rad) at 10 μg per well. The major protein bands were visualized by staining with Simply Blues gel stain (Cat. # LC6060, Invitrogen).

The excised protein bands were sent to Midwest Bio Services (Overland Park, Kans. (www.midwestbioservices.com) for identification. Briefly; reduction, alkylation, and in-gel trypsinization was followed by peptide extraction and separation on a microcapillary reverse-phase column. Peptides were eluted and electrosprayed directly into an LCQ Deca XP Plus ion trap mass spectrometer. Full MS spectra as well as MS/MS spectra were acquired, and the data was analyzed by TurboSEQUEST software. Since this type of analysis uses the mass of peptides to reference back the known molecular weight of peptide fragments of known proteins, the presence of partially degraded proteins would also be detected in the gel bands. The major protein species identified in the regeneration matrix are listed below: transferrin, serum albumin, serum albumin precursor, complement component 3, chains A-D hemoglobin, IgM, IgG1, medullasin inhibitor 2, carbonic anhydrase, and CA 1 protein.

A consistent protein banding pattern was observed in samples from all batches (51-56) at both, day 15 and 21. The majority of the protein was resolved at low molecular weights (approximately 67%<10 KDa), approximately 15% at 33 KDa and the remaining approximately 19% at molecular weights between 34 and 103 KDa. A photograph of the SDS gel is shown in FIG. 12.

5.3. Regeneration Matrix Nucleic Acid Content

DNA was purified and quantified from the regeneration matrix (M) and compared to starting material (O) for time points 0, 15, 21, as for protein. A measured amount of sample was lysed using 2×SDS/Proteinase K lysis buffer (40 mM Tris-HCl [pH 8.0], 50 mM EDTA, 200 mM NaCl, 2% SDS, and 6 μl Proteinase K stock (20 mg/ml, Cat # 25530-049, Invitrogen) and incubated overnight at 50° C. The lysate was extracted with an equal volume of Tris-HCl saturated phenol-chloroform-isoamyl alcohol (PCI, 25:24:1, pH 8.0), a drop of Phase Lock Gel ((PLG, Cat. # 955 15 403-7, Eppendorf). Samples were centrifuged at 14,000 g for 10 min at 4° C. to separate the phases. The aqueous phase was transferred to a new 2.0 ml microcentrifuge tube with PLG and the extraction and centrifugation repeated. The aqueous phase was transferred to a new 2.0 ml microcentrifuge tube with PLG and extracted with an equal volume of chloroform and centrifuged at 12,000×g for 10 minutes at 4° C. The aqueous phase was transferred to a fresh 1.5 ml microcentrifuge tube and DNA precipitated by adding 0.7 volume of Isopropanol (Cat. # 3032-06, Mallinckrodt) and 10 μg glycogen (Cat # 10901393001, Roche) and letting stand at RT for 15 min. The samples were centrifuged for 20 minutes at 14,000×g at 4° C. The pellets were washed 2× with 0.5 ml 70% ethanol (Cat # EX0289-1, EM Science), air dried, and re-suspended in 30 μl TE buffer, pH 8.0. The concentration of DNA was determined by spectrophotometric measurement (Spectra Max Plus, Model 384, Molecular Devices) of the optical density (OD) at 260 nm. The OD 260/280 ratio was also determined to indicate the level of protein contamination in the DNA isolation. The total DNA content (μg) of the regeneration matrix at 15 and 21 days was compared to that in the starting material at time 0.

TABLE 2

Total DNA content of regeneration matrix in the Opticell® cassette.

| Time Point (days) | DNA Content (μg) |
|---|---|
| 0 | 8 ± 18 |
| 15 | 7.8 ± 2.0 |
| 21 | 6.6 ± 3.3 |

Regeneration matrix production fluid was removed and the R regeneration matrix solubilized in SDS buffer and total DNA content determined. For each time point, 4 Opticell® cassettes were sampled and analyzed. Results from 4 independent batches of regeneration matrix production are reported as mean ± standard deviation.

RNA was isolated from the regeneration matrix (M) and compared to that from starting material (O) for time point 0, 15, and 21 using Trizol reagent (Cat. # 15596-018, Invitrogen). One 1.0 ml of Trizol was added to a predetermined quantity mass and allowed to stand at RT until solubilized (10-20 min). The samples were centrifuged at 12,000×g for 10 minutes at 4° C. and the aqueous layer was transferred to a new 1.5 ml microcentrifuge tube. The solution was extracted with 200 µl of chloroform (Cat. # 4440-04, Mallinckrodt) and centrifuged at 12,000×g for 20 minutes at 4° C. The aqueous phase was transferred to a new 1.5 ml microcentrifuge tube and RNA was precipitated by adding 500 µl of isopropyl alcohol (Cat #3032-06, Mallinckrodt) and centrifugation at 12,000×g for 30 minutes at 4° C. The RNA pellet washed in 75% ethanol, centrifuged at 7,500×g for 5 min at 4° C., air dried, and re-suspended in 25 µl of RNase free water by heating the sample at 65° C. for 15 min. RNA was quantified by OD at 260 nm using a spectrophotometer (Spectramax, Model 384, Molecular Devices). The total RNA content (µg) of the regeneration matrix at 15 and 21 days was compared to that in the regeneration matrix starting material at time 0.

TABLE 3

Total RNA content of regeneration matrix in the Opticell ® cassette.

| Time Point (days) | RNA Content (µg) |
| --- | --- |
| 0 | 1551 ± 1145 |
| 15 | 184 ± 29 |
| 21 | 96 ± 43 |

Regeneration matrix production fluid was removed and the regeneration matrix solubilized in SDS buffer and total RNA content determined. For each time point, 4 Opticell ® cassettes were sampled and analyzed. Results from 4 independent batches of regeneration matrix production are reported as mean ± standard deviation.

5.4. Regeneration Matrix Lipid Content

Total lipid content in the regeneration matrix (M) was compared to that in starting material (O) for time points 0, 15, and 21 using the Bligh and Dyer method (Bligh, E. G., and Dyer, W. J., A rapid method of total lipid extraction and purification, Can. J. Biochem. Physiol. 37, 911-917, 1959). Prior to analysis samples were stored frozen at −85° C. and thawed at RT at the time of analysis. For the regeneration matrix, 375 µl of methanol:chloroform (2:1 v/v) was added to the pre-weighed sample and incubated at RT for 15 min in a vortexer (Digital mini vortexer, Cat. # 14005-824, VWR) at medium speed). Then, 475 µl of methanol:chloroform:water (Cat. # IB05174, IBI Shelton) mixture was added and incubated at RT 15 min in a vortexer as above. The samples were centrifuged at 250×g for 10 minutes at RT. The liquid phase (both chloroform and water phase) was transferred into a fresh 1.5 ml microcentrifuge tube leaving only the regeneration matrix pellet in the tube. The regeneration matrix pellet was re-suspended in 475 µl of 2:1:0.8 methanol:chloroform:water mixture and extracted again by vortexing for 15 minutes at medium speed. 125 µl of chloroform was added and the samples vortexed for 2 minutes, 125 µl water added and the samples vortexed for another 2 minutes, then centrifuged at 250×g for 10 minutes at RT. The liquid phase was pooled into the sample from the original extraction and centrifuged at 1,000×g for 10 minutes at RT. The chloroform phase was transferred to a fresh 1.5 ml microcentrifuge tube and dried in a vacuum dryer for 45 minutes or until the chloroform was completely evaporated. 50 µl of chloroform was added to the dried lipid pellet and the samples vortexed for 15 to min to solubilize the lipid completely. The samples were stored at −85° C. until the final analysis. A dilution series of standard lipid (L4646, Sigma) was constructed and the samples hydrolyzed by adding 1011 of extracted lipid sample to 500 µl concentrated sulphuric acid (Cat # SX1244-6, EMD Chemicals) and boiling the tubes for 10 min. The samples were cooled in a water bath at RT for 2 min and 40 µl of sample was added to 600 µl of phosphor-vanillic reagent (0.6 g Vanillin (Cat. # VX0045-1, EM Science), 10 ml of 100% ethanol (Cat. # EX0289-1, EM Science), 90 ml dH$_2$O and 400 ml Phosphoric acid (Cat. # PX0995-6, EMD Chemicals) mixed and incubated at RT protected from light for 45 min. The lipid concentration was determined by measuring the OD at 525 nm (Spectra Max 384, Molecular Devices) and interpolation with the standard curve using SoftMax provided with the spectrophotometer. The total lipid content (µg) of the regeneration matrix at 15 and 21 days was compared to that in the starting material at time 0.

TABLE 4

Total Lipid content of regeneration matrix in the Opticell ® cassette.

| Time Point (days) | Lipid Content (µg) |
| --- | --- |
| 0 | 1.9 ± 0.4 |
| 15 | 0.02 ± 0.01 |
| 21 | 0.03 ± 0.01 |

Regeneration matrix production fluid was removed and the regeneration matrix total lipid content determined as above. For each time point, 4 Opticell ® cassettes were sampled and analyzed. Results from 4 independent batches of regeneration matrix production are reported as mean ± standard deviation.

The results of the analyses for nucleic acids and lipids suggest that these materials are present in the starting material and are degraded over time. The initial degradation rate seems to be variable with the high degree of variation in the amount of DNA and RNA detected in the starting material at time zero. This variability among different samples decreased with time by days 15 and 21. In no case was there an increase in any of these components which give further evidence that cellular activity is not present.

Example 5.5

Radiolabel Substrate for Protein and Nucleic Acid Synthesis During Formation of Regeneration Matrix To establish whether the formation of the regeneration matrix involves active basic cellular processes (DNA, RNA, protein synthesis), regeneration matrix starting material was incubated with tritiated substrates for DNA, RNA, and protein synthesis. Five Opticells® containing starting material were incubated with radioisotope labeled substrates, one Opticell® for each substrate. The substrates used were $^3$H-L-amino acid mixture (1 mCi/ml, Cat. 20063, MP Biomedicals), $^3$H-dTTP (10-20 Ci/mmol, Cat. # 24044, MP Biomedical), $^3$H-Thymidine (60-90 Ci/mmol, Cat. # 24060 MP Biomedicals), $^3$H-UTP (35-50 Ci/mmol, Cat. # 24061, MP Biomedicals), and $^3$H-Uridine (35-50 Ci/mmol, Cat. # 24046, MP Biomedicals). For introduction to the Opticell® cassettes, 25 µl of isotope was diluted into 0.5 ml of DMEM:F-12 medium, then injected into each Opticell® and rotated to facilitate mixing. Immediately after injection and mixing, a 1.0 ml aliquot was taken out of the Opticell® (10 ml total volume) and processed for a time-zero control (see below). The Opticells® were incubated at 37° C. with an atmosphere of 5.0% CO$_2$ in air. At time points of 1, 3 and 7 days, 1.0 ml aliquots were taken for analysis. The samples were kept on ice in 1.5 ml microcentrifuge tubes and 100 µl (0.1 vol) of 100% trichloroacetic acid was added and the tubes inverted to mix the contents. Samples were incubated on ice for 20 min to precipitate nucleic acids and proteins. The precipitate was added to a GF/C filter (Whatman) in 0.1% TCA (ice cold) using a Pasteur pipette. The contents of the microcentrifuge tube were added to the filter and rinsed 5× using ice cold 0.1% TCA. The filters were placed on foil and air dried for one hour. The filter was placed into 4 ml of Scintillation Coctail (ScintiSafe, Fisher Scientific) an added to a 5 ml plastic scintillation vial. The vials were counted using a Beckman liquid scintillation counter on the tritium energy channel for one minute. The results (counts per minute) of TCA precipitatable material are reported in the table below. Cultured human fibroblasts were used as a positive control for the assay.

TABLE 5

Total counts per minute for each of the radio-labeled substrates at time zero, 1 day, 3 days, and one week after initial seeding of regeneration matrix forming material.

|  | Time | 3H-TTP DNA | 3H-Thymidine DNA | 3H-UTP RNA | 3H-Uridine RNA | 3H-AA Mix Protein |
|---|---|---|---|---|---|---|
| Total Regeneration Matrix |  | 250,781 | 248,971 | 252,367 | 253,674 | 249,875 |
| Seed Material | 0 Hr | 103 | 113 | 127 | 115 | 95 |
|  | 1 Day | 236 | 277 | 356 | 387 | 499 |
|  | 3 Days | 301 | 286 | 346 | 354 | 524 |
|  | 1 Week | 289 | 275 | 321 | 289 | 426 |
| Human Fibroblasts | 0 h | 526 | 487 | 512 | 426 | 458 |
|  | 1 Day | 14,643 | 12,473 | 27,943 | 25,784 | 69,285 |

These results indicate that there is no detectable cellular activity during the process of regeneration matrix formation.

Example 5.6

Metabolic Inhibition Studies

In the first set of experiments (see FIGS. 13 and 14), aphidicolin (dissolved in DMSO, final concentration 10 µg/ml), α-amanitin (dissolved in water, final concentration 10 µg/ml) and cyclohexamide (dissolved in ethanol, final concentration 10 µg/ml) were used to inhibit DNA polymerase, RNA II polymerase and protein synthesis activity, respectively, in regeneration matrix produced from whole blood. The inhibitors were added on day 0 to the Opticells® on the day of first feeding (day 5 or 6). Thereafter, cultures were fed with regular media. Samples from the respective treatments and controls were collected on day 21 and analyzed.

Results for these inhibition studies are presented in FIGS. 13-16. Fibroblast control cultures containing 0, 10, 30 and 100 nM of α-amanitin were cultured for one week. Fibroblasts without added α-amanitin were confluent by day 7. Cultures containing 10, 30 and 100 nM α-amanitin exhibited about 60-70%, 80-90% and 100% mortality respectively by day 7.

In another set of experiments, addition of apyrase (dissolved in water, final concentration 10 µg/ml), an ATPase/ADPase, indicated that it was able to partially prevent matrix formation in 5 µm filter samples. Apyrase has two functions: on the one hand it has an ATPase/ADPase activity, while on the other, it has an anticoagulant activity. It is possible that components present in 5 µm filtered samples are susceptible to the anticoagulant activity of apyrase resulting in the "sedimentation" observed in those cultures. The absence of "sedimentation" in 1 µm filtered samples may possibly be due to the elimination of these components retained by the small-pore size of the filter.

Example 5.7

Fatty Acid Analysis

Mass spectrometry analysis was performed to determine the fatty acid content in a 3 week old regeneration matrix cultures made from whole blood that had been filtered through a 5 µm or 1 µm filter. As can be seen from Table 6, a number of the fatty acid species detected were absent in the supernatant and present exclusively in the matrix. The proportion of fatty acid per mg lipid was higher in the 1 µm filtered sample compared to 5 µm filtered for the matrix. This proportion was reversed for the supernatant. Since the presented data is based only on one sample and one analysis, no conclusion could be drawn at this stage.

TABLE 6

Results of fatty acid analysis on 3-week old regeneration matrix (made from whole blood) and supernatant by Folch partition, represented as µg/mg lipid.

| | | Matrix | | Supernatant | |
|---|---|---|---|---|---|
| Structure | Name | 5µ filtered | 1µ filtered | 002S | 003S |
| 14:0 | Myristic acid | 16.32 | 24.80 | 1.69 | — |
| 15:0 | Pentodecyclic acid | 1.27 | 3.19 | 0.81 | 0.03 |
| 16:0 | Palmitic acid | 29.33 | 82.65 | 7.82 | 0.44 |
| 16:1 | Palmitoleic acid | 1.62 | 18.92 | — | — |
| 17:0 | Margaric acid | 1.64 | 2.38 | 0.56 | 0.29 |
| 18:0 | Stearic acid | 15.24 | 44.00 | 1.76 | — |
| 18:1 | Oleic acid | 15.21 | 38.38 | 4.75 | 0.69 |
| 18:2 | α-linoleic acid | 3.41 | 10.40 | 1.62 | 0.38 |
| 18:3 | α-linolenic acid | 1.44 | — | — | 0.08 |
| 20:0 | Arachidic acid | 0.5 | 1.34 | — | — |
| 20:1 | Gadoleic acid | 0.48 | 0.75 | — | — |
| 20:4 | Arachidonic acid | — | 3.02 | — | — |

TABLE 6-continued

Results of fatty acid analysis on 3-week old regeneration matrix (made from whole blood) and supernatant by Folch partition, represented as µg/mg lipid.

| | | Matrix | | Supernatant | |
|---|---|---|---|---|---|
| Structure | Name | 5µ filtered | 1µ filtered | 002S | 003S |
| 21:0 | Heneicosanoid acid | — | 0.17 | — | — |
| 22:0 | Behenic acid | 0.81 | 2.10 | — | — |
| 22:6 | Nisinic acid | 1.79 | 2.49 | — | — |
| 23:0 | Tricosanoic acid | 0.31 | 0.84 | 0.58 | — |
| 24:0 | Tertracosanoic acid | 1.76 | 5.14 | — | — |
| 24:1 | Nervonic acid | 1.20 | 3.76 | — | — |
| | Total fatty acid in the sample | 92.13 µg/mg | 244.33 µg/mg | 19.59 µg/mg | 1.92 µg/mg |

Example 5.8

Osmolarity

Osmolarity of frozen samples from supernatants of two different cultures were analyzed for different time periods. It is evident from Table 7 below that there is a dramatic increase in the osmolarity as the cultures age.

TABLE 7

Osmolarity measurements of regeneration matrix cultures.

| Sample ID | Time 0 | 14 days | 21 days | 28 days | 42 days | 56 days |
|---|---|---|---|---|---|---|
| 1 | 314 | — | 420 | 437 | 532 | 528 |
| 2 | 311 | 406 | 440 | — | — | — |

Example 5.9

Analysis of Regeneration Matrix for ATP Driven Metabolic Activity

Regeneration matrix and its associated production fluid were assayed for levels of adenosine triphosphate (ATP) at 2, 3, 4, 6 and 8 weeks of age and compared these levels with levels of ATP in the starting material. ENLITEN ATP Assay system was used for rapid and quantitative detection of ATP by luminescence. Material was SDS extracted and precipitated with TCA, as suggested by the manufacturer. In addition, presence of several metabolic enzymes was examined in same samples using Western blotting. For ATP level, the detection reactions were performed in triplicate and assayed on three different days. The starting material of three batches of regeneration matrix contained picomolar amounts ($1 \times 10^{-12}\ mol$) of ATP, while ATP became undetectable at day six of culture and remained undetectable for all the subsequent culture time points.

The presence the metabolic enzymes glucose-6-phosphate dehydrogenase, aldolase, pyruvate dehydrogenase and cytochrome reductase was evaluated using Western blotting. Aldolase, an enzyme catalyzing glucose degradation through glycolysis, was present in the starting material and was detected at decreasing levels between 21 and 28 days of incubation and was not detectable at 60 days. Glucose-6 phosphate dehydrogenase (pentose phosphate pathway) was detected in the starting material and was over time be detected predominantly in the regeneration matrix associated production fluid. The levels in the regeneration matrix dropped by day 28 and remained low for the remainder of culture. However, the band on the gel for this enzyme was a lower molecular weight suggesting that only a degraded from was detected. Pyruvate dehydrogenase (Krebs cycle) was detectable in the starting material and levels did not appear to change until day 28. Again, the band was a lower molecular weight than that predicted suggesting that a degradation product was being detected. This enzyme could not be detected at any later time points. Cytochrome reductase (Oxidative phosphorylation) was detected in the starting material and a faster migrating protein (absent in the starting material) was recognized at all the subsequent time points suggesting a degradation product being detected in the regeneration matrix.

Absence of detectable levels of ATP in the regeneration matrix as early as 6 days after initial seeding supports the conclusion that these enzymes are not functional. Both, pyruvate dehydrogenase and cytochrome reductase catalyze reactions that produce massive amounts of ATP (36 ATPs per reaction).

Example 5.10

Other Analysis

Compositional analysis of the matrix indicates there is no evidence for cellular metabolic activity in the regeneration matrix. The pH of the culture medium remains constant throughout the culture, thus indicating very low or no metabolic activity. Furthermore, the osmolarity of the culture medium increases dramatically over the culture period making the conditions non-permissive for cellular growth.

A comparison of coomasie stained SDS-PAGE gels revealed minor differences in band patterns between 5 µm and 1 µm filtered samples. Gel images are presented in FIG. 17. The band designations in blue represent bands that were previously identified by mass spectrometry. The new bands indicated by the red circle (M7 and M8) are bands that have only been observed in the 1 µm filtered matrix. The appearance of these bands may be due to enrichment of certain bands resulting from removal of other proteins. The sensitivity of regeneration matrix to different proteases and nucleases were tested. Nucleases such as DNase and RNase had no effect on the regeneration matrix. Proteolytic enzymes such as pepsin, trypsin, papain, Proteinase K were able to digest the matrix.

Example 6

Activation of Neurotrophic Genes In Vitro Using Regeneration Matrix

Human neuroblastoma cells (Cell Line SH-SY5Y, Cat. # CRL-2266, American Type Tissue Culture Collection, Manassas, Va.) were used to characterize the neurotrophic activity of the regeneration matrix. Cells were cultured using the following basal medium (BM): DMEM:F12 (Cat. #30-2006, ATCC) supplemented with 10% FCS (Cat. #26140-079, Invitrogen), and 5 µg/ml Gentamycin antibiotic (Cat. #15710064, Invitrogen), and were amplified and routinely maintained by passage at confluence using T125 tissue culture flasks.

For analysis of gene induction, cells were trypsinized and seeded into T75 flasks at $10^5$ cells/ml, 3 days before addition of starting material. Materials tested were basal medium (BM), matrix medium (R), OptiCell® starting material (O) and regeneration matrix (M). To inactivate liquid test material, OptiCell® starting material (O) was placed into 15 ml conical polystyrene culture tubes and heated to 60° C. for 30 min. To inactivate the regeneration matrix, the regeneration matrix associated fluid was removed from the OptiCell® and the regeneration matrix washed three times (10 ml each) with PBS (Cat. # 21-030-CM, Mediatech). 10 ml of formalin (3.7% formaldehyde, Cat. # 2106-01, JT Baker in PBS) was added to the OptiCell® containing the regeneration matrix and incubated for 30 minutes. The regeneration matrix washed 3× with PBS and stored in PBS until harvested for experiments.

For regeneration matrix treatments (active or fixed), the entire contents of the OptiCell® was added to a T75 culture flask containing 70% confluent SH-SY5Y neuroblastoma cells. After 3 hours, cells were washed with PBS and harvested by scraping the cells and pipetting into a 2.0 ml microcetrifuge tube. Cells were centrifuged at 12,000 RPM and supernatant discarded. Total cellular RNA was isolated using an Atlas Total RNA Isolation kit (Cat. # K1036-1, BD Biosciences, formerly Clontech) according to the manufacturers instructions. RNA pellets were dissolved in RNase-free $H_2O$ and quantified by $OD_{260}$. RT-PCR was performed using an Ambion Retroscript Kit (Cat. # 1710, Ambion, Austin, Tex.) according to the manufacturers instructions using 2 µg of RNA template. Primers specific for human glyceraldehyde-3-phosphate dehydrogenase (GAPDH), growth associated protein 43 (GAP-43), netrin-1, neural cell adhesion molecule (NCAM-1), neurotrphin-3 (NT-3), neurotrophin-6 (NT-6), glial derived neurotrophic factor (GDNF), and fibroblast growth factor-9 (FGF-9) were used for RT-PCR. GAPDH was used as a control since its transcription should not be affected by the type of stimulation used in this assay. The primers used were the following:

```
GAPDH      5' CCTGCACCACCAACTGCTTAG
           5' AGACCACCTGGTGCTCAGTGT

GAP-43     5' AAAGTGCCCGGCAGGACGAGGGTAAAGA
           5' GAAAGTGGACTCCACAGGGCCACACG

NT-3       5' AAGGAGTTTGCCAGAAGACTCGCTCAATTCC
           5' CACGTAATCCTCCATGAGATACAAGGGCGG

NT-6       5' CCCGGACCGCTGTGGACTTGGTTG
           5' GTATAAGTCTCAGGCCCGGCCAGTC

Netrin-1   5' GCAGTCTGCCACTTGGAAGGA
           5' GCCATATTGCGTAGGCGAGGT

NCAM       5' CACAGCCATCCCAGCAACCTTGGG
           5' GGGCAAACTCCTTATGAAGTGGCACAAA

GDNF       5' AAATGTCACTGACTTGGGTCTGGG
           5' GACAGGTCATCATCAAAGGCGATGGG

FGF-9      5' CGCCTAATATCTCCTGGGTTGACACC
           5' AATGCCAAATCGGCTGTGGTCTTTCC
```

For PCR, 5 µl of RT reaction product was added to 45 µl of PCR reaction cocktail (5 µl of 10×PCR Buffer, 100 mM Tris-HCl pH 8.3, 500 mM KCl, 15 mM $MgCl_2$, 2.5 µl of 2.5 mM dNTP mix, 32.1 µl d $H_2O$ (nuclease-free), 2.5 µl each of sense and anti-sense 10 µM primer stock, 0.4 µl of 5 U/µl Taq Polymerase (Cat. # 2052, Ambion). PCR parameters were: 94° C. for 2 min (initial denaturation), followed by 30 Cycles of 94 C for 30 sec, 55° C. for 30 sec, and 72° C. for 40 sec, with a final polishing step of 72° C. for 5 min. PCR products were resolved using 10 µl of PCR product per well on 2.5% agarose gels run for 2 hrs at 58 V and stained with ethidium bromide at 0.5 µg/ml. Digital images of the gels were analyzed for fold up-regulation using Scion image analysis software (Scion, Frederick, Md.). The band intensity of the lane containing the RT-PCT product of RNA produced from adding medium alone was used to normalize the signals from the other treatments (data not shown).

The RT-PCR analyses showed genes for FGF-9, Netrin-1, NT-3, NCAM-1, and GAP-43 are activated in response to incubation with regeneration matrix. Gene activation by the regeneration matrix appears selective as transcription for the genes for GAPDH, NT-6 and GDNF were not stimulated in these experiments. These data indicate that the human neuroblastoma cell line SH-SY5Y responds selectively to the regeneration matrix with the activation of genes related to function and differentiation. Production medium supplemented with growth factors alone gave a marginal increase in gene up-regulation activity compared to medium alone for FGF-9 and Netrin-1 only. These results suggest that the gene up-regulation activity of the regeneration matrix is due to its inherent properties and not merely the presence of growth factors.

Activation of NT-3, NCAM-1, Netrin-1, GAP-43, and FGF-9, gene expression by the regeneration matrix in SH-SY5Y cells can be inactivated by treating the matrix at 60° C. for 30 minutes (FIG. 19). Finally, treatment of the regeneration matrix with formalin or with high energy gamma irradiation (30 kGy, 30 min) also inactivates the regeneration matrix (data not shown).

For routine analysis, the effect of the regeneration matrix on up-regulation of GAPDH (control), GAP-43, NCAM-1, and NT-3 was determined for four consecutive production batches. A regeneration matrix from each batch was sampled at day 15 and 21 and compared to the gene induction activity of starting material (Table 8). Fold up-regulation was determined by RT-PCR from 4 production runs (2 Opticell® cassettes per time point). Results are reported as mean±standard deviation.

TABLE 8

Average fold up-regulation of GAPDH, NT-3, NCAM-1, and GAP-43 in SH-SY5Y neuroblastoma cells following incubation with regeneration matrix at days 0 (starting material), 15, and 21 of production.

| Time (days) | GAPDH | NT-3 | NCAM-1 | GAP-43 |
|---|---|---|---|---|
| 0 | 1.1 ± 0.1 | 2.5 ± 0.2 | 2.9 ± 0.3 | 3.0 ± 0.3 |
| 15 | 0.9 ± 0.1 | 3.9 ± 1.1 | 4.4 ± 1.7 | 4.7 ± 1.8 |
| 21 | 1.0 ± 0.2 | 4.5 ± 1.9 | 4.7 ± 2.2 | 5.6 ± 3.0 |

Example 6.1

Effect of Regeneration Matrix Produced without Growth Factor Supplements on Gene Induction in Human Neuroblastoma Cells A regeneration matrix was produced using DMEM:F12 medium alone without any growth factor supplementation.

The gene up-regulation response in SH-SY5Y neuroblastoma cells for GAPDH, NT-3, NCAM-1, and GAP-43 was compared to a regeneration matrix produced with ITS (2×), EGF (20 ng/ml), and bFGF (40 ng/ml) supplementation. The regeneration matrix produced without growth factors contains gene up-regulation activity which is not altered appreciably when it is produced in production medium with growth factor supplements (data not shown).

Example 6.2

Regeneration Matrix Neuronal Gene Up-Regulation Activity

Regeneration matrix formed for 12 days has neuronal gene up-regulation activity, while its surrounding solution (CM) as well as the initial solution (day 0) that would form regeneration matrix (Rep) has limited neuronal gene up-regulation activity. FIGS. 18A-18C show results of RT-PCR on SHSY Human Neuroblastoma Cells Treated with regeneration matrix for 3 hours. Values presented as fold up-regulation over standard control. Regeneration matrices were produced in parallel from non-coagulated (EDTA-treated) whole blood from the same human donor. A=DMEM/F12 base media with supplements (a standard regeneration matrix production media). ITS=insulin+transferrin+selenium supplement added to DMEM/F12 base media. EGF=epidermal growth factor supplement added to DMEM/F12 base media. FGF=fibroblast growth factor 2 supplement added to DMEM/F12 base media. All=ITS+EGF+FGF supplements added to DMEM/F12 base media. None=no supplements added to DMEM/F12 base media. No Feed=no additional media was added after start (day 0) of regeneration matrix formation period.

Columns A-S in FIGS. 18A-18C refer to the following regeneration matrices:
A=Complete regeneration matrix production medium;
B=Day-12, All, RM-1;
C=Day-12, All, CM-1;
D=Day-12, ITS, RM-1;
E=Day-12, ITS, CM-1;
F=Day-12, EGF-ITS, RM-1;
G=Day-12, EGF-ITS, CM-1;
H=Day-12, FGF-ITS, RM-1;
I=Day-12, FGF-ITS, CM-1;
J=Day-12, None, RM-1;
K=Day-12, None, CM-1;
L=Day-12, No Feed, RM-1;
M=Day-12, No Feed, CM-1;
N=Day-0, EGF-ITS, Rep-1;
O=Day-0, EGF-ITS, Rep-2;
P=Day-0, FGF-ITS, Rep-1;
Q=Day-0, FGF-ITS, Rep-2;
R=Day-0, None, Rep-1;
S=Day-0, None, Rep-2.

As can be seen in FIGS. 18A-18C, in every instance the regeneration matrix at day 21 exhibited increased neuronal gene up-regulation activity compared to its starting solution (day 0). The surrounding solution at day 21 continued to exhibit the limited activity as observed in the starting solution (day 0). Thus, only the formed regeneration matrix exhibited increased activity, and its formation did not result in a decreased activity of its surrounding solution. Thus, the total neuronal gene up-regulation activity of the cultures increased dramatically over time as the regeneration matrices formed.

Example 7

Effect of Regeneration Matrix on Rat Neuroscreen-1® Cells (Induction of Neurite Extension Neuroscreen® cells, an enhanced subclone from rat PC-12 pheochromocytoma cells (Tsuji, M. et al., *Induction of neurite outgrowth in PC12 cells by alpha-phenyl-N-tert-butylnitron through activation of protein kinase C and the Ras-extracellular signal-regulated kinase pathway*, J. Biol. Chem. 276, 32779-32785, 2001; Wu, Y. Y. and Bradshaw, R. A., *Synergistic induction of neurite outgrowth by nerve growth factor or epidermal growth factor and interleukin-6 in PC12 cells*, J Biol Chem 271, 13033-13039, 1996), were obtained from Cellomics (Cat. # R04-0001-C1) and incubated with a regeneration matrix. The Neuroscreen® cells responded by extending neurites. In addition, the morphology, of Neuroscreen® cells change and flatten and become more elongated in the presence of the regeneration matrix (FIG. 20).

For the Neuroscreen® cells—regeneration matrix interaction studies, cells and the regeneration matrix sample materials were prepared using the following method. Neuroscreen® cells were maintained prior to the interaction assay by routine culture on collagen coated plastic and subcultured at confluence using basal medium consisting of RPMI (Cat # 10-040-CV, Mediatech), 4.0 mM Glutamine (CAT # 25-005-CI, Mediatech) supplemented with 20% Horse Serum (Cat # 35-030-CV, Mediatech), 10% Fetal Bovine Serum (Cat #35-010, Mediatech). The day before the regeneration matrix interactions were established, cells were trypsinized, counted and plated at 2,000 cells per well in 96-well cell culture plates (BD Biosciences, Cat. # 47743-953, Axygen). The Opticell® cassettes containing the regeneration matrix were opened and the regeneration matrix was transferred to a sterile 100 µm nylon cell strainer (Cat. # 352360, BD Falcon), sieved and dispersed into 1 ml of PBS (Cat. # MT21-030-CM, Mediatech). 10 µl of dispersed regeneration matrix suspension was added to each well containing Neuroscreen® cells seeded the previous day.

For each production batch, samples were taken for the above analyses at 0, 15 and 21 days after initiation. Neuroscreen® cells were assayed for the formation of neurite process extension using immuno-staining for β-tubulin as follows. Cells were fixed after 4 days in culture by adding 10% v/v of 37% formaldehyde (Cat. # 2106-01, J. T. Baker) directly to the culture medium in the well. The plates were incubated at 37° C. for 30 min, washed 2× with PBS, permeabilized and blocked with blocking buffer (10% Normal goat serum Cat. # S26-100M, Chemicon, 5% BSA Cat. # 2910, Omnipure, 0.1% Saponin Cat. #102855, MP-Biochemicals) for 2.5 hr and stained for 16 hrs at 4° C. using anti-β-tubulin antibody (mouse monoclonal, cell culture supernatant, Cat. # E7, Developmental Studies Hybridoma Bank) diluted 1:100 in blocking buffer. Cells were washed 2× in PBS and labeled with alexa 488 Goat anti-mouse secondary antibody (Cat. # A 11029, Invitrogen) diluted 1:200 in blocking buffer. Cells were counterstained with Hoechst 33342 (Cat. # H1399, Invitrogen) at 2 µg/ml in PBS for 30 min then washed 1× with PBS. Plates were scanned with a KineticScan microscope (Cellomics, V2.2.0.0 Build 19) using neurite Outgrowth Bio-application V2.0.

Output parameters selected included, total cells, neurite outgrowth index (NOI) which is the percent of cells in a well with a total neurite length above 10 µm, and average neurite length per cell (ANL) in µm.

The positive control for this assay was the addition of nerve growth factor (NGF, Cat. # 13257-019, Invitrogen) at 100 ng/ml. In summary, the treatments used were as follows, each with and without NGF: regeneration matrix, Neuroscreen-Basal Medium, Neuroscreen-Basal Medium+100 ng/ml NGF, regeneration matrix made without growth factors.

Only wells with cell counts above 100 cells per field were analyzed. The average NOI per well was divided by the average NOI value from the positive control wells containing Neuroscreen® basal medium plus 100 ng/ml NGF. This value is reported as percent of NGF response. Data from 4 independent experiments testing for the stimulation of neurite outgrowth from Neuroscreen® cells is shown in FIG. 21. The stimulation of neurite outgrowth by the regeneration matrix made without growth factor supplements compared to that with them is shown in FIG. 22.

These results indicate that the regeneration matrix has significant neurite inducing activity when tested in Neuroscreen® cells. However, contrary to the results from gene up-regulation studies with neuroblastoma cells, the neurite outgrowth activity of the regeneration matrix can be significantly increased by the addition of ITS, EGF, and bFGF supplements during regeneration matrix production.

Example 8

Protection and Enhancement of Growth Factor Activity by Regeneration Matrix

Human peripheral blood collected into ten 8 ml Vacutainer™ tubes containing K2EDTA was shipped overnight on ice and then placed vertically into a +4° C. fridge for 6 hours in order to allow the blood to gravity separate. The Vacutainer™ tubes containing the gravity-separated blood were then carefully placed vertically into a −20° C. freezer for storage. Two days later, four of the tubes were taken out of the freezer and placed vertically into a tube stand and allowed to thaw at 20° C. Once thawed, the plasma-platelet-buffy coat fraction of two of the tubes was removed and placed into a 50 ml conical tube, and the entire contents of the remaining two tubes were placed into another 50 ml conical tube. After thorough mixing of the contents of each conical tube, 5 ml of each conical tube were placed into separate 50 ml conical tubes along with 10 ml of TR-10 media containing 100 ng/ml nerve growth factor (NGF). The TR-10 media composition is shown in Table 9. After thorough mixing of the contents of each conical tube, the solutions were filtered through a 5 µm syringe filter, followed by a 1.2 µm syringe filter and then placed into new 50 ml conical tubes. Enough TR-10 media containing 100 ng/ml NGF was added to make the contents of each conical tube equal 50 ml. After thoroughly mixing the contents of each conical tube, 10 ml quantities of the solutions were injected into separate sets of 5 Opticells™, and then placed horizontally into a 37° C., 20% CO2, 2% $O_2$, non-humidified incubator. Thus each Opticell™ received 1 µg of NGF. The samples were left untouched for 6 days, after which 3 ml of TR-10 media was added to each Opticell™. An additional 1 ml of TR-10 media was added to each Opticell™ on days 8, 10 and 12. On day 13, the contents of each Opticell™ were placed into separate 15 ml conical tubes and spun at 500×g. The supernatant was removed and saved for later analysis. The contents of each 15 ml conical tube were then washed with PBS, spun at 500×g, and the supernatant was removed and discarded. This was repeated two more times in order to remove all the original solution that each of the Regeneration Matrices were surrounded in (when they were in the Opticells™). Each Regeneration Matrix (~1 g in mass and ~1 ml in volume) was then saved for later analysis. Each Regeneration Matrix contained approximately 5 mg of protein. The level of hydration of the regeneration matrices could be almost halved when centrifuged at 5,000×g for 30 min (and the resulting liquid supernatant removed)

TABLE 9

TR-10 Composition.

| | mg/L |
|---|---|
| INORGANIC SALTS | |
| Calcium Chloride Anhydrous | 255.49 |
| Ferric Nitrate 9$H_2$0 | 0.404 |
| Magnesium Chloride 6$H_2$O | 142.31 |
| Magnesium Sulfate Anhydrous | 97.67 |
| Potassium Chloride | 400 |
| Potassium Chloride | 1491 |
| Sodium Bicarbonate | 1280.1 |
| Sodium Chloride | 6800 |
| Sodium Phosphate Dibasic 7$H_2$0 | 134.035 |
| Sodium Phosphate Monobasic | 140 |
| Sodium Phosphate Monobasic $H_2$0 | 62.509 |
| Zinc Sulfate 7$H_2$O | 0.14378 |
| OTHER COMPONENTS | |
| D-Galactose | 360.32 |
| D-Glucose (Dextrose) | 4154.602 |
| DL Tocopherol Acetate | 4.7273 |
| DL-Lipoic Acid Thioctic | 2.0632 |
| Ethanolamine HCl | 4 |
| Glutathione (Reduced) | 153.665 |
| Human Transferrin Holo | 11 |
| Insulin Recombulin Full | 20 |
| Linoleic Acid | 5.6088 |
| Linolenic Acid | 2.7842 |
| MOPS | 2092.7 |
| Putrescine 2HCl | 32.216 |
| Sodium Hypoxanthine | 2.37165 |
| Sodium Pyruvate | 55.02 |
| Sodium Selenite | 0.0134 |
| Thymidine | 0.365767 |
| AMINO ACIDS | |
| L-Alanine | 4.455 |
| Glycine | 15.014 |
| L-Arginine HCl | 147.251 |
| L-Asparagine $H_2$O | 1.501 |
| GlutaMAX ™ I | 217.23 |
| L-Histidine HCl $H_2$O | 31.445 |
| L-Isoleucine | 54.567 |
| L-Leucine | 59.158 |
| L-Lysine HCl | 91.142 |
| L-Methionine | 17.308 |
| L-Phenylalanine | 35.516 |
| L-Proline | 5.757 |
| L-Serine | 26.273 |
| L-Threonine | 53.485 |
| L-Tryptophan | 9.027 |
| L-Valine | 52.952 |
| L-Tyrosine Disodium Salt | 55.895 |
| L-Cysteine HCl $H_2$0 | 0.87815 |
| L-Cystine 2HCl | 1.567 |
| VITAMINS | |
| Biotin | 0.24431 |
| Pyridoxine HCl | 0.030846 |
| Folic Acid | 2207 |
| Riboflavin | 18.819 |
| Vitamin $B_{12}$ | 67.769 |
| L-Carnitine | 3.96 |
| Choline Chloride | 139.62 |
| i-Inositol | 12.611 |
| Niacinamide | 6.107 |
| D-Calcium Pantothenate | 23.827 |
| Pyridoxal HCl | 10.181 |

TABLE 9-continued

TR-10 Composition.

| | mg/L |
|---|---|
| Thiamine HCl | 16.864 |
| Ascorbic Acid 2 Phos mg | 28.954 |

Two weeks later Neuroscreen® assays were prepared as described in Example 9. Nerve growth factor (NGF) response curves were developed (see FIG. 23). Since each well in the 96-well plate of the Neuroscreen® assay receives 200 μl of solution, the wells with a 100 ng/ml concentration of NGF received a total of 20 ng of NGF.

Since earlier studies had showed that addition of 10 mg of regeneration matrix doubled the average neurite length (of neurites over 10 μm in length) of Neuroscreen® cells exposed to 100 ng/ml of NGF (see Table 10), an experiment was performed in order to determine the effect of adding NGF to the starting matrix solution on this assay.

TABLE 10

Average Neurite Length of Neuroscreen ™ cells exposed to RMx and 100 ng/ml NGF. Values are expressed as the percentage of the positive control (100 ng/ml NGF).

| Batch | Days | $RM_x$ | StDev |
|---|---|---|---|
| 51 | 6 | 170% | 46% |
| | 12 | 159% | 21% |
| | 15 | ND | NA |
| | 18 | ND | NA |
| | 21 | 176% | NA |
| 52 | 6 | 147% | 23% |
| | 12 | 184% | 26% |
| | 15 | 299% | NA |
| | 18 | ND | NA |
| | 21 | 244% | 64% |
| 53 | 6 | 266% | 5% |
| | 15 | 242% | 31% |
| | 18 | 169% | 28% |
| | 21 | 186% | 20% |
| 54 | 6 | 148% | NA |
| | 12 | 211% | 36% |
| | 15 | 212% | 44% |
| | 18 | 223% | 26% |
| | 21 | 263% | 25% |
| 55 | 12 | 245% | 87% |
| | 15 | 222% | 30% |
| 56 | 6 | 163% | 25% |
| | 12 | 267% | 72% |
| | 15 | ND | NA |
| | 21 | 225% | 49% |
| 57 | 12 | 192% | 33% |
| | 21 | 221% | 36% |
| 58 | 12 | 192% | 65% |
| | 15 | 214% | 28% |
| | 21 | 184% | 39% |
| Average | | 209% | 40% |

ND. Not determined.
NA. Not applicable (either from ND or one data point only)

Three of the five regeneration matrices and their corresponding solutions (saved supernatant) from each group were used to determine response curves (see below) in the Neuroscreen® assay. Very similar results of doubling of the average neurite length (of neutrites over 10 μm in length) of Neuroscreen® cells was obtained when the Neuroscreen® cells were exposed to the NGF-containing regeneration matrix (see below). However, this doubling effect was obtained with only 0.2 mg of the regeneration matrix made from whole blood, and 0.03 mg of the regeneration matrix made from the plasma-platelet-buffy coat fraction (without the erythrocyte fraction, see FIG. 24). If the NGF added to the starting matrix solution was equally dispersed between the forming regeneration matrix and surrounding solution, the total amount of regeneration matrix added to the wells of the Neurosreen® assay contained only 0.02 ng and 0.003 ng of NGF for the regeneration matrices made from whole blood and the plasma-platelet-buffy coat fraction, respectively. If all the NGF ended up in the regeneration matrices, then the total amount of NGF per well would be 0.2 ng and 0.03 ng, respectively. However, the standard NGF response curves (that were performed in parallel to these experiments with the same NGF at the same time (NGF freshness) point show that there is limited or no effect of fresh NGF on Neuroscreen® cells at amounts less than 10 ng per well, and maximal responses occur at 100 ng of NGF per well. Since the regeneration matrix made from the plasma-platelet-buffy coat fraction provides a doubling of this maximal response at ⅓₀₀₀th to ⅓₀₀₀₀th (or less) of the NGF amount (or concentration), the regeneration matrix must have a growth factor sensitizing (or similar) effect on Neuroscreen® cells along with the stimulation of other neurite growth pathways since the average neurite length was doubled over the maximum threshold value that can be achieved with NGF alone. Regeneration matrix alone (without any NGF) has been determined to result in an average neurite length of Neuroscreen® cells of approximately 60% of the positive control (100 ng/ml of NGF).

Interestingly, the supernatant (or solution surrounding the regeneration matrix in each Opticell® at the end of the 13-day regeneration matrix forming period) also caused a doubling of the maximal response of Neuroscreen® cells to NGF. If the NGF added to the starting matrix solution was equally dispersed between the forming regeneration matrix and surrounding solution (supernatant), the doubling effect (or maximal response) occurs with only 5 ng of NGF per well, or 1/20th of the NGF amount (or concentration) required for the standard maximal response (which is only ½ of the response obtained with the supernatant). Thus, similar effects are seen in the supernatant as in the regeneration matrix, albeit at a much lower potency. This appears to be due to properties that exist and form during the process that also results in the formation of the regeneration matrix, as well as tiny particles of regeneration matrix that had not yet aggregated into the regeneration matrix complexes.

Furthermore, since the activity of NGF decreases over time at 37° C., the regeneration matrix also appears to have growth factor activity protecting effects. The NGF activity assay on 13-day old regeneration matrix that was stored at 4° C. for an additional two weeks shows a much higher NGF-activity than fresh NGF from the same lot. The same effects were observed with EGF, bFGF, and BDNF in earlier experiments.

Example 9

Dose Response to Regeneration Matrix Prepared with DMEM/F12 Base Media and TR-10 Base Media Table 11 shows a comparison of the dose response to neurite extensibility (assays prepared as in Example 7) of regeneration matrices prepared with either DMEM/f12 base media or TR-10 base media. Values are expressed as the percentage of the positive control (NGF).

TABLE 11

| RM$_x$ (mg) | DMEM/F12 | St.Dev. | TR-10 | St.Dev. |
|---|---|---|---|---|
| 0 | 23% | 5% | 24% | 2% |
| 1 | 60% | 6% | 67% | 11% |
| 5 | 77% | 5% | 103% | 5% |
| 10 | 88% | 5% | 101% | 5% |

Example 10

Effect of Regeneration Matrix on Primary Cell Cultures from Fetal Rat Spinal Cord Spinal cords were obtained from healthy rat fetuses (E18) and adults. The neuronal culture protocol used was adapted from Brewer et al. (*Serum-free B27/neurobasal medium supports differentiated growth of neurons from the striatum, substantia nigra, septum, cerebral cortex, cerebellum, and dentate gyrus*, J. Neurosci. Res. 42, 674-683, 1995). Spinal cords were rapidly dissected from the animal in 2 ml Hibernate-A (Brainbits, Springfield, Ill.), supplemented with B27 (Cat. # 17504-044, Invitrogen) and 0.5 mM L-glutamine (Cat. # 25-005-CI, Mediatech) at 4° C. in a 35 mm petri dish. Meninges and excess white matter were removed in the same medium to a second dish at 4° C. Spinal cords were transferred to sterile paper pre-wet with the same medium and approximately 0.5 mm thick slices were made perpendicular to the long axis of the spinal cord and transferred to a tube at 4° C. of the same medium. After shaking for 8 minutes at 30° C., slices were transferred, with a wide bore pipette, to another tube at 30° C. containing papain. Papain (15-23 units/mg protein, and not activated by cysteine) was prepared by dissolving 12 mg in 6 ml Hibernate A, warming for 5 min at 37° C. The solution was filter sterilized and stored at 4° C. Slices were incubated for 30 min in a 30° C. water bath, with a platform rotating at a speed sufficient to suspend the slices (170 rpm). Slices were transferred to a 15 ml conical tube containing 2 ml Hibernate-A/B27 at 30° C. and allowed to sit for 5 min at RT. Slices were triturated 10 times (in about 30 sec) with a siliconized pasteur pipette (fire polished tip). The pieces were allowed to settle for 2 min and the supernatant was transferred to another tube. The sediment from the first tube was resuspended in 2 ml Hibernate A/B27 and the trituration and settling procedure repeated 2 more times. The supernatants from each trituration were combined yielding a 6 ml suspension.

Cells were plated at 90-320/mm$^2$ in 60-150 µl Neurobasal-A/B27, onto autoclaved glass previously coated with 50 µg/ml lysine-arginine co-polymer (LAS, BrainBits) and distributed into a 100 mm dish. One hour after plating and incubation (5.0% O$_2$, 5.0% CO$_2$, balance N$_2$) the coverslip was quickly picked up, allowed to drain and transferred into 0.4 ml Neurobasal-A/B27 in a 24-well plate at 37° C. The medium was aspirated, the coverslip rinsed once with warm Hibernate-A, and the cells re-fed with Neurobasal-A/B27, 0.5 mM glutamine, 10 µg/ml gentamycin and 5 ng/ml bFGF. Cells were fed at day 4 by removing one half of the medium replacing it with an equal volume of fresh medium containing 5 ng/ml bFGF. Neuronal cells were allowed to attach and proliferate for 6 days before they were used for interaction experiments. They appeared healthy, proliferated steadily and were between 40-60% confluent at the time of the start of the interactions.

Three different batches of matrix were evaluated at days 16, 9 and 7 days, respectively. All three batches were derived from non-clotted blood collected using EDTA as anticoagulant. Two batches contained glucose, glutamine and pyruvate, while one batch did not. Single cell suspensions of whole embryonic (E18) rat spinal cords were prepared according to the above protocol. Cell monolayers were grown on glass coverslips and incubated with either matrix or control medium. At 7 days after the beginning of the interaction culture the coverslips were processed for ICC. Control primary spinal cord cells without the matrix were used as a positive control for the functionality of the culture system.

Micrographs displaying the results of immunocytochemical analysis are shown in FIGS. 25 and 26. Controls stained positive for mature neurons, which all stained negative for glial cells (FIG. 25). In the control cultures, the number of Tuj1 positive cells is 4.2%, GFAP positive cells is 0.4%. No cells were detected that stained both Tuj1 and GFAP positive.

Neuronal cells incubated with matrix exhibited a lower percentage of prominent, long axons; however, the percentage of Tuj1 positive cells within the culture increased to 55% with regeneration matrix (with most of the staining confined to cell bodies and short processes) versus 4.2% without regeneration matrix. The percentage of GFAP positive cells within the culture increased to 92% with regeneration matrix versus only 0.4% for the controls. In the culture treated with the regeneration matrix, approximately 50% of the cells were both Tuj1 and GFAP positive, indicating that they were triphasic neuroprogenitor cells, whereas in the control no such cells were observed.

This observation indicates that the regeneration matrix promotes the proliferation of young new neurons. Increase in the presence of astrocytes during the same time period may represent a phenomenon of tissue neurogenesis and/or an initial "injury" response, a step required for and preceding a healing cascade.

As seen in FIG. 26, the cells treated with the regeneration matrix contained cells that were both Tuj1 and GFAP positive, indicating that they were triphasic neuroprogenitor cells, whereas the control culture showed no such cells.

Example 11

Effect of Regeneration Matrix on Human Fibroblasts In Vitro

Human neonatal foreskin fibroblasts (Cell Line # CCD 1079 Sk, Cat. # CRL 2097, ATCC) were maintained prior to the interaction assay by routine culture and passage at confluence using basal fibroblast medium (DMEM with 10% FBS, and pen-strep). Cells were trypsinized and plated onto either empty Opticell® membrane (Opticell®) or and Opticell® membrane with attached regeneration matrix formed using clotted blood (Regeneration Matrix). Membranes were cut to 1 cm$^2$. The membranes were previously attached to the bottom of a 6 well plate using a small piece of sterile Vaseline. The Vaseline point was placed at the bottom of the well before adding medium and medium was subsequently added and the membranes placed last by pressing at their center from the top. Each well contained 2 Opticell® and 2 regeneration matrix treatments. Cells trypsinized from a confluent plate, were counted and plated at a density of 20,000 cells per well in 3 ml of medium. Plates are placed in the incubator and after 2 hours some representative samples were fixed and their nuclei stained and cell numbers estimated. The rest of the membranes were not disturbed for 2 additional days. BrdU (Cat#203806, EMD Biosciences) was added to 20 µM in growth medium by diluting a 10 mM stock. After the incubation period, the membranes were immersed in 1 ml of ice cold 70% ethanol (Cat# UN 1170, EM Science) in 15 mM glycine (Cat#G-8790, Sigma) in a 24 well plate. The fixed cells were stored at −20 C for at least 24 hr. For BrdU detection, cells were washed once in PBS (Cat. # MT21-030-CM, Mediatech), treated with a 1:10 dilution of the monoclonal anti BrdU antibody-nuclease reagent for the KitII (Cat# 1299964, Roche) and incubated for 1 hr at 37° C. Cells were washed 2× in PBS and incubated with a 1:200 dilution of Alexa-488 conjugated goat anti mouse antibody (Cat. # A11029, Invitrogen) in blocking buffer (10% Normal goat serum Cat. # S26-100M, Chemicon, 5% BSA Cat. # 2910, Omnipure, 0.1% Saponin Cat. #102855, MP-Biochemicals, final solution sterile filtered through a 0.2 μm filter and stored at 4° C.) at room temperature for 1 hr. Samples were counterstained with 2 μg/ml Hoechst 33342 (Cat. # H1399, Invitrogen, 10 mg/ml stock kept at −20° C.) in PBS for 30 min and washed once in PBS. The membranes were then inverted and mounted in 50l1 of glycerol again on a 24 well plate. The plate was stored at 4° C. until scanned, within a week.

Image analysis was done with a KineticScan (Cellomics, V2.2.0.0 Build 19) using Bio-application software Target Activation V2.0. Images were stored to the hard drive in Cellomics proprietary format and analyzed while the plate was scanned. Settings for thresholding of positive cells were obtained by plotting a histogram of the negative and positive cells for each staining session. Plates where the cells had been dislodged from all wells during fixation or where no signal was observed were not included in the final analysis Cells growing on Opticell® membrane had a total of 21.8±2.6% of positives for BrdU, while only 13.4±2.0% were positive when grown on the regeneration matrix. Differences in initial attachment were ruled out by counting the cells just after attachment (i.e., the total number of cells attached were identical between the two samples).

Fibroblasts attach to the regeneration matrix in 2 hr at the same numbers as to a control Opticell®, but the nuclear size is reduced (possibly indicative of the first stages of apoptosis) and the number of BrdU-positive cells is decreased in the fibroblasts growing on the regeneration matrix over a 24 h period (see FIGS. 28A-C). Fibroblast cultures grown for longer periods on these regeneration matrices result in a dramatically lower density of fibroblasts (with some of these fibroblasts undergoing apoptosis) compared to control cultures. FIG. 27 shows this difference in growth density of fibroblasts grown for 5 days on on regeneration matrices made from 5 μm-filtered whole blood.

Example 12

Effect of Regeneration Matrix on Human Astrocytes In Vitro

The same treatments and culture conditions as for fibroblasts were used for astrocytes, except that the morphological change assay was done using staining for glial fibriliary acid protein (GFAP). Primary human astrocytes (Cat. # 1800, Sciencell, San Diego, Calif.) were cultured in basal medium (Astrocyte Medium, Cat. # 1801, ScienCell) on poly-D-lysine coated plates and passaged at confluence. One day before the interaction experiments, cells were trypsinized, counted and plated at 2000 cells per well for BrdU in poly-D-lysine coated 96-well plates (Cat. # 354461, BD Falcon).

For each batch, samples were taken for the above analyses at 0, 6, 12, 15, 18, and 21 days after initiation. Each treatment was replicated 4 times for each measurement (e.g. 4 wells per sample). For proliferation, after 2 days in the presence of the regeneration matrix, BrdU (Cat#203806, EMD Biosciences) was added to 20 μM in growth medium by diluting a 400 μM stock 1:20 into 200 μl medium. The cells were incubated at 37° C., 5% $O_2$, 5% $CO_2$, balance $N_2$ for an additional 1.5 hr. The medium was removed by decantation and the cells fixed with ice cold 70% ethanol (Cat# UN1170, EM Science) in 15 mM glycine (Cat#G-8790, Sigma). The fixed cells were stored at −20° C. for at least 24 hr. For BrdU detection, cells were washed once in 20011 PBS (Cat. # MT21-030-CM, Mediatech), treated with a 1:80 dilution of the monoclonal anti BrdU antibody-nuclease reagent for the KitII (Cat# 1299964, Roche) and incubated for 1 hr at 37° C. Cells were washed 2× in PBS and incubated with a 1:200 dilution of Alexa-488 conjugated goat anti mouse antibody (Cat. # A11029, Invitrogen) in blocking buffer (10% Normal goat serum Cat. # S26-100M, Chemicon, 5% BSA Cat. # 2910, Omnipure, 0.1% Saponin Cat. #102855, MP-Biochemicals, final solution sterile filtered through 0.2 um and stored at 4 C) at room temperature for 1 hr. Samples were counterstained with 2 μg/ml Hoechst 33342 (Cat. # H1399, Invitrogen, 10 mg/ml stock kept at −20 C) in PBS for 30 min and washed once in PBS and stored at 4° C. until scanned, usually within a week. After ethanol fixation and storage, the cells were treated with 2N HCl (Cat# 2612-14, Mallinckrodt chemicals) for 30 min and neutralized with 100 mM Tris, HCl pH 8.5 (Cat# 9230, OmniPure) and washed 2× with PBS. The cells were incubated in 50 μl of a 1:200 dilution of Alexa-488 conjugated monoclonal antibody against BrdU (Cat#MD5420, Caltag laboratories) in blocking buffer for 16 hr at 4° C. The cells were washed twice in PBS and incubated with a 1:200 dilution of Alexa 546 conjugated goat anti mouse (Cat#A11030, Invitrogen) in blocking buffer for 3 hr. Cells were counterstained in 200 μl of 2 μg/ml Hoechst in PBS for 30 min and stored in PBS. Image analysis was done with a KineticScan (Cellomics, V2.2.0.0 Build 19) using Bio-application software Target Activation V2.0. Images were stored to the hard drive in Cellomics proprietary format and analyzed while the plate was scanned. Settings for threshholding of positive cells were obtained by plotting a histogram of the negative and positive cells for each staining session. Plates where the cells had been dislodged from all wells during fixation or where no signal was observed were not included in the final analysis. Overall, the astrocytes cultured in the presence of the regeneration matrix had fewer BrdU positive nuclei (13.9±2.3%) than those cultured without regeneration matrix (18.5±2.4%), which provides a possible explanation for the observation of reduced glial scarring in spinal cord injuries treated with regeneration matrix compared to controls.

Example 13

Effect of Regeneration Matrix on Injured Rat Spinal Cord in Vivo

To evaluate the in vivo activity of a regeneration matrix, three rat models of spinal cord injury models were used:
Complete Transection (5 mm defect).
Hemisection (5 mm defect, right side).
Contusion (50 mm weight drop).
All animal studies were performed using IACUC approved protocols with standardized surgical and post-surgical animal care procedures. Nude rats (Biomedical Research Models, Inc., Worcester, Mass.) were used in these studies to minimize immunological reactions to the human regeneration matrix. To access the spinal cord, an incision was made in the midline, above the spine from T8 to T11 and the skin and dorso-lumbar fascia retracted. Both sides of the spine were exposed by blunt dissection. A dorsal laminectomy was performed at the T8-T9 level. The dura mater was cut and retracted, exposing the spinal cord. In the transection studies, a full thickness segment of spinal cord cut between T8 and T9, 5 mm in length was cut and carefully removed. In the hemisection SCI model, the spinal cord was exposed as described above and a 5 mm defect on the right side was surgically created in the spinal cord. The regeneration matrix implant was used to fill the defects. The dura, overlying ligaments, muscles and the skin were closed by suture. In the contusion model, the exposed dura of the spinal cord was impacted by a 50 mm weight drop using the NYU IMPACTOR and the animals were allowed to recover for 2 weeks post-injury. After the 2 week recovery period the animals had the regeneration matrix surgically implanted in the spinal cord adjacent to the injury area. All animals were allowed to recover in their own cages and subcutaneous injection of antibiotics were administered for three days to prevent infections. Sensory and motor functions of all animals were periodically assessed according to the modified version of the BBB neurological scale (Basso, D. M. et al., *A sensitive and reliable locomotor rating scale for open field testing in rats*, J. Neurotrauma 12, 21, 1995). BBB scores were recorded approximately every 2 weeks using the criteria listed in Tables 12 and 13.

TABLE 12

Basso, Beattie And Bresnahan Locomtotor Rating Scale

| Rating | Description of Locomotion |
|---|---|
| 0 | No observable hindlimb (HL) movement |
| 1 | Slight movement of one or two joints (usually hip &/or knee). |
| 2 | Extensive movement of one joint or Extensive movement of one joint and slight movement of one other joint. |
| 3 | Extensive movement of two joints. |
| 4 | Slight movement of all three joints of the HL. |
| 5 | Slight movement of two joints and extensive movement of the third. |
| 6 | Extensive movement of two joints and slight movement of the third. |
| 7 | Extensive movement of all three joints of the HL. |
| 8 | Sweeping with no weight support or Plantar placement of the paw with no weight support. |
| 9 | Plantar placement of the paw with weight support in stance only (i.e. when stationary) or occasional, Frequent or Consistent weight supported dorsal stepping and no plantar stepping. |
| 10 | Occasional weight supported plantar steps, no FL-HL coordination. |

TABLE 12-continued

Basso, Beattie And Bresnahan Locomtotor Rating Scale

| Rating | Description of Locomotion |
|---|---|
| 11 | Frequent to consistent weight supported plantar steps and no FL-HL coordination. |
| 12 | Frequent to consistent weight supported plantar steps and occasional FL-HL coordination. |
| 13 | Frequent to consistent weight supported plantar steps and frequent FL-HL coordination. |
| 14 | Consistent weight supported plantar steps, consistent FL-HL coordination; and Predominant paw position during locomotion is rotated (internally or externally) when it makes initial contact with the surface as well as just before it is lifted off at the end of stance or Frequent plantar stepping, consistent FL-HL coordination and occasional dorsal stepping. |
| 15 | Consistent plantar stepping and Consistent FL-HL coordination; and No toe clearance or occasional toe clearance during forward limb advancement, Predominant paw position is parallel to the body at initial contact. |
| 16 | Consistent plantar stepping and Consistent FL-HL coordination during gait; and Toe clearance occurs frequently during forward limb advancement Predominant paw position is parallel at initial contact and rotated at lift off |
| 17 | Consistent plantar stepping and Consistent FL-HL coordination during gait; and Toe clearance occurs frequently during forward limb advancement, Predominant paw position is parallel at initial contact and lift off. |
| 18 | Consistent plantar stepping and Consistent FL-HL coordination during gait; and Toe clearance occurs consistently during forward limb advancement, Predominant paw position is parallel at initial contact and rotated at lift off |
| 19 | Consistent plantar stepping and Consistent FL-HL coordination during gait; and Toe clearance occurs frequently during forward limb advancement, Predominant paw position is parallel at initial contact and lift off and Tail is down part or all of the time. |
| 20 | Consistent plantar stepping and Consistent coordinated gait; Consistent toe clearance Predominant paw position is parallel at initial contact and lift off; and Trunk instability, tail consistently up. |
| 21 | Consistent plantar stepping and Coordinated gait, consistent toe clearance, Predominant paw position is parallel throughout stance, consistent trunk stability and Tail consistently up. |

TABLE 13

BBB Definitions

| Locomotion | Definition |
|---|---|
| Slight | Partial joint movement through less than half the range of joint motion |
| Extensive | Movement through more than half of the range of motion |
| Sweeping | Rhythmic movement of HL in which all three joints are extended then fully flex and extend again: animal is usually side-lying and plantar surface of paw may or may not contact the ground. No weight support across the HL is evident |
| No Weight Support | No contraction of the extensor muscles of the HL during plantar placement of the paw or no elevation of the hindquarter |
| Weight Support | Contraction of the extensor muscles of the HL during plantar placement of the paw, or elevation of the hindquarter- i.e. look for a change in the hindquarter and abdomen position during stepping. |
| Plantar Stepping | The paw is in plantar contact with weight support then the HL is advanced forward and plantar contact with weight support is re-established |
| Dorsal Stepping | Weight is supported through the dorsal surface of the paw at some point in the step cycle |

TABLE 13-continued

BBB Definitions

| Locomotion | Definition |
| --- | --- |
| FL-HL Coordination | For every FL step a HL step is taken and the HLs alternate. (Only evaluate for periods when >3 steps are taken in a row) |
| Occasional | <50% |
| Frequent | 51-94% |
| Consistent | 95-100% only if there are no prolonged bouts without stepping. |
| Trunk Instability | Lateral weight shifts which cause waddling from side to side or partial collapse of the trunk. |

15a. Full Transection Spinal Cord Injury Model in the Rat

FIG. 29 shows results from full transection studies in rats where the transection injuries were filled with regeneration matrix or left with void space that got filled by blood as controls. In general, there was a high level of mortality associated with this type of study due to the severity of the spinal cord injury and the results depict neurofunctional status in animals that survived at least 6 weeks. BBB scores were monitored at 2 week intervals for up to 12 to 14 weeks post-implant. All seven animals with regeneration matrix implants that survived at least 6 weeks post injury/implant showed improved BBB scores (FIG. 29). Maximal increases were seen at 6-8 weeks post-implant. The three control animals surviving at least 6 weeks showed no substantial improvement over the 12 week evaluation period.

Furthermore, the rats receiving the regeneration matrix implants had significantly decreased number of lesions (cysts) as well as the average volume of each lesion above and below the site of spinal cord injury (surgery) compared to control animals (see FIG. 30). This means that regeneration matrix exhibited neuroprotective effects in these animal models, resulting in more neuronal tissue preservation above and below the site of injury.

15b. Hemisection Spinal Cord Injury Model in the Rat.

FIG. 31 summarizes results where regeneration matrix was implanted into the spinal cord damaged by hemisection. In the hemisection SCI model, the spinal cord was exposed as described above and a 5 mm defect on the right side was surgically created in the spinal cord. This model is not as severe as the transection model and permits some normal animal function. For example, the surgically induced defect allows bladder control but no motor function of right hind limb. Regeneration matrix implantation (n=4) led to increased survival as well as functional recovery (n=3) compared to non-implanted controls (n=2). The non-implanted control animals died before the first BBB evaluation period at 1 week.

15c. Contusion Model of Spinal Cord Injury in the Rat.

In the contusion model, the dura mater with underlying spinal cord was exposed and SCI was induced by a 50 mm weight drop using the MASCIS IMPACTOR (formerly the NYU IMPACTOR, W.M. Keck Center for Collaborative Neuroscience, Rutgers University, Piscataway, N.J.). Rats were allowed to recover for two weeks and then a second surgery was performed where the spinal cord was exposed and the regeneration matrix placed adjacent to the injury area. FIG. 32 shows that regeneration matrix implantation also improves BBB scores in the rats with contusion damaged spinal cord. In this study, 25 rats had contusion damage inflicted on their spinal cord and 19 animals survived 2 weeks post contusion. Of the surviving animals, 11 animals received regeneration matrix implants and 8 served as control animals that received either a biologically inactivated implant or no second surgery (and thus no implant). At 6 weeks after injury, 9 regeneration matrix implanted, 4 inactivated matrix implanted and 3 non-implanted controls were alive. BBB scores for these surviving animals were evaluated at 2 week intervals (FIG. 32). The regeneration matrix implanted animals recovered as in the full transection and hemisection models. The biologically inactivated matrix implanted animals partially recovered indicating that the structural properties of the regeneration matrix alone have significant regenerative potential over controls that received no matrix. For one of the control animals, an apparent substantial spontaneous recovery was seen which appeared to be due to an incomplete injury. However, the minor but measurable debilitating effects of the second surgery were overcome by the implanted matrices that resulted in a significant improvement in the animals.

Example 16

Human Regeneration Matrix is Safe, Well Tolerated, and Supports Functional Recovery in Pigs with Experimental Spinal Cord Injuries In experimental pilot studies, male pigs weighing between 20 to 45 kg received different types of spinal cord injuries (impact, penetration, tear/rip, surgical hemisection) and human regeneration matrix or porcine fibrin plugs were placed into the injury sites. The different models were tested in order to develop an idea of the results of each type of injury on the locomotor and sensory functionality in pigs, as well as get an idea of which injury model a regeneration matrix appeared to work best in. There was a clear trend of the human regeneration matrix promoting functional recovery in pigs with SCI, with the most significant effect seen in severe impact injuries resulting in tearing and loss of spinal cord tissue. These experiments also provided an opportunity to evaluate the tolerability and potential safety of the regeneration matrix implant. The porcine spinal cord is more than 98% identical to the human spinal cord in terms of its microenvironment from T2 to L2, and thus is a good model for determining any potential safety concerns that the regeneration matrix might have in a human spinal cord. No detectable safety concerns were seen in any of the pigs that received the human regeneration matrix implant, including 3 pigs that had a regeneration matrix injected twice into their spinal cords during two separate surgeries that were 1-3 months apart. No significant differences were found between the control animals and the animals that received the regeneration matrix implant in terms of their weights and behaviors, including general observations made during the husbandry of the animals in their eating, drinking, social interactions, urination and defecation behaviors, indicating that the regeneration matrix is well tolerated and relatively non-toxic when implanted into pigs.

Tissue samples taken one month after implantation in some of the pigs and subjected to Tuj-1 staining indicated that the implanted regeneration matrix had induced the formation of new neurons at the site of spinal cord injury. FIG. 37 shows that the implanted regeneration matrices induce formation of new Tuj-1 positive neurons (shown at 200× magnification), within one month of implantation.

These preliminary pilot studies suggested that the human regeneration matrix promotes locomotor recovery in pigs with SCI. FIG. 33 shows the results of these preliminary studies in which a modified ASIA scoring system was used to assess the neurofunctional recovery in these animals. Some of the pigs started with very low ASIA scores due to the severity of the surgical injury while other pigs (including all the control animals) received less severe surgical injuries and thus started at higher ASIA scores.

After the completion of these pilot studies, a complete double-blinded 7-week safety study demonstrated that a human regeneration matrix is safe and well-tolerated in pigs that had received experimental spinal cord injuries. In these double blinded studies, pigs received surgically induced SCI localized to the right side of their spinal cords at T8-T9—a double hemisection, 5 mm apart, followed by removal of the 5 mm-long piece of spinal cord—and were implanted with either a human regeneration matrix or an equivalent amount of homogenized human blood clot. The left side of the spinal cord served as a control for non-specific toxicities related to the experimental surgery and the implants. All animals were routinely observed for changes in overall health status, weight and locomotory responses for 7 weeks post SCI and implant.

Initially, sixteen age- and weight-matched pigs were randomized to 8 groups of 2 animals each that were implanted with either a human regeneration matrix or blood clot. Four animals died shortly after receiving the severe spinal cord injury—two in the regeneration matrix and two in the blood clot treatment groups—indicating that the human regeneration matrix was not associated with an increased mortality relative to the clot implanted group.

Regeneration matrix implantation appeared to be well-tolerated and generally safe in pigs compared to the clot implanted, control animals. FIG. 34 summarizes and compares the weekly weight gains of pigs in the two groups. There were no detectable differences in the mean total weight gains of pigs during the first 5 weeks, with an increase in the weight gain of the regeneration matrix implanted pigs over the control pigs during the last two weeks of the study period. These data suggest that the regeneration matrix is well-tolerated in pigs and is not systemically toxic. Furthermore, the data suggests that the regeneration matrix implanted pigs started gaining more muscle mass over the control pigs during the last two weeks of the study period.

Locomotor functions in all animals were measured initially at 72 h and then at 1-week intervals post SCI using a modified ASIA Sensory and Motor Skill scoring system for the animals' hind legs. FIG. 35 shows the locomotor scores of animals implanted with the regeneration matrix or with the homogenized blood clot.

In these studies, baseline Sensory and Motor Skill scores were measured 72 hours after surgical SCI and implant, used as the starting values, and then scores were determined at weekly intervals for 7 weeks. Pigs in both study groups began recovering locomotor and sensory functions (from spinal cord shock) within 1 week of the surgical SCI and these values reached constant levels 2-4 weeks post implant. No significant differences were observed in the locomotor and sensory functions of the regeneration matrix and clot implanted groups during this 2-4 week time period, indicating that the regeneration matrix does not impede functional recovery in SCI animals nor does it cause any additional impairment of spinal cord function.

An additional increase in sensory and locomotory recovery was observed in most animals approximately 4-6 weeks post-SCI. The recovery levels observed in the regeneration matrix implanted animals at these later time points were higher than observed in the clot implanted animals. A detailed analysis of the differences in these two groups at the 7-week time point indicates that there was significant improvement (p=0.03) in the right side functions (the side that received the injury) of animals receiving the regeneration matrix (FIG. 36). The much higher variability within the regeneration matrix implanted group over the control group at this 7-week time point is indicative of regeneration matrix biological activity that has not yet reached its end-point (final motor score) value. End-point was estimated to have been at about 16 weeks.

Taken together, these studies indicate that the regeneration matrix is safe and well-tolerated in pigs and promotes sensory and locomotor recovery after surgically induced Example 17

Rat GLP Toxicology Study

A GLP, ISO 10993-11 compliant pre-clinical study was designed and performed at NAMSA (Northwood, Ohio) to evaluate the potential for systemic toxicity associated with the implantation of a regeneration matrix. In this study, a regeneration matrix was implanted in the subcutaneous tissue of 14 rats (7 male and 7 female). The control article (sterile 0.9% saline) was similarly implanted into a separate group of 14 rats (7 male and 7 female). Animals were observed daily for mortality and overt signs of toxicity. Detailed examinations for clinical signs of disease or abnormality were conducted weekly. Animal body weights were obtained prior to implantation and at weekly intervals throughout the study.

At 4 weeks, the animals were euthanized and blood specimens were collected for hematology and clinical chemistry analyses (all analyses performed by NAMSA). A necropsy was conducted and selected organs were excised, weighed and processed histologically. The subcutaneous tissue around each implant site was also excised from each rat and examined microscopically. Microscopic evaluation of the implant sites, as well as selected organs was conducted by a qualified pathologist. Body weight, organ weights, organ/body weight ratios, hematology values and clinical chemistry values were analyzed statistically.

Data revealed no evidence of systemic toxicity from the test article (regeneration matrix) following subcutaneous implantation in the rat. Daily clinical observations, body weights, necropsy findings, animal organ weights, and organ/body ratios were within acceptable limits and were similar between and within test and control treatment groups. There were no changes in hematology values or clinical chemistry values in either the male or female rats that were considered to be biologically significant or related to treatment with the test article. The microscopic evaluation of the selected tissues revealed no evidence of systemic toxicity in the group treated with the regeneration matrix. Based on histological criteria, the regeneration matrix in male and female rats was considered to be a moderate irritant when compared with the saline reference control material. This latter finding is within the range of experience of the test facility for evaluation of bio-absorbable materials and on the low range for a xenogeneic implant (in this case, human whole blood derived regeneration matrix was implanted into rat). In conclusion, local injection of a regeneration matrix across species does not lead to any significant toxicities and suggests that a regeneration matrix will not cause local pathology when implanted in human SCI patients.

Example 18

Microscopic Evaluation of Sections from Spinal Cord Regeneration Study

A regeneration matrix was implanted into an experimental rat in which a 10 mm length of its spinal cord had been surgically removed. After 10 days the spinal cord was examined histologically. The central spinal cord defect microscopically consisted of severe central wallerian axonal degeneration and neurophil necrosis that extended about 4.5 mm in radius from center (1 cm total width) due to the surgical removal of the 1 cm length of spinal cord. Surrounding the regeneration matrix implant were sheets of reactive glial and gitter cells, some with hemosiderin, as well as sheets of apparent primitive mesenchymal/reticular type cells (see FIGS. 38A and 38B) that appeared to be expanding (filling) into the spinal cord defect. These cells appeared to be involved in developing of new neural tissue and regeneration of the spinal cord. At the periphery of the defect there was thickening of the leptomenges with increased reactive fibroplasia. The fibroplasia appeared to expand along the leptomeninges as a supporting framework for these apparent primitive mesenchymal/reticular type cells and appeared to support the regeneration of the injured spinal cord.

The foregoing description is intended to be exemplary in nature and is not intended to be a limiting recitation of the invention, its application, or uses. One of ordinary skill in the art will appreciate that certain modifications may be made to one or more of the embodiments of the present invention described herein, which modifications are nonetheless within the scope of the present invention. Alternative methods and materials for implementing the invention as well as additional applications will be apparent to one of skill in the art, and are intended to be included within the accompanying claims.

What is claimed is:

1. A method of producing an acellular bioabsorbable tissue regeneration matrix, said method comprising:
   (a) providing an isolated blood sample;
   (b) removing intact living cells from said blood sample to obtain an acellular fraction;
   (c) combining said acellular fraction with a process medium to form a starting material;
   (d) incubating said starting material in an incubation chamber for a first period of time to form an acellular bioabsorbable tissue regeneration matrix; and
   (e) isolating said acellular bioabsorbable tissue regeneration matrix;
   wherein said acellular bioabsorbable tissue regeneration matrix has a regenerative effect towards cells which is not present in the starting material, and/or wherein said acellular bioabsorbable tissue regeneration matrix has significantly greater regenerative effect towards cells compared to the starting material.

2. The method of claim 1, wherein said blood sample comprises a blood fraction.

3. The method of claim 2, wherein said blood fraction comprises a buffy-coat layer.

4. The method of claim 2, wherein said blood fraction comprises a buffy-coat/platelet/plasma layer.

5. The method of claim 1, wherein said blood sample comprises an anticoagulant.

6. The method of claim 1, wherein said blood sample comprises one or more clots, and said method further comprises solubilizing said one or more clots.

7. The method of claim 1, wherein said removing intact cells is effected by freezing, filtration and/or centrifugation.

8. The method of claim 1, wherein said removing comprises passing the tissue sample through a size selection filter.

9. The method of claim 8, wherein said size selection filter excludes particles larger than about 5 µm.

10. The method of claim 8, wherein said size selection filter excludes particles larger than about 1.2 µm.

11. The method of claim 8, wherein said size selection filter excludes particles larger than about 0.8 µm.

12. The method of claim 1, wherein said acellular fraction is in the form of a liquid solution or suspension.

13. The method of claim 1, wherein said incubation chamber is impermeable to solid or liquid matter.

14. The method of claim 13, wherein said incubation is permeable to gases generated by evaporation of liquid inside the incubation chamber.

15. The method of claim 14, wherein said incubation chamber is incubated in a low humidity environment, such that the evaporation rate of liquid inside the incubation chamber is increased.

16. The method of claim 14, wherein said evaporation of liquid results in an increase in osmolarity of the liquid solution or suspension over the first period of time.

17. The method of claim 1, wherein the osmolarity of the acellular fraction is controlled such that the acellular bioabsorbable tissue regeneration matrix formed during said first period of time is in the form of a three-dimensional matrix.

18. The method of claim 1, wherein the osmolarity of the acellular fraction is controlled such that the acellular bioabsorbable tissue regeneration matrix formed during said first period of time is in the form of a suspension.

19. The method of claim 1, wherein said first period of time is at least 5 days.

20. The method of claim 1, wherein said first period of time is at least 12 days.

21. The method of claim 1, wherein said incubating comprises incubating said acellular sample in a low oxygen environment.

22. The method of claim 21, wherein said low oxygen environment comprises an environment with less than about 5% oxygen.

23. The method of claim 21, wherein said low oxygen environment comprises an environment that substantially lacks oxygen.

24. The method of claim 21, wherein said first period of time is at least 3 days.

25. The method of claim 21, wherein said first period of time is at least 7 days.

26. The method of claim 1, further comprising adding process medium to said isolated blood sample and/or said acellular fraction and/or said starting material
(i) during isolation of the blood sample;
(ii) prior to the removing step;
(iii) prior to the combining step;
(iv) during the combining step;
(v) prior to the incubating step;
(vi) during the incubating step; or
(vii) any combination thereof.

27. The method of claim 26, wherein said process medium comprises a physiological solution.

28. The method of claim 1, further comprising adding one or more therapeutic agents at one or more steps selected from the group consisting of:
(i) to the blood sample during the isolation thereof prior to (a);
(ii) to the blood sample prior to (b);
(iii) to the acellular fraction prior to (c);
(iv) to the acellular fraction during (c);
(v) to the starting material after (c);
(vi) to the starting material during (d);
(vii) to the regeneration matrix after (d);
(viii) to the isolated regeneration matrix after (e); and
(ix) any combination thereof.

29. The method of claim 28, wherein said one or more therapeutic agents is selected from the group consisting of:
(i) proteins,
(ii) peptides,
(iii) drugs,
(iv) cytokines,
(v) extracellular matrix molecules,
(vi) growth factors, and
(vii) any combination thereof.

30. The method of claim 1, further comprising seeding or mixing said acellular bioabsorbable tissue regeneration matrix with cells after formation thereof, wherein said cells are added during or after (e).

31. The method of claim 30, wherein said cells are selected from the group consisting of:
(i) stem cells,
(ii) progenitor cells,
(iii) somatic cells, and
(iv) any combination thereof.

32. The method of claim 30, wherein the cells are selected from the group consisting of: embryonic stem cells, neural stem cells, neuroprogenitor cells, neurons, glial cells, and combinations thereof.

33. The method of claim 1, further comprising seeding or mixing said acellular bioabsorbable tissue regeneration matrix with cells while it is being produced.

34. The method of claim 33, wherein said cells are selected from the group consisting of:
(i) stem cells,
(ii) progenitor cells,
(iii) somatic cells, and
(iv) any combination thereof.

35. The method of claim 33, wherein the cells are selected from the group consisting of: embryonic stem cells, neural stem cells, neuroprogenitor cells, neurons, glial cells, and combinations thereof.

36. The method of claim 1, wherein said acellular bioabsorbable tissue regeneration matrix supports, induces and/or controls an activity selected from the group consisting of:
(i) tissue growth,
(ii) cell growth,
(iii) gene upregulation,
(iv) cell inhibition,
(v) cell proliferation,
(vi) cell dedifferentiation,
(viii) cell transdifferentiation,
(ix) neurite outgrowth,
(x) one or more natural wound healing processes, and
(xi) any combination thereof.

37. A method of producing an acellular bioabsorbable tissue regeneration matrix, said method comprising:
(a) providing an isolated blood sample;
(b) combining the isolated blood sample with a process medium into a first mixture;

(c) removing intact living cells from said first mixture to obtain an acellular starting material;
(d) incubating said starting material for a first period of time to form an acellular bioabsorbable tissue regeneration matrix; and
(e) isolating said acellular bioabsorbable tissue regeneration matrix;
wherein said acellular bioabsorbable tissue regeneration matrix has a regenerative effect towards cells which is not present in the starting material, and/or wherein said acellular bioabsorbable tissue regeneration matrix has significantly greater regenerative effect towards cells compared to the starting material.

38. The method of claim 37, wherein said blood sample comprises a blood fraction.

39. The method of claim 38, wherein said blood fraction comprises a buffy-coat layer.

40. The method of claim 38, wherein said blood fraction comprises a buffy-coat/platelet/plasma layer.

41. The method of claim 37, wherein said blood sample comprises an anticoagulant.

42. The method of claim 37, wherein said blood sample comprises one or more clots, and said method further comprises solubilizing said one or more clots.

43. The method of claim 37, wherein said removing intact cells is effected by freezing, filtration and/or centrifugation.

44. The method of claim 37, wherein said removing comprises passing the first mixture through a size selection filter.

45. The method of claim 44, wherein said size selection filter excludes particles larger than about 5 μm.

46. The method of claim 44, wherein said size selection filter excludes particles larger than about 1.2 μm.

47. The method of claim 44, wherein said size selection filter excludes particles larger than about 0.8 μm.

48. The method of claim 37, wherein said acellular starting material is in the form of a liquid solution or suspension.

49. The method of claim 37, wherein said incubation chamber is impermeable to solid or liquid matter.

50. The method of claim 49, wherein said incubation is permeable to gases generated by evaporation of liquid inside the incubation chamber.

51. The method of claim 50, wherein said incubation chamber is incubated in a low humidity environment, such that the evaporation rate of liquid inside the incubation chamber is increased.

52. The method of claim 50, wherein said evaporation of liquid results in an increase in osmolarity of the liquid solution or suspension over the first period of time.

53. The method of claim 37, wherein the osmolarity of the acellular starting material is controlled such that the acellular bioabsorbable tissue regeneration matrix formed during said first period of time is in the form of a three-dimensional matrix.

54. The method of claim 37, wherein the osmolarity of the acellular starting mixture is controlled such that the acellular bioabsorbable tissue regeneration matrix formed during said first period of time is in the form of a suspension.

55. The method of claim 37, wherein said first period of time is at least 5 days.

56. The method of claim 37, wherein said first period of time is at least 12 days.

57. The method of claim 37, wherein said incubating comprises incubating said acellular starting material in a low oxygen environment.

58. The method of claim 57, wherein said low oxygen environment comprises an environment with less than about 5% oxygen.

59. The method of claim 57, wherein said low oxygen environment comprises an environment that substantially lacks oxygen.

60. The method of claim 57, wherein said first period of time is at least 3 days.

61. The method of claim 57, wherein said first period of time is at least 7 days.

62. The method of claim 37, further comprising adding process medium to said isolated blood sample and/or said first mixture and/or said starting material wherein said process medium is added:
(i) during isolation of the blood sample;
(ii) prior to the combining step;
(iii) during the combining step;
(iv) prior to the removing step;
(v) prior to the incubating step;
(vi) during the incubating step; or
(vii) any combination thereof.

63. The method of claim 62, wherein said process medium comprises a physiological solution.

64. The method of claim 37, further comprising adding one or more therapeutic agents at one or more steps selected from the group consisting of:
(i) to the blood sample during the isolation thereof prior to (a);
(ii) to the blood sample prior to (b);
(iii) to the first mixture during (b);
(iv) to the first mixture prior to (c);
(v) to the starting material after (c);
(vi) to the starting material during (d);
(vii) to the regeneration matrix after (d);
(viii) to the isolated regeneration matrix after (e); and
(ix) any combination thereof.

65. The method of claim 64, wherein said one or more therapeutic agents is selected from the group consisting of:
(i) proteins,
(ii) peptides,
(iii) drugs,
(iv) cytokines,
(v) extracellular matrix molecules,
(vi) growth factors, and
(vii) any combination thereof.

66. The method of claim 37, further comprising seeding or mixing said acellular bioabsorbable tissue regeneration matrix with cells after formation thereof, wherein said cells are added during or after (e).

67. The method of claim 66, wherein said cells are selected from the group consisting of:
(i) stem cells,
(ii) progenitor cells,
(iii) somatic cells, and
(iv) any combination thereof.

68. The method of claim 66, wherein the cells are selected from the group consisting of:
embryonic stem cells, neural stem cells, neuroprogenitor cells, neurons, glial cells, and combinations thereof.

69. The method of claim 37, further comprising seeding or mixing said acellular bioabsorbable tissue regeneration matrix with cells while it is being produced.

70. The method of claim 69, wherein said cells are selected from the group consisting of:
(i) stem cells,
(ii) progenitor cells,
(iii) somatic cells, and
(iv) any combination thereof.

71. The method of claim 69, wherein the cells are selected from the group consisting of:
   embryonic stem cells, neural stem cells, neuroprogenitor cells, neurons, glial cells, and combinations thereof.

72. The method of claim 37, wherein said acellular bioabsorbable tissue regeneration matrix supports, induces and/or controls an activity selected from the group consisting of:
   (i) tissue growth,
   (ii) cell growth,
   (iii) gene upregulation,
   (iv) cell inhibition,
   (v) cell proliferation,
   (vi) cell dedifferentiation,
   (viii) cell transdifferentiation,
   (ix) neurite outgrowth,
   (x) one or more natural wound healing processes, and
   (xi) any combination thereof.

73. An acellular bioabsorbable tissue regeneration matrix generated according to the method of any one of claims 2-15, 26-29, 17-36, 7 or, 37-72 wherein said acellular regeneration matrix:
   (a) comprises aggregates of spherical structures having approximately 100 nm to 4 microns in diameter,
   (b) is self-assembled;
   (c) comprises a proteinaceous core having a majority of protein content derived from blood;
   (d) lacks substantial metabolic activity; or
   (e) any combination of (a) to (d).

* * * * *